(12) United States Patent
Shah et al.

(10) Patent No.: US 12,303,592 B2
(45) Date of Patent: May 20, 2025

(54) FORMULATIONS FOR PARENTERAL DELIVERY OF COMPOUNDS AND USES THEREOF

(71) Applicant: Wyeth, LLC, Madison, NJ (US)

(72) Inventors: Syed M. Shah, Delray Beach, FL (US); Christian Ofslager, Newburgh, NY (US); Mahdi B. Fawzi, Morristown, NJ (US); Nataliya Bazhina, Tappan, NY (US)

(73) Assignee: Wyeth, LLC, Madison, NJ (US)

( * ) Notice: Subject to any disclaimer, the term of this patent is extended or adjusted under 35 U.S.C. 154(b) by 0 days.

(21) Appl. No.: 18/244,446

(22) Filed: Sep. 11, 2023

(65) Prior Publication Data

US 2023/0414490 A1 Dec. 28, 2023

Related U.S. Application Data

(63) Continuation of application No. 17/357,023, filed on Jun. 24, 2021, now abandoned, which is a continuation of application No. 16/514,722, filed on Jul. 17, 2019, now abandoned, which is a continuation of application No. 15/158,967, filed on May 19, 2016, now abandoned, which is a continuation of application No. 14/105,805, filed on Dec. 13, 2013, now abandoned, which is a continuation of application No. 12/726,113, filed on Mar. 17, 2010, now abandoned, which is a continuation of application No. 11/890,034, filed on Aug. 3, 2007, now abandoned.

(60) Provisional application No. 60/835,574, filed on Aug. 4, 2006.

(51) Int. Cl.
| | | |
|---|---|---|
| A61K 9/00 | (2006.01) | |
| A61K 31/485 | (2006.01) | |
| A61K 47/02 | (2006.01) | |
| A61K 47/18 | (2017.01) | |

(52) U.S. Cl.
CPC .......... *A61K 9/0019* (2013.01); *A61K 31/485* (2013.01); *A61K 47/02* (2013.01); *A61K 47/183* (2013.01)

(58) Field of Classification Search
CPC .... A61K 9/0019; A61K 31/485; A61K 47/02; A61K 47/183
See application file for complete search history.

(56) References Cited

U.S. PATENT DOCUMENTS

| | | |
|---|---|---|
| 3,714,159 A | 1/1973 | Janssen et al. |
| 3,723,440 A | 3/1973 | Freter et al. |
| 3,854,480 A | 12/1974 | Zaffaroni |
| 3,884,916 A | 5/1975 | Janssen et al. |
| 3,937,801 A | 2/1976 | Lippmann |
| 3,996,214 A | 12/1976 | Dajani et al. |
| 4,012,393 A | 3/1977 | Markos et al. |
| 4,013,668 A | 3/1977 | Adelstein et al. |
| 4,025,652 A | 5/1977 | Diamond et al. |
| 4,060,635 A | 11/1977 | Diamond et al. |
| 4,066,654 A | 1/1978 | Adelstein et al. |
| 4,069,223 A | 1/1978 | Adelstein |
| 4,072,686 A | 2/1978 | Adelstein et al. |
| 4,115,400 A | 9/1978 | Zimmerman |
| 4,115,564 A | 9/1978 | Diamond et al. |
| 4,116,963 A | 9/1978 | Adelstein |
| 4,125,531 A | 11/1978 | Yen |
| 4,176,186 A | 11/1979 | Goldberg et al. |
| 4,194,045 A | 3/1980 | Adelstein |
| 4,203,920 A | 5/1980 | Diamond et al. |
| 4,241,066 A | 12/1980 | Kobylecki et al. |
| 4,277,605 A | 7/1981 | Buyniski et al. |
| 4,311,833 A | 1/1982 | Namikoshi et al. |
| 4,322,426 A | 3/1982 | Hermann et al. |
| 4,326,074 A | 4/1982 | Diamond et al. |
| 4,326,075 A | 4/1982 | Diamond et al. |
| 4,377,568 A | 3/1983 | Chopra |
| 4,385,078 A | 5/1983 | Onda et al. |
| 4,427,676 A | 1/1984 | White et al. |
| 4,430,327 A | 2/1984 | Frederickson |
| 4,452,775 A | 6/1984 | Kent |
| 4,457,907 A | 7/1984 | Porter |
| 4,462,839 A | 7/1984 | McGinley et al. |
| 4,466,968 A | 8/1984 | Bernstein |
| 4,518,433 A | 5/1985 | McGinley et al. |
| 4,533,739 A | 8/1985 | Pitzele et al. |
| 4,556,552 A | 12/1985 | Porter et al. |
| 4,606,909 A | 8/1986 | Bechgaard et al. |
| 4,615,885 A | 10/1986 | Nakagame et al. |

(Continued)

FOREIGN PATENT DOCUMENTS

| | | |
|---|---|---|
| AU | 610561 B2 | 8/1988 |
| AU | 758416 B2 | 3/2003 |

(Continued)

OTHER PUBLICATIONS

[No Author Listed] Cancer Pain Remedy Wins Orphan Drug Status. Oncology. 1996; 10(12): 1880.

(Continued)

*Primary Examiner* — Amanda L. Aguirre
*Assistant Examiner* — William Y Lee
(74) *Attorney, Agent, or Firm* — Morgan, Lewis & Bockius LLP

(57) ABSTRACT

The present invention provides formulations that achieve effective delivery of methylnaltrexone compositions. The provided formulations are useful for preventing, treating delaying, diminishing or reducing the severity of side effects resulting from use of analgesic opioids.

19 Claims, 5 Drawing Sheets

(56) References Cited

U.S. PATENT DOCUMENTS

| | | |
|---|---|---|
| 4,670,287 A | 6/1987 | Tsuji |
| 4,675,189 A | 6/1987 | Kent et al. |
| 4,689,332 A | 8/1987 | McLaughlin et al. |
| 4,719,215 A | 1/1988 | Goldberg |
| 4,730,048 A | 3/1988 | Portoghese |
| 4,765,978 A | 8/1988 | Abidi et al. |
| 4,806,556 A | 2/1989 | Portoghese |
| 4,824,853 A | 4/1989 | Wals et al. |
| 4,836,212 A | 6/1989 | Schmitt et al. |
| 4,837,214 A | 6/1989 | Tanaka et al. |
| 4,857,833 A | 8/1989 | Gonzalez et al. |
| 4,861,781 A | 8/1989 | Goldberg |
| 4,863,928 A | 9/1989 | Atkinson et al. |
| 4,867,979 A | 9/1989 | Sheth et al. |
| 4,870,084 A | 9/1989 | Eggler et al. |
| 4,883,805 A | 11/1989 | Kasan et al. |
| 4,888,346 A | 12/1989 | Bihari et al. |
| 4,891,379 A | 1/1990 | Zimmerman et al. |
| 4,912,114 A | 3/1990 | Revesz |
| 4,965,269 A | 10/1990 | Brandstrom et al. |
| 4,987,136 A | 1/1991 | Kreek et al. |
| 4,990,342 A | 2/1991 | Wilde |
| 4,990,521 A | 2/1991 | Van Daele et al. |
| 4,999,342 A | 3/1991 | Ahmad et al. |
| 5,102,887 A | 4/1992 | Goldberg |
| 5,116,868 A | 5/1992 | Chen et al. |
| 5,133,974 A | 7/1992 | Paradissis et al. |
| 5,159,081 A | 10/1992 | Cantrell et al. |
| 5,202,159 A | 4/1993 | Chen et al. |
| 5,220,017 A | 6/1993 | Bock et al. |
| 5,236,947 A | 8/1993 | Calvet et al. |
| 5,250,542 A | 10/1993 | Cantrell et al. |
| 5,256,154 A | 10/1993 | Liebert et al. |
| 5,270,328 A | 12/1993 | Cantrell et al. |
| 5,312,899 A | 5/1994 | Schiller |
| 5,358,970 A | 10/1994 | Ruff et al. |
| 5,391,372 A | 2/1995 | Campbell |
| 5,407,686 A | 4/1995 | Patel et al. |
| 5,426,112 A | 6/1995 | Zagon et al. |
| 5,434,171 A | 7/1995 | Frank et al. |
| 5,472,943 A | 12/1995 | Crain et al. |
| 5,512,578 A | 4/1996 | Crain et al. |
| 5,536,507 A | 7/1996 | Abramowitz et al. |
| 5,567,423 A | 10/1996 | Ying |
| 5,585,348 A | 12/1996 | Crain et al. |
| 5,591,433 A | 1/1997 | Michael et al. |
| 5,597,564 A | 1/1997 | Ying |
| 5,609,871 A | 3/1997 | Michael et al. |
| 5,614,219 A | 3/1997 | Wunderlich et al. |
| 5,614,222 A | 3/1997 | Kaplan |
| 5,626,875 A | 5/1997 | Ballester Rodes et al. |
| 5,629,001 A | 5/1997 | Michael et al. |
| 5,656,290 A | 8/1997 | Kelm et al. |
| 5,686,072 A | 11/1997 | Uhr et al. |
| 5,714,586 A | 2/1998 | Kunstmann et al. |
| 5,739,152 A | 4/1998 | Andersson et al. |
| 5,767,125 A | 6/1998 | Crain et al. |
| 5,780,012 A | 7/1998 | Huland et al. |
| 5,804,595 A | 9/1998 | Portoghese et al. |
| 5,811,451 A | 9/1998 | Minoia et al. |
| 5,821,219 A | 10/1998 | Grandy et al. |
| 5,866,154 A | 2/1999 | Bahal et al. |
| 5,866,164 A | 2/1999 | Kuczynski et al. |
| 5,958,452 A | 9/1999 | Oshlack et al. |
| 5,972,954 A | 10/1999 | Foss et al. |
| 5,981,185 A | 11/1999 | Matson et al. |
| RE36,547 E | 2/2000 | Crain et al. |
| 6,025,154 A | 2/2000 | Li et al. |
| 6,096,756 A | 8/2000 | Crain et al. |
| 6,096,763 A | 8/2000 | Hoffman et al. |
| 6,096,764 A | 8/2000 | Bryant et al. |
| 6,099,853 A | 8/2000 | Hertelendy et al. |
| 6,136,780 A | 10/2000 | Zagon et al. |
| 6,143,795 A | 11/2000 | Moschner et al. |
| 6,153,620 A | 11/2000 | Kornetsky |
| 6,190,691 B1 | 2/2001 | Mak |
| 6,194,382 B1 | 2/2001 | Crain et al. |
| 6,261,599 B1 | 7/2001 | Oshlack et al. |
| 6,274,591 B1 | 8/2001 | Foss et al. |
| 6,277,384 B1 | 8/2001 | Kaiko et al. |
| 6,353,004 B1 | 3/2002 | Farrar et al. |
| 6,359,111 B1 | 3/2002 | Meyer et al. |
| 6,362,194 B1 | 3/2002 | Crain et al. |
| 6,384,044 B1 | 5/2002 | Bihari |
| 6,395,705 B2 | 5/2002 | Crain et al. |
| 6,419,959 B1 | 7/2002 | Walter et al. |
| 6,426,094 B2 | 7/2002 | Piver et al. |
| 6,451,806 B2 | 9/2002 | Farrar |
| 6,455,537 B1 | 9/2002 | Cooper |
| 6,469,030 B2 | 10/2002 | Farrar et al. |
| 6,479,500 B1 | 11/2002 | Fukushima et al. |
| 6,559,158 B1 | 5/2003 | Foss et al. |
| 6,608,075 B2 | 8/2003 | Foss et al. |
| 6,693,125 B2 | 2/2004 | Borisy et al. |
| 6,696,066 B2 | 2/2004 | Kaiko et al. |
| 6,720,336 B2 | 4/2004 | Liras |
| 6,723,712 B2 | 4/2004 | Bourhis et al. |
| 6,734,188 B1 | 5/2004 | Rhodes et al. |
| 6,756,364 B2 | 6/2004 | Barbier et al. |
| 6,777,534 B1 | 8/2004 | Klagsbrun et al. |
| 6,794,370 B2 | 9/2004 | Achterrath |
| 6,800,639 B2 | 10/2004 | Giles et al. |
| 6,833,349 B2 | 12/2004 | Xia et al. |
| 6,838,469 B2 | 1/2005 | Sumegi |
| 6,884,879 B1 | 4/2005 | Baca et al. |
| 6,900,234 B1 | 5/2005 | Fossa |
| 6,946,556 B1 | 9/2005 | Likhotvorik et al. |
| 6,960,596 B2 | 11/2005 | Bissery |
| 6,967,016 B2 | 11/2005 | van Gemen et al. |
| 6,984,403 B2 | 1/2006 | Hagen et al. |
| 6,986,901 B2 | 1/2006 | Meisel et al. |
| 6,989,383 B1 | 1/2006 | Rosen et al. |
| 6,992,106 B2 | 1/2006 | Morinaga et al. |
| 7,012,100 B1 | 3/2006 | Edwards et al. |
| 7,074,825 B2 | 7/2006 | Mo et al. |
| 7,094,775 B2 | 8/2006 | Strugnell et al. |
| 7,129,265 B2 | 10/2006 | Mason |
| 7,132,554 B2 | 11/2006 | Rose |
| 7,141,554 B2 | 11/2006 | Rochat et al. |
| 7,160,913 B2 | 1/2007 | Schneider |
| 7,183,269 B2 | 2/2007 | Kreutz |
| 7,196,115 B2 | 3/2007 | Khanuja et al. |
| 7,259,233 B2 | 8/2007 | Dodd et al. |
| 7,312,194 B2 | 12/2007 | Toth et al. |
| 7,501,434 B2 | 3/2009 | Shah et al. |
| 7,563,899 B2 | 7/2009 | Boyd et al. |
| 7,674,904 B2 | 3/2010 | Doshan et al. |
| 8,247,425 B2 | 8/2012 | Bazhina et al. |
| 8,343,992 B2 | 1/2013 | Doshan et al. |
| 8,420,663 B2 | 4/2013 | Bazhina et al. |
| 8,471,022 B2 | 6/2013 | Avey et al. |
| 8,524,276 B2 | 9/2013 | Shah et al. |
| 8,546,418 B2 | 10/2013 | Avey et al. |
| 8,552,025 B2 | 10/2013 | Sanghvi et al. |
| 8,822,490 B2 | 9/2014 | Bazhina et al. |
| 8,853,232 B2 | 10/2014 | Avey et al. |
| 8,916,706 B2 | 12/2014 | Avey et al. |
| 8,946,262 B2 | 2/2015 | Christ et al. |
| 8,956,651 B2 | 2/2015 | Shah et al. |
| 9,102,680 B2 | 8/2015 | Smolenskaya et al. |
| 9,180,125 B2 | 11/2015 | Bazhina et al. |
| 9,314,461 B2 | 4/2016 | Shah et al. |
| 9,492,445 B2 | 11/2016 | Bazhina et al. |
| 9,597,327 B2 | 3/2017 | Doshan et al. |
| 9,669,096 B2 | 6/2017 | Sanghvi et al. |
| 9,724,343 B2 | 8/2017 | Bazhina et al. |
| 9,879,024 B2 | 1/2018 | Smolenskaya et al. |
| 10,307,417 B2 | 6/2019 | Shah et al. |
| 10,376,505 B2 | 8/2019 | Shah et al. |
| 10,376,584 B2 | 8/2019 | Sanghvi et al. |
| 10,507,206 B2 | 12/2019 | Shah et al. |
| 2001/0010919 A1 | 8/2001 | Grandy et al. |
| 2001/0018413 A1 | 8/2001 | Crain et al. |
| 2001/0033865 A1 | 10/2001 | Oshlack et al. |

(56) References Cited

U.S. PATENT DOCUMENTS

| | | |
|---|---|---|
| 2001/0036469 A1 | 11/2001 | Gooberman |
| 2001/0036476 A1 | 11/2001 | Oshlack et al. |
| 2001/0036951 A1 | 11/2001 | Farrar et al. |
| 2001/0046968 A1 | 11/2001 | Zagon et al. |
| 2001/0047005 A1 | 11/2001 | Farrar |
| 2002/0028825 A1 | 3/2002 | Foss et al. |
| 2002/0064771 A1 | 5/2002 | Zhong et al. |
| 2002/0068712 A1 | 6/2002 | Stevens |
| 2002/0173466 A1 | 11/2002 | Crain et al. |
| 2002/0176888 A1 | 11/2002 | Bartholomaeus et al. |
| 2002/0188005 A1 | 12/2002 | Farrar et al. |
| 2003/0018043 A1 | 1/2003 | Cooper |
| 2003/0022909 A1 | 1/2003 | Moss et al. |
| 2003/0026801 A1 | 2/2003 | Weiner et al. |
| 2003/0039689 A1 | 2/2003 | Chen et al. |
| 2003/0065003 A1 | 4/2003 | Foss et al. |
| 2003/0096839 A1 | 5/2003 | Floyd et al. |
| 2003/0105121 A1 | 6/2003 | Bihari |
| 2003/0124086 A1 | 7/2003 | Bentley et al. |
| 2003/0144312 A1 | 7/2003 | Schoenhard |
| 2003/0144510 A1 | 7/2003 | Gala et al. |
| 2003/0158220 A1 | 8/2003 | Foss et al. |
| 2003/0187010 A1 | 10/2003 | Foss et al. |
| 2003/0191147 A1 | 10/2003 | Sherman et al. |
| 2003/0219406 A1 | 11/2003 | Schroit et al. |
| 2003/0229111 A1 | 12/2003 | Oshlack et al. |
| 2004/0010996 A1 | 1/2004 | Karlstrom et al. |
| 2004/0010997 A1 | 1/2004 | Close |
| 2004/0010998 A1 | 1/2004 | Turco |
| 2004/0024006 A1 | 2/2004 | Simon |
| 2004/0136908 A1 | 7/2004 | Olson et al. |
| 2004/0162306 A1 | 8/2004 | Foss et al. |
| 2004/0162307 A1 | 8/2004 | Foss et al. |
| 2004/0162308 A1 | 8/2004 | Foss et al. |
| 2004/0167147 A1 | 8/2004 | Foss et al. |
| 2004/0167148 A1 | 8/2004 | Foss et al. |
| 2004/0180916 A1 | 9/2004 | Levine |
| 2004/0242523 A1 | 12/2004 | Weichselbaum et al. |
| 2004/0254156 A1 | 12/2004 | Le Bourdonnec et al. |
| 2004/0254208 A1 | 12/2004 | Weber et al. |
| 2004/0259898 A1 | 12/2004 | Moss |
| 2004/0259899 A1 | 12/2004 | Sanghvi et al. |
| 2004/0266806 A1 | 12/2004 | Sanghvi et al. |
| 2005/0004029 A1 | 1/2005 | Garcia |
| 2005/0004155 A1 | 1/2005 | Boyd et al. |
| 2005/0011468 A1 | 1/2005 | Moss |
| 2005/0048117 A1 | 3/2005 | Foss et al. |
| 2005/0085514 A1 | 4/2005 | Cosford et al. |
| 2005/0124657 A1 | 6/2005 | Christ et al. |
| 2005/0124885 A1 | 6/2005 | Abend et al. |
| 2005/0187255 A1 | 8/2005 | Lee et al. |
| 2006/0009504 A1 | 1/2006 | Heimbecher et al. |
| 2006/0025592 A1 | 2/2006 | Stranix et al. |
| 2006/0063792 A1 | 3/2006 | Dolle et al. |
| 2006/0094658 A1 | 5/2006 | Currie et al. |
| 2006/0115424 A1 | 6/2006 | Gray |
| 2006/0128742 A1 | 6/2006 | Edwards et al. |
| 2006/0177380 A1 | 8/2006 | Emigh et al. |
| 2006/0204512 A1 | 9/2006 | Krasnoperov et al. |
| 2006/0205753 A1 | 9/2006 | Israel |
| 2006/0258696 A1 | 11/2006 | Moss et al. |
| 2007/0010450 A1 | 1/2007 | Currie et al. |
| 2007/0020261 A1 | 1/2007 | Sliwkowski et al. |
| 2007/0060501 A1 | 3/2007 | Jhamandas et al. |
| 2007/0071761 A1 | 3/2007 | Seon |
| 2007/0082044 A1 | 4/2007 | Yeum |
| 2007/0099946 A1 | 5/2007 | Doshan et al. |
| 2007/0148232 A1 | 6/2007 | Crew et al. |
| 2007/0265293 A1 | 11/2007 | Boyd et al. |
| 2008/0044486 A1 | 2/2008 | Nilsson et al. |
| 2008/0064743 A1 | 3/2008 | Shah et al. |
| 2008/0064744 A1 | 3/2008 | Shah et al. |
| 2008/0070975 A1 | 3/2008 | Shah et al. |
| 2008/0075771 A1 | 3/2008 | Vaughn et al. |
| 2008/0103438 A1 | 5/2008 | Prais et al. |
| 2008/0193531 A1 | 8/2008 | Hermelin et al. |
| 2008/0194611 A1 | 8/2008 | Alverdy et al. |
| 2008/0274119 A1 | 11/2008 | Moss et al. |
| 2009/0312359 A1 | 12/2009 | Foss et al. |
| 2010/0087472 A1 | 4/2010 | Foss et al. |
| 2010/0099699 A1 | 4/2010 | Melucci |
| 2010/0105911 A1 | 4/2010 | Boyd et al. |
| 2010/0120813 A1 | 5/2010 | Bazhina et al. |
| 2010/0249169 A1 | 9/2010 | Shah et al. |
| 2010/0261744 A1 | 10/2010 | Sanghvi et al. |
| 2010/0261745 A1 | 10/2010 | Sanghvi et al. |
| 2010/0261746 A1 | 10/2010 | Sanghvi et al. |
| 2010/0267758 A1 | 10/2010 | Sanghvi et al. |
| 2010/0305323 A1 | 12/2010 | Smolenskaya et al. |
| 2010/0311781 A1 | 12/2010 | Doshan et al. |
| 2012/0059025 A1 | 3/2012 | Shah et al. |
| 2012/0190702 A1 | 7/2012 | Foss et al. |
| 2012/0277260 A1 | 11/2012 | Foss et al. |
| 2013/0317050 A1 | 11/2013 | Bortey |
| 2013/0323286 A1 | 12/2013 | Doshan et al. |
| 2014/0057934 A1 | 2/2014 | Nutalapati |
| 2014/0228389 A1 | 8/2014 | Shah et al. |
| 2014/0235664 A1 | 8/2014 | Sanghvi et al. |
| 2014/0249171 A1 | 9/2014 | Shah et al. |
| 2015/0025100 A1 | 1/2015 | Shah et al. |
| 2015/0057303 A1 | 2/2015 | Doshan et al. |
| 2015/0290187 A1 | 10/2015 | Doshan et al. |
| 2016/0206612 A1 | 7/2016 | Shah et al. |
| 2016/0338946 A1 | 11/2016 | Shah et al. |
| 2017/0143700 A1 | 5/2017 | Doshan et al. |
| 2019/0231771 A1 | 8/2019 | Bortey |
| 2019/0358328 A1 | 11/2019 | Sanghvi et al. |
| 2020/0121673 A1 | 4/2020 | Shah et al. |
| 2020/0179270 A1 | 6/2020 | Shah et al. |
| 2022/0023200 A1 | 1/2022 | Shah et al. |

FOREIGN PATENT DOCUMENTS

| | | |
|---|---|---|
| AU | 199913802 B2 | 3/2003 |
| AU | 2003204844 B2 | 6/2007 |
| BE | 876968 A1 | 10/1979 |
| CA | 2064373 A1 | 9/1992 |
| CA | 1315689 C | 4/1993 |
| CA | 2312234 A1 | 5/1999 |
| CA | 2293008 A1 | 7/2000 |
| CN | 1767831 | 5/2006 |
| CN | 101405031 A | 4/2009 |
| CN | 101845047 A | 9/2010 |
| DE | 3780819 T2 | 1/1993 |
| DE | 4303214 A1 | 8/1994 |
| DE | 19651551 A1 | 6/1998 |
| EP | 0129382 A2 | 12/1984 |
| EP | 0237135 A2 | 9/1987 |
| EP | 0278821 A1 | 8/1988 |
| EP | 0289070 A1 | 11/1988 |
| EP | 0306575 A1 | 3/1989 |
| EP | 0352361 A1 | 1/1990 |
| EP | 0506468 A1 | 9/1992 |
| EP | 0643967 A2 | 3/1995 |
| EP | 0663401 A1 | 7/1995 |
| EP | 0760661 A1 | 3/1997 |
| EP | 0913152 B1 | 5/1999 |
| EP | 0880352 B1 | 11/1999 |
| EP | 0984004 A2 | 3/2000 |
| EP | 1047726 A1 | 11/2000 |
| EP | 1615646 A1 | 1/2006 |
| EP | 2241309 A2 | 10/2010 |
| EP | 2368553 A1 | 9/2011 |
| EP | 2371357 A1 | 10/2011 |
| ES | 2226933 T3 | 4/2005 |
| GB | 1202148 A | 8/1970 |
| GR | 3005834 T3 | 6/1993 |
| JP | S60-1128 A | 1/1985 |
| JP | 1068376 A | 3/1989 |
| JP | 2025427 | 1/1990 |
| JP | 4-183371 | 6/1992 |
| JP | 4-225922 A | 8/1992 |
| JP | 5-213763 | 8/1993 |
| JP | 2625457 B2 | 7/1997 |

(56) References Cited

FOREIGN PATENT DOCUMENTS

| | | |
|---|---|---|
| JP | 2005-531532 A | 10/2005 |
| JP | 2006-522819 A | 10/2006 |
| JP | 2008-542287 A | 11/2008 |
| JP | 4-217924 B2 | 2/2009 |
| JP | 2011-190259 A | 9/2011 |
| NZ | 222911 A | 11/1990 |
| SG | 116167 | 1/2008 |
| SG | 2005064639 | 1/2008 |
| WO | WO-1983/03197 A1 | 9/1983 |
| WO | WO-1988/05297 A1 | 7/1988 |
| WO | WO-1993/20826 A1 | 10/1993 |
| WO | WO-1994/08599 A1 | 4/1994 |
| WO | WO-1994/010202 A1 | 5/1994 |
| WO | WO-1995/31985 A2 | 11/1995 |
| WO | WO-1996/14058 A1 | 5/1996 |
| WO | WO-1996/23793 A1 | 8/1996 |
| WO | WO-1997/07118 A1 | 2/1997 |
| WO | WO-1997/29739 A2 | 8/1997 |
| WO | WO-1997/33566 A2 | 9/1997 |
| WO | WO-1998/25613 A2 | 6/1998 |
| WO | WO-1998/35679 A1 | 8/1998 |
| WO | WO-1998/49185 A1 | 11/1998 |
| WO | WO-1999/22737 A1 | 5/1999 |
| WO | WO-1999/36470 A1 | 7/1999 |
| WO | WO-1999/37681 A2 | 7/1999 |
| WO | WO-1999/40089 A1 | 8/1999 |
| WO | WO-2000/40968 A1 | 7/2000 |
| WO | WO-2000/43507 A1 | 7/2000 |
| WO | WO-2000/46383 A2 | 8/2000 |
| WO | WO-2000/65057 A1 | 11/2000 |
| WO | WO-2001/09300 A2 | 2/2001 |
| WO | WO-2001/13909 A2 | 3/2001 |
| WO | WO-2001/32180 A2 | 5/2001 |
| WO | WO-2001/37785 A2 | 5/2001 |
| WO | WO-2001/41705 A2 | 6/2001 |
| WO | WO-2001/42207 A2 | 6/2001 |
| WO | WO-2001/070031 A1 | 9/2001 |
| WO | WO-2001/85257 A2 | 11/2001 |
| WO | WO-2002/47661 A1 | 6/2002 |
| WO | WO-2002/47685 A2 | 6/2002 |
| WO | WO-2002/060870 A2 | 8/2002 |
| WO | WO-2002/098422 A1 | 12/2002 |
| WO | WO-2003/020296 A1 | 3/2003 |
| WO | WO-2003/032990 A2 | 4/2003 |
| WO | WO-2003/037340 A1 | 5/2003 |
| WO | WO-2003/077867 A2 | 9/2003 |
| WO | WO-2003/086415 A1 | 10/2003 |
| WO | WO-2004/014291 A2 | 2/2004 |
| WO | WO-2004/043964 A2 | 5/2004 |
| WO | WO-2004/080996 A1 | 9/2004 |
| WO | WO-2004/091622 A1 | 10/2004 |
| WO | WO-2004/091623 A1 | 10/2004 |
| WO | WO-2004/091665 A1 | 10/2004 |
| WO | WO-2006/039705 A2 | 4/2006 |
| WO | WO-2006/096626 A2 | 9/2006 |
| WO | WO-2006/127898 A2 | 11/2006 |
| WO | WO-2006/127899 A2 | 11/2006 |
| WO | WO-2006/132963 A2 | 12/2006 |
| WO | WO-2006/135650 A1 | 12/2006 |
| WO | WO-2007/053194 A2 | 5/2007 |
| WO | WO-2007/053698 A2 | 5/2007 |
| WO | WO-2007/131154 A2 | 11/2007 |
| WO | WO-2008/016704 A1 | 2/2008 |
| WO | WO-2008/019115 A2 | 2/2008 |
| WO | WO-2008/021394 A2 | 2/2008 |
| WO | WO-2008/064150 A1 | 5/2008 |
| WO | WO-2008/064351 A2 | 5/2008 |
| WO | WO-2008/064353 A2 | 5/2008 |
| WO | WO-2008/070462 A2 | 6/2008 |
| WO | WO-2008/121348 A2 | 10/2008 |
| WO | WO-2008/121352 A2 | 10/2008 |
| WO | WO-2008/121860 A1 | 10/2008 |
| WO | WO-2009/137086 A1 | 11/2009 |
| WO | WO-2010/039851 A1 | 4/2010 |
| WO | WO-2011/112816 A1 | 9/2011 |
| WO | WO-2020/225395 A1 | 11/2020 |

OTHER PUBLICATIONS

[No Author Listed] Endogenous opioids. http://opioids.com/opiates.html 3 pages. Last accessed May 4, 2015.

[No Author Listed] European Medicines Agency, Impurities in New Drug Substances, Oct. 2006; 15 pages.

[No Author Listed] Mallinckrodt Pharmaceuticals, Methylnaltrexone Bromide, Product Specifications Effective Mar. 2014; 1 page.

[No Author Listed] Mallinckrodt Pharmaceuticals, Methylnaltrexone Bromide, Technical Package 2014; 3 pages.

[No Author Listed] Methylnaltrexone: MNTX. Drugs R D. 2006;7(6):374-8.

[No Author Listed] Monograph for Naltrexone, U.S. Pharmacopeia USP 29, NF 24, 2006; pp. 1476-1478, 2556-2557.

[No Author Listed] Pain management; cancer-pain remedy wins orphan drug status. Cancer Biotechnology Weekly. Aug. 12, 1996; 2 pages.

[No Author Listed] Pathophysiology. Medscape General Medicine. 2005;7(3): 17. http://www.medscape.com/viewarticle/506798_5, 3 pages.

[No Author Listed] Positive Results from Phase 3 Clinical Study of Methylnaltrexone Treatment for Opioid-Induced Constipation Presented at Digestive Disease Week Conference, May 23, 2006 (http://files.shareholder.com/downloads/PGNX/0x0x40529/bfba0030-5977-4a52-b228-91ae6b7daf8b/198253.pdf).

[No Author Listed] Prefilled Syringes: The Trend for Growth Strengthens. OndrugDelivery. 32 pages, (2006).

[No Author Listed] Progenics achieves enrollment target in pivotal phase 3 clinical trial of methylnaltrexone for opioid-induced constipation. Press Release. Progenics Pharmaceuticals. Dec. 3, 2004.

[No Author Listed] Progenics announces positive top-line results from pivotal phase 3 clinical trial of MNTX in opioid-induced constipation. Press Release. Progenics Pharmaceuticals, Inc. Mar. 10, 2005.

[No Author Listed] Progenics initiates second phase 3 clinical trial of methylnaltrexone in opioid-induced constipation. Press Release. Progenics Pharmaceuticals, Inc. Jan. 13, 2004.

[No Author Listed] Progenics Pharmaceuticals Reports Second Quarter 2008 Results. Business Wire Aug. 8, 2008.

[No Author Listed] Relistor® Prescribing Information. Wyeth and Progenics Apr. 2008.

[No Author Listed] Remington's Pharmaceutical Sciences (1985), pp. 187-189, 257, 1102, 1106-1107, 1493, 1523.

[No Author Listed] Remington's Pharmaceutical Sciences. 15th Edition. 1995: 201-02, 273-74, 1466, 1614-5.

[No Author Listed] Remington's Pharmaceutical Sciences. 19th Edition. 1995: 278-79, 283-84.

[No Author Listed] Remington's Pharmaceutical Sciences. 19th Edition. 1995: 640, 643 and 1458.

[No Author Listed] Remington's, The Science and Practice of Pharmacy, 19th Edition. Mack Publishing Company, 1995; pp. 639-647 and 1447-1462.

[No Author Listed] Remington's, The Science and Practice of Pharmacy, 19th Edition. Mack Publishing Company, 1995; vol. II: p. 1486.

[No Author Listed] Remington, The Science and Practice of Pharmacy, 19th Edition. Mack Publishing Company, 1995; pp. 1462 and 1496.

[No Author Listed] Remington: The Science and Practice of Pharmacy, 19th edition. Philadelphia College of Pharmacy and Science 1995.

[No Author Listed] The Merck Manual. 17th edition. 1999:312-315.

About Relistor, Do You Have Painstipation? Retrieved online at: https://www.relistor.com/about-relistor. 1 page, (2012).

About Relistor, Patient Resources. Retrieved online at: https://www.relistor.com/patient-resources. 1 page, (2013).

Ahlawat et al., The Secret of our Successful Drug Launces. McKinsey & Company, Pharmaceuticals & Medical Products. Retrieved online

(56) References Cited

OTHER PUBLICATIONS at: https://www.mckinsey.com/industries/pharmaceuticals-and-medical-products/our-insights/the-secret-of-successful-drug-launches. 2 pages, Mar. 2014.

Akinbami et al., Effect of a peripheral and a central acting opioid antagonist on the testicular response to stress in rats. Neuroendocrinology. Apr. 1994;59(4):343-8.

Altier et al., Opioid receptors in the ventral tegmental area contribute to stress-induced analgesia in the formalin test for tonic pain. Brain Res. Apr. 29, 1996;718(1-2):203-6.

Amin et al., Efficacy of methylnaltrexone versus naloxone for reversal of morphine-induced depression of hypoxic ventilatory response. Anesth Analg. Apr. 1994;78(4):701-5.

Amir et al., Endorphins in endotoxin-induced hyperglycemia in mice. Arch Toxicol Suppl. 1983;6:261-5.

Amir, Naloxone improves, and morphine exacerbates, experimental shock induced by release of endogenous histamine by compound 48/80. Brain Res. Apr. 9, 1984;297(1): 187-90.

Amitiza, Highlights of Prescribing Information, Initial U.S. Approval 2006. Package Insert, 19 pages, Revised Apr. 2013.

Anderberg et al., Epithelial transport of drugs in cell culture. VIII: Effects of sodium dodecyl sulfate on cell membrane and tight junction permeability in human intestinal epithelial (Caco-2) cells. J Pharm Sci. Apr. 1993;82(4):392-8.

Ansel et al., General Principles of Drug Absorption. Pharmaceutical Dosage Forms and Drug Delivery Systems. Fifth Edition, Lea & Febiger, Philadelphia. pp. 53-55, (1990).

Arendt et al., Bidirectional effects of endogenous opioid peptides on endothelin release rates in porcine aortic endothelial cell culture: mediation by delta opioid receptor and opioid receptor antagonist-insensitive mechanisms. J Pharmacol Exp Ther. Jan. 1995;272(1):1-7.

Arerangaiah et al., Opioids induce renal abnormalities in tumor-bearing mice. Nephron Exp Nephrol. 2007;105(3):e80-9. Epub Jan. 12, 2007.

Argentieri et al., Interaction of the opiate antagonist, naltrexone methyl bromide, with the acetylcholine receptor system of the motor end-plate. Brain Res. Oct. 31, 1983:277(2):377-9.

Armstead, Relationship among NO, the KATP channel, and opioids in hypoxic pial artery dilation. Am J Physiol. Sep. 1998;275(3 Pt 2):H988-94.

Armstrong et al., The gastrointestinal activity and peripheral selectivity of alvimopan, ADL08-0011, and naloxone in mice. May 21, 2006 DDW Presentation in Los Angeles. Clincial Phar Therap. 2005;77:74. Abstract #221957.

Attali et al., Kappa opiate agonists inhibit Ca2+ influx in rat spinal cord-dorsal root ganglion cocultures. Involvement of a GTP-binding protein. J Biol Chem. Jan. 5, 1989;264(1):347-53.

Aung et al., Methylnaltrexone prevents morphine-induced kaolin intake in the rat. Life Sci. Apr. 16, 2004;74(22):2685-91.

Aung et al., Scutellaria baicalensis decreases ritonavir-induced nausea. AIDS Res Ther. Dec. 20, 2005;2:12, 6 pages.

Aungst, Intestinal Permeation Enhancers. Journal of Pharmaceutical Sciences. Apr. 2000;89(4):429-442.

Aungst, Novel Formulation Strategies for Improving Oral Bioavailability of Drugs with Poor Membrane Permeation or Presystemic Metabolism. Journal of Pharmaceutical Sciences. Oct. 1993;82(10):979-987.

Bagnol et al., Changes in enkephalin immunoreactivity of sympathetic ganglia and digestive; tract of the cat after splanchnic nerve ligation. Regul Pept. Sep. 22, 1993;47(3):259-73. Abstract; Only.

Baka et al., Study of equilibrium solubility measurement by saturation shake-flask method using hydrochlorothiazide as model compound. J Pharm Biomed Anal. Jan. 22, 2008;46(2):335-41.

Baker et al., Functional effects of systemically administered agonists and antagonists of mu, delta, and kappa opioid receptor subtypes on body temperature in mice. J Pharmacol Exp Ther. Sep. 2002;302(3):1253-64.

Balasubramanian et al., Morphine sulfate inhibits hypoxia-induced vascular endothelial growth factor expression in endothelial cells and cardiac myocytes. J Mol Cell Cardiol. Dec. 2001;33(12):2179-87.

Balls, Concerning Pseudomorphine. J Biol Chem. 1927;71:537-542.

Baratti et al., Brain opioid peptides may participate in the reversal of pentylenetetrazol-induced amnesia. Methods Find Exp Clin Pharmacol. Sep. 1990; 12(7):451-6.

Barbee et al., Management of Opioid-Induced Constipation. Pharmacy Times, retrieved online at: https://www.pharmacytimes.com/publications/health-system-edition/2016/september2016/management-of-opioid-induced-constipation. 4 pages, Sep. 23, 2016.

Basilisco el al., Effect of loperamide and naloxone on mouth-to-caecum transit time evaluated by lactulose hydrogen breath test. Gut. Jul. 1985;26(7):700-3.

Basilisco et al., Oral naloxone antagonizes loperamide-induced delay of orocecal transit. Dig Dis Sci. Aug. 1987;32(8):829-32.

Bastin et al., Salt Selection and Optimisation for Pharmaceutical New Chemical Entities. Organic Process Research & Development. 2000;4:427-435.

Bauer, Lehrbuch der pharmazeutischen Technologie: mit einer Einfuhrung in die Biopharmazie. Wissenschaftliche Verlagsgesellschaft mbH Stuttgart. p. 240, (2002).

Bausch Health, Valeant and Progenics Announce FDA Approves Relistor® Tablets for the Treatment of Opioid-Induced Constipation in Adults with Chronic Non-cancer Pain. Press release, retrieved online at: https://ir.bauschhealth.com/news-releases/2016/07-19-2016-230453094. 4 pages, Jul. 19, 2016.

Beattie et al., The in vitro pharmacology of the peripherally restricted opioid receptor antagonists, alvimopan, ADL 08-0011 and methylnaltrexone. Naunyn Schmiedebergs Arch Pharmacol. May 2007;375(3):205-20.

Bedingfield el al., Methylnaltrexone attenuates taste aversion conditioned by low-dose ethanol. Alcohol. Jan. 1998; 15(1):51-4.

Belcheva et al., µ opioid transactivation and down-regulation of the epidermal growth factor receptor in astrocytes: implications for mitogen-activated protein kinase signaling. Mol Pharmacol. Dec. 2003;64(6):1391-401.

Belcheva et al., µ-opioid receptor-mediated ERK activation involves calmodulin-dependent epidermal growth factor receptor transactivation. J Biol Chem. Sep. 7, 2001:276(36):33847-53. Epub Jul. 16, 2001.

Berge et al., Pharmaceutical Salts. Journal of Pharmaceutical Sciences. 1977;66(1):1-19.

Bertschy, Methadone maintenance treatment: an update. Eur Arch Psychiatry Clin Neurosci. 1995;245(2):114-24.

Bhatt et al., Cleavage of Ethers. Synthesis. 1983;1983(4):249-282.

Bianchi et al., Quaternary narcotic antagonists' relative ability to prevent antinociception and gastrointestinal transit inhibition in morphine-treated rats as an index of peripheral selectivity. Life Sci. May 31, 1982;30(22):1875-83.

Bickel, Stimulation of colonic motility in dogs and rats by an enkephalin analogue pentapeptide. Life Sci. 1983;33 Suppl 1:469-72.

Bigliardi et al., Different expression of mu-opiate receptor in chronic and acute wounds and the effect of beta-endorphin on transforming growth factor beta type II receptor and cytokeratin 16 expression. J Invest Dermatol. Jan. 2003;120(1):145-52.

Bigliardi-Qi et al., Changes of epidermal mu-opiate receptor expression and nerve endings in chronic atopic dermatitis. Dermatology. 2005;210(2):91-9.

Binder et al., Effect of the peripherally selective kappa-opioid agonist, asimadoline, on adjuvant arthritis. Br J Pharmacol. Jun. 1998;124(4):647-54.

Bianchetti et al., Quaternary derivatives of narcotic antagonists: stereochemical requirements at the chiral nitrogen for in vitro and in vivo activity. Life Sci. 1983;33 Suppl 1:415-8.

Blank et al., Central, stereoselective receptors mediate the acute effects of opiate antagonists on luteinizing hormone secretion. Life Sci. Oct. 27, 1986;39(17):1493-99.

(56) References Cited

OTHER PUBLICATIONS

Blebea et al., Differential effects of vascular growth factors on arterial and venous angiogenesis. J Vasc Surg. Mar. 2002;35(3):532-8.
Blebea et al., Opioid growth factor modulates angiogenesis. J Vasc Surg. Aug. 2000;32(2):364-73.
Bond et al., Investigation of small bowel transit time in man utilizing pulmonary hydrogen (H2) measurements. J Lab Clin Med. Apr. 1975;85(4):546-55. Abstract Only.
Bonn, Morphine stimulates tumour growth. Lancet Oncol. Sep. 2002;3(9):520.
Boonstra et al., Engineering novel biocatalytic routes for production of semisynthetic opiate drugs. Biomol Eng. Sep. 2001;18(2):41-7.
Bouchard et al., The Apparent Lipophilicity of Ammonium Ions is Influenced by Galvani Potential Difference, Not Ion Pairing: A Cyclic Voltammetry Study. Pharmaceutical Research. 2001;18(5):702-708.
Bowen et al., Antagonism of the antinociceptive and discriminative stimulus effects of heroin and morphine by 3-methoxynaltrexone and naltrexone in rhesus monkeys. J Pharmacol Exp Ther. Jul. 2002;302(1):264-73.
Bowen et al., Behavioral Pharmacology of Opoid Antagonists with Limited Access Across the Blood-brain Barrier. Drug and Alcohol Dependence. 2002;66:S19, Abstract 65.
Breitbart et al., Control of non-pain symptoms in HIV/AIDS. J Back Musculoskelet Rehabil. 1997;8(3):243-46.
Brix-Christensen et al., Endogenous morphine is produced in response to cardiopulmonary bypass in neonatal pigs. Acta Anaesthesiol Scand. Nov. 2000;44(10): 1204-8.
Brix-Christensen et al., Endogenous morphine levels increase following cardiac surgery as part of the anti-inflammatory response? Int J Cardiol. Dec. 19, 1997;62(3): 191-7.
Broadhead, Parenteral Dosage Form. Pharmaceutical Preformulation and Formulation (M. Gibson, ed.). pp. 331-354, (2001).
Brondsted et al., Hydrogels for site-specific drug delivery to the colon:degradation. Pharm Res. Dec. 1992;9(12):1540-5. Abstract Only.
Brown et al., Techniques for mechanical stimulation of cells in vitro: a review. J Biomech. Jan. 2000;33(1):3-14.
Brown et al., The use of quaternary narcotic antagonists in opiate research. Neuropharmacology. Mar. 1985;24(3):181-91.
Brown et al., Opiate antagonists: central sites of action in suppressing water intake of the rat. Brain Res. Sep. 28, 1981;221(2):432-6.
Brown et al., Reversal of morphine-induced catalepsy in the rat by narcotic antagonists and their quaternary derivatives. Neuropharmacology. Mar. 1983;22(3):317-21.
Bruce et al., Microbial degradation of the morphine alkaloids: identification of morphine as an intermediate in the metabolism of morphine by Pseudomonas putida M10. Arch Microbiol. 1990;154(5):465-70.
Bruley-Des-Varannes et al, Cholécystokine et ses antagonistes: effets sur la motricité digestive. Gastroenterol Clin Biol. 1991;15:744-57. French.
Bundgaard et al., (C) Means to Enhance Penetration. (1) Prodrugs as a means to improve the delivery of peptide drugs. J Drug Delivery Rev. 1992;8:1-38.
Burkhart et al., Metkephamid (Tyr-D-Ala-Gly-Phe-N(Me)Met$_{NH2}$), a Potent Opioid Peptide: Receptor Binding and Analgesic Properties. Peptides. 1982;3:869-71.
Burks et al., Regulation of gastrointestinal function by multiple opioid receptors. Life Sci. 1988;43(26):2177-81.
Business Wire, (Press Release) Progenics Pharmaceuticals Reports Second Quarter 2008 Results. http://www.progenics.com. 5 pages, Aug. 8, 2008.
Business Wire, Progenics and Wyeth Announce FDA Has Approved RELISTOR. Progenics Pharmaceuticals, Retrieved online at: https://www.businesswire.com/news/home/20080424006635/en/Progenics-Wyeth-AnnounceFDA-Approved-RELISTOR. 4 pages, Apr. 24, 2008.
Business Wire, Progenics Announces Approvals of New Ready-to-Use Pre-Filled Syringes for RELISTOR in U.S., E.U. and Canada. Progenics Pharmaceuticals, Retrieved online at: https://ir.progenics.com/static-files/f8316ebe-3266-432f-ac43-f10a26ab6efc. 3 pages, Sep. 29, 2010.
Business Wire, Progenics Pharmaceuticals and Salix Pharmaceuticals Announce Worldwide License Agreement for RELISTOR®, Retrieved online at: https://www.businesswire.com/news/home/20110207005819/en/Progenics-PharmaceuticalsSalix-Pharmaceuticals-Announce-Worldwide-License. 5 pages, Feb. 7, 2011.
BusinessWire, Wyeth and Progenics Pharmaceuticals Announce Worldwide Collaboration to Develop and Commercialize Methylnaltrexone; Methylnaltrexone in Late-Stage Clinical Development for Opioid-Induced Constipation and Post-Operative Bowel Dysfunction. Progenics Pharmaceuticals, Inc. Press Release, 4 pages, Dec. 23, 2005.
Bös et al., A Short and Efficient Synthesis of C-Nor-Dihydrocodeinone—The Antipode of Goto's Sinomenilone. Heterocycles. 1983;20(6): 1077-81.
Caballero-Hernandez et al., Potentiation of rat lymphocyte proliferation by novel non-peptidic synthetic opioids. Int Immunopharmacol. Jul. 2005;5(7-8):1271-8. Epub Apr. 12, 2005.
Cadet et al., Differential expression of the human mu opiate receptor from different primary vascular endothelial cells. Med Sci Monit. Oct. 2004; 10(10):BR351-5. Epub Sep. 23, 2004.
Cadet et al., Molecular identification and functional expression of mu 3, a novel alternatively spliced variant of the human mu opiate receptor gene. J Immunol. May 15, 2003;170(10):5118-23.
Calcagnetti et al., Quaternary naltrexone reveals the central mediation of conditional opioid analgesia. Pharmacol Biochem Behav. Jul. 1987;27(3):529-31.
Camilleri et al., Opioids in Gastroenterology: Treating Adverse Effects and Creating Therapeutic Benefits. Clin Gastroenterol Hepatol. Sep. 2017;15(9):1338-1349.
Cao et al., Cardioprotection of interleukin-2 is mediated via kappa-opioid receptors. J Pharmacol Exp Ther. May 2004;309(2):560-7. Epub Jan. 27, 2004.
Carmeliet et al., Angiogenesis in cancer and other diseases. Nature. Sep. 14, 2000;407(6801):249-57.
Carr et al., Naltrexone antagonizes the analgesic and immunosuppressive effects of morphine in mice. J Pharmacol Exp Ther. May 1994;269(2):693-8.
CAS Registry No. 75232-52-7, Methylnaltrexone Bromide. Mallinckrodt Pharmaceuticals. 1 page, Mar. 2014.
Cavallito et al., Modification of rates of gastrointestinal absorption of drugs. II. Quaternary ammonium salts. J Am Pharm Assoc Am Pharm Assoc. Mar. 1958;47(3, Part 1):169-73.
Center for Drug Evaluation and Research (CDER), Guidance for Industry, Immediate Release Solid Oral Dosage Forms. Scale-Up and Postapproval Changes: Chemistry, Manufacturing, and Controls, In Vitro Dissolution Testing, and In Vivo Bioequivalence Documentation. 30 pages, Nov. 1995.
Center for Drug Evaluation and Research, Application No. 21-964, Labeling. Highlights of Prescribing Information, Relistor (methylnaltrexone bromide) Subcutaneous Injection. 53 pages, (2008).
Center for Drug Evaluation and Research, *Inactive Ingredients*, Food and Drug Administration, https://web.archive.org/web/20081023182144/http;/www.fda.gov/cder/iig/IIG-download.htm. 185 pages.
Certified U.S. Appl. No. 60/461,611, filed Apr. 8, 2003.
Chambliss, Enteric Coatings. Encyclopedia of Pharmaceutical Technology. Marcel Dekker, Inc., New York, James Swarbrick (Ed.). pp. 189-200, (1992).
Chang et al., An antiabsorptive basis for precipitated withdrawal diarrhea in morphine-dependent rats. J Pharmacol Exp Ther. Feb. 1984;228(2):364-9.
Chang et al., The association between opiates and cytokines in disease. Adv Exp Med Biol. 1998;437:4-6.
Chatterjie et al., Stereospecific synthesis of the 6beta-hydroxy metabolites of naltrexone and naloxone. J Med Chem. May 1975;18(5):490-2. Abstract Only.

(56) References Cited

OTHER PUBLICATIONS

Chen et al., Morphine stimulates vascular endothelial growth factor-like signaling in mouse retinal endothelial cells. Curr Neurovasc Res. Aug. 2006;3(3):171-80.
Chinese Office Action for Application No. 201710321015.1, dated Jan. 19, 2021, 17 pages.
Choi et al., Inhibition of chemokine-induced chemotaxis of monkey leukocytes by mu-opioid receptor agonists. In Vivo. Sep.-Oct. 1999; 13(5):389-96.
Choi et al., Opioid antagonists: a review of their role in palliative care, focusing on use in opioid-related constipation. J Pain Symptom Manage. Jul. 2002;24(1):71-90. Review.
Clayden et al., Hydrocarbon frameworks. Organic Chemistry. Oxford University Press, Oxford. pp. 26-35, (2001).
Collins et al., Peak plasma concentrations after oral morphine: a systematic review. J Pain Symptom Manage. Dec. 1998;16(6):388-402.
Cone et al., The identification and measurement of two new metabolites of naltrexone in human urine. Res Commun Chem Pathol Pharmacol. Jun. 1978;20(3):413-33. Abstract Only.
Corrigall et al., Antagonist treatment in nucleus accumbens or periaqueductal grey affects heroin self-administration. Pharmacol Biochem Behav. Jun. 1988;30(2):443-50.
Corrigall, Heroin self-administration: effects of antagonist treatment in lateral hypothalamus. Pharmacol Biochem Behav. Aug. 1987;27(4):693-700.
Cozzolino et al., Acute effects of beta-endorphin on cardiovascular function in patients with mild to moderate chronic heart failure. Am Heart J. Sep. 2004; 148(3):E1-7.
Crockett et al., American Gastroenterological Association Institute Guideline on the Medical Management of Opioid-Induced Constipation. Gastroenterology. 2019;156:218-226.
Crockett, Opioid-Induced Constipation (OIC) Guideline_ Gastroenterology. 2019;156:228.
Culpepper-Morgan et al., Treatment of opioid-induced constipation with oral naloxone: a pilot study. Clin Pharmacol Ther. Jul. 1992;52(1):90-5. Abstract Only.
D'Amato et al., Studies of three non-peptide cholecystokinin antagonists (devazepide, lorglumide and loxiglumide) in human isolated alimentary muscle and guinea-pig ileum. Br J Pharmacol. Feb. 1991;102(2):391-5.
Dajani et al., Effects of E prostaglandins, diphenoxylate and morphine on intestinal motility in vivo. Eur J Pharmacol. Nov. 1975;34(1):105-13. Abstract Only.
Dajani et al., The pharmacology of SC-27166: a novel antidiarrheal agent. J Pharmacol Exp Ther. Dec. 1977;203(3):512-26. Abstract Only.
Daniel et al., Effects of morphine and other drugs on motility of the terminal ileum. Gastroenterology. Apr. 1959;36(4):510-23.
De Ponti et al., Methylnaltrexone Progenics. Curr Opin Investig Drugs. Apr. 2002;3(4):614-20. Review.
De Schryver et al., New developments in the treatment of irritable bowel syndrome. Scand J Gastroenterol Suppl. 2000;35(232):38-42.
Doherty et al., Route-dependent metabolism of morphine in the vascularly perfused rat small intestine preparation. Pharm Res. Mar. 2000; 17(3):291-8.
Dragonetti et al., Levallorphan methyl iodide (SR 58002), a potent narcotic antagonist with peripheral selectivity superior to that of other quaternary compounds. Life Sci. 1983;33 Suppl 1:477-80.
Drug Information System, Sodium Lauryl Sulphate. Retrieved online at: http://www.druginfosys.com/drug.aspx?drugcode=1267 &type=1. 5 pages. 2002-2016.
Egan et al., Prospective pharmacokinetic and pharmacodynamic validation of propofol's context sensitive T1/2. Anesthesiology. Sep. 1999;91(3A): Abstract A347.
Eisenberg, Effects of naltrexone on plasma corticosterone in opiate-naïve rats: a central action. Life Sci. Mar. 19, 1984;34(12):1185-91.
Eisenstein et al., Effect of opioids on oral *Salmonella* infection and immune function. Adv Exp Med Biol. 2001;493:169-76.

El-Tawil, Persistence of Abdominal Symptoms after Successful Surgery for Idiopathic Slow Transit Constipation. Southern Medical Journal. 2002;95(9); 1042-1046. http://www.medscape.com/viewarticle/442893_4, 2 pages. Last accessed Jul. 14, 2009.
Emea, ICH Topic Q 3 A (R2), Impurities in new Drug Substances. European Medicines Agency. CPMP/ICH/2737/99, 10 pages, Oct. 2006.
Entereg, Highlights of Prescribing Information, Initial U.S. Approval 2008. Package Insert, 19 pages, Revised Oct. 2013.
Epstein et al., Naltrexone attenuates acute cigarette smoking behavior. Pharmacol Biochem Behav. Jan. 2004;77(1):29-37.
Farooqui et al., µ opioid receptor stimulates a growth promoting and pro-angiogenic tumor microenvironment. Proc Amer Assoc Cancer Res. 2005;46. AACR Meeting Abstract, Abstract #4650.
Farooqui et al., Naloxone acts as an antagonist of estrogen receptor activity in MCF-7 cells. Mol Cancer Ther. Mar. 2006;5(3):611-20.
Farthing et al., New drugs in the management of the irritable bowel syndrome. Drugs. Jul. 1998;56(1):11-21.
Farup et al., The Symptomatic Effect of Cisapride in Patients with Irritable Bowel Syndrome and Constipation. Scand J Gastronenerol. 1998;33:28-31.
Faura et al., Systematic review of factors affecting the ratios of morphine and its major metabolites. Pain. Jan. 1998;74(1):43-53.
Fawcett et al., Formulation and stability of naltrexone oral liquid for rapid withdrawal from methadone. Ann Pharmacother. Nov. 1997;31(11):1291-5.
FDA, Joint meeting of the anesthetic and analgesic drug products advisory committee (AADPAC) and the Drug Safety and Risk Management Advisory Committee (DSaRM). Retrieved online at: https://www.fda.gov/downloads/AdvisoryCommittees/CommitteesMeetingMaterials/Drugs/AnestheticAndAnalgesicDrugProductsAdvisoryCommittee/UCM564514.pdf. 241 pages, Apr. 5, 2017.
FDA, U.S. Food & Drug Administration, FDA Drug Safety Communication: FDA strengthens warning that non-aspirin nonsteroidal anti-inflammatory drugs (NSAIDs) can cause heart attacks or strokes. Retrieved online at: https://www.fda.gov/Drugs/DrugSafety/ucm451800.htm. 2 pages, Jul. 9, 2015.
FDA.gov, Drugs@FDA: FDA Approved Drug Products, Amitiza. Retrieved online at: https://www.accessdata.fda.gov/scripts/cder/daf/index.cfm?event=overview.process&ApplNo=021908, 2 pages.
FDA.gov, Drugs@FDA: FDA Approved Drug Products, Entereg. Retrieved online at: https://www.accessdata.fda.gov/scripts/cder/daf/index.cfm?event=overview.process&ApplNo=021775, 2 pages.
FDA.gov, Drugs@FDA: FDA Approved Drug Products, Movantik. Retrieved online at: https://www.accessdata.fda.gov/scripts/cder/daf/index.cfm?event=overview.process&ApplNo=204760, 2 pages.
FDA.gov, Drugs@FDA: FDA Approved Drug Products, Relistor. Retrieved online at: https://www.accessdata.fda.gov/scripts/cder/daf/index.cfm?event=overview.process&ApplNo=021964. 2 pages.
FDA.gov, Drugs@FDA: FDA Approved Drug Products, Symproic. Retrieved online at: https://www.accessdata.fda.gov/scripts/cder/daf/index.cfm?event=overview.process&ApplNo=208854, 2 pages.
Fecho et al., Assessment of the involvement of central nervous system and peripheral opioid receptors in the immunomodulatory effects of acute morphine treatment in rats. J Pharmacol Exp Ther. Feb. 1996;276(2):626-36.
Feltkamp et al., Pharmazeutische Qualitatskontrolle. Georg Thieme Verlag Stuttgart. pp. 502-504, Feb. 1983.
Fernandez-Tome et al., Interaction between opioid agonists or naloxone and 5-HTP on feeding behavior in food-deprived rats. Pharmacol Biochem Behav. Feb. 1988;29(2):387-92.
Fingl et al., Laxatives and Cathartics. Pharmacological Basis of Therapeutics. Chapter 43, pp. 1002-1005, (1980).
Finn et al., Endocytosis of the mu opioid receptor reduces tolerance and a cellular hallmark of opiate withdrawal. Neuron. Dec. 6, 2001;32(5):829-39.
Flores et al., Mechanisms of morphine-induced immunosuppression: effect of acute morphine administration on lymphocyte trafficking. J Pharmacol Exp Ther. Mar. 1995;272(3): 1246-51.
Foss et al., Dose-related antagonism of the emetic effect of morphine by methylnaltrexone in dogs. J Clin Pharmacol. Aug. 1993;33(8):747-51.

(56) References Cited

OTHER PUBLICATIONS

Foss et al., Methylnaltrexone reduces morphine-induced postoperative emesis by 30%. Anesth Analg. 1994;78:S119.

Foss et al., Prevention of apomorphine- or cisplatin-induced emesis in the dog by a combination of methylnaltrexone and morphine. Cancer Chemother Pharmacol. 1998;42(4):287-91.

Foss et al., Subcutaneous methylnaltrexone reduces morphine-induced subjective effects in humans. Anesthesiology. 2001;95. Abstract A-817.

Foss et al., Alvimopan (Entereg™), a novel opioid antagonist, achieves active systemic concentrations. Clinical Pharmacology & Therapeutics. Feb. 2005;p. P74:Abstract PII-90.

Foss et al., Effects of methylnaltrexone on morphine-induced cough suppression in guinea pigs. Life Sci. 1996;59(15):PL235-8.

Foss et al., Enteric-coated methylnaltrexone prevents opioid-induced oral-cecal transit delay in humans. Anesth Analg. 2000;90. Abstract S409.

Foss et al., Methylnaltrexone does not antagonize the analgesic effect of morphine: a clinical study. 1995 Annual scientific meeting of the American Society of Anesthesiologists. Atlanta, Georgia, Oct. 21-25, 1995. Abstracts. Anesthesiology. Sep. 1995;83(3A Suppl):A361.

Foss et al., Safety and tolerance of methylnaltrexone in healthy humans: a randomized, placebo-controlled, intravenous, ascending-dose, pharmacokinetic study. J Clin Pharmacol. Jan. 1997;37(1):25-30.

Foss et al., The efficacy or oral methylnaltrexone in decreasing the subjective effects of IV morphine. Anesth Analg. 1997;84. Abstract S484.

Foss, A review of the potential role of methylnaltrexone in opioid bowel dysfunction. Am J Surg. Nov. 2001; 182(5A Suppl):19S-26S.

Fox et al., Roles of central and peripheral mu, delta and kappa opioid receptors in the mediation of gastric acid secretory effects in the rat. J Pharmacol Exp Ther. Feb. 1988;244(2):456-62.

France et al., Morphine, saline and naltrexone discrimination in morphine-treated pigeons. J Pharm and Exper Ther. 1987;242:195-202.

France et al., Comparison of naltrexone and quaternary naltrexone after systemic and intracerebroventricular administration in pigeons. Neuropharmacology. Jun. 1987;26(6):541-8.

France et al., Intracerebroventricular drug administration in pigeons. Pharmacol Biochem Behav. Nov. 1985;23(5):731-6.

Fransen et al., Physicochemical interactions between drugs and superdisintegrants. J Pharm Pharmacol. Dec. 2008;60(12):1583-9.

Fraser et al., Methods for evaluating addiction liability. (A) "Attitude" of opiate addicts toward opiate-like drugs. (B) a short-term "direct" addiction test. J Pharmacol Exp Ther. Sep. 1961;133:371-87. Abstract Only.

Frederickson et al., Metkephamid, a Systemically Active Analog of Methionine Enkephalin with Potent Opioid δ-Receptor Activity. Science. 1991;211:603-05.

French et al., Purification and characterization of morphinone reductase from Pseudomonas putida M10. Biochem J. Jul. 1, 1994;301 ( Pt 1):97-103.

Friedman et al., Opioid antagonists in the treatment of opioid-induced constipation and pruritus. Ann Pharmacother. Jan. 2001;35(1):85-91.

Frässdorf et al., Morphine induces late cardioprotection in rat hearts in vivo: the involvement of opioid receptors and nuclear transcription factor kappaB. Anesth Analg. Oct. 2005;101(4):934-41.

Funke et al., A $^1$H and $^{13}$C nuclear magnetic resonance study of three quaternary salts of naloxone and oxymorphone. J Chem Soc. 1986:735-8.

Galligan et al., Centrally mediated inhibition of small intestinal transit and motility by morphine in the rat. J Pharmacol Exp Ther. Aug. 1983;226(2):356-61. Abstract Only.

Gan et al., Consensus guidelines for managing postoperative nausea and vomiting. Anesth Analg. Jul. 2003;97(1):62-71.

Gennaro, Remington: The Science and Practice of Pharmace, vol. I. Mack Publishing Company, Pennsylvania. Chapter 14, pp. 182-183, (1995).

Gervitz, Targeted approach: methylnaltrexone blocks opioid-induced constipation and other peripheral side effects. Topics in Pain Management. 2005;21(1):6-8. Quiz on p. 11.

Giles et al., Quaternary opiate antagonists lower blood pressure and inhibit leucine- enkephalin responses. Eur J Pharmacol. Nov. 25, 1983;95(3-4):247-52.

Gmerek et al., Independent central and peripheral mediation of morphine-induced inhibition of gastrointestinal transit in rats. J Pharmacol Exp Ther. Jan. 1986;236(1):8-13.

Gordon et al., The effect of aging on the dissolution of wet granulated tablets containing super disintegrants. International Journal of Pharmaceutics. Aug. 1993;97(1-3):119-131.

Goumon et al., *Ascaris suum*, an intestinal parasite, produces morphine. J Immunol. Jul. 1, 2000; 165(1):339-43.

Green, Comparative effects of analgesics on pain threshold, respiratory frequency and gastrointestinal propulsion. Br J Pharmacol Chemother. Mar. 1959;14(1):26-34.

Grigoriev et al., Clinical gastroenterology. Ministry of Health of the Russian Federation. Russian State Medical University. 2001;491-492. Russian.

Guo et al., Group 5 and group 6 metal halides as very efficient catalysts for acylative cleavage of ethers.v Tetrahedron. Sep. 2002;58(36):7327-7334.

Gupta et al., Angiogenesis: a curse or cure? Postgrad Med J. Apr. 2005;81(954):236-42.

Gupta et al., Morphine exaggerates retinopathy in transgenic sickle mice. Blood (ASH Annual Meeting Abstract) 2005; 106: Abstract 209.

Gupta et al., Morphine mimics VEGF in vascular endothelium by promoting pro-angiogenic and survival promoting signaling and angiogenesis. FASEB Journal. 2002; 16(4):A207. Abstract #182.12.

Gupta et al., Morphine stimulates angiogenesis by activating proangiogenic and survival-promoting signaling and promotes breast tumor growth. Cancer Res. Aug. 1, 2002;62(15):4491-8.

Gutstein et al., Role of inositol 1,4,5-trisphosphate receptors in regulating apoptotic signaling and heart failure. Heart Vessels. 1997;Suppl 12:53-7.

Guy et al., Structural models of Na+, Ca2+, and K+ channels. Ion Channels and Genetic Diseases. Society of General Physiologists, 48th Annual Symposium, David C. Dawson (Ed.), Chapter 1, pp. 1-28, (1995).

Hailes et al., Biological synthesis of the analgesic hydromorphone, an intermediate in the metabolism of morphine, by Pseudomonas putida M10. Appl Environ Microbiol. Jul. 1993;59(7):2166-70.

Hanif et al., Hypotensive effect of novel chimeric peptides of met-enkephalin and FMRFa. Regul Pept. Feb. 15, 2005;125(1-3):155-61.

Hanson et al., American Gastroenterological Association Institute Technical Review on the Medical Management of Opioid-Induced Constipation. Gastroenterology. Jan. 2019;156(1):229-253.

He et al., Improvement of Bowel Dysfunction Caused by Opioid Analgesics: Research Advances on Methylnaltrexone. Chinese Journal of Clinical Rehabilitation. 2002;6(20):3104-05.

Hein et al., Pharmacological analysis of the discriminative stimulus characteristics of ethylketazocine in the rhesus monkey. J Pharmacol Exp Ther. Jul. 1981;218(1):7-15.

Hicks et al., Differential effects of the novel non-peptidic opioid 4-tyrosylamido-6-benzyl-1,2,3,4 tetrahydroquinoline (CGPM-9) on in vitro rat t lymphocyte and macrophage functions. Life Sci. May 4, 2001;68(24):2685-94.

Hirota et al., Loss of a gp130 cardiac muscle cell survival pathway is a critical event in the onset of heart failure during biomechanical stress. Cell. Apr. 16, 1999;97(2):189-98.

Ho et al., Beta-endorphin: peripheral opioid activity of homologues from six species. Int J Pept Protein Res. Apr. 1987;29(4):521-4.

Ho et al., Suppression of immunological functions in morphine addicted mice. NIDA Res Monogr. 1986;75:599-602.

(56) References Cited

OTHER PUBLICATIONS

Ho et al., Methylnaltrexone antagonizes opioid-mediated enhancement of HIV infection of human blood mononuclear phagocytes. J Pharmacol Exp Ther. Dec. 2003;307(3):1158-62. Epub Oct. 14, 2003.
Hoffmann et al., [Calcium in the prevention of stress ulcer in the rat] Langenbecks Arch Chir. 1976;Suppl:228-32. German. English Abstract only.
Hofmann et al., Hypocalcemia during restraint stress in rats. Indication that gastric ulcer prophylaxis by exogenous calcium interferes with calcitonin release. Res Exp Med (Berl). May 30, 1979;175(2):159-68.
Holzer, Opioids and opoid receptors in the enteric nervous system: from a problem in opioid analgesia to a possible new prokinetic therapy in humans. Neuroscience Letters. 2004;361:192-195.
Hou et al., A mu-receptor opioid agonist induces AP-1 and NF-kappa B transcription factor activity in primary cultures of rat cortical neurons. Neurosci Lett. Jul. 19, 1996;212(3):159-62.
Howd et al., Naloxone and intestinal motility. Experientia. Oct. 15, 1978;34(10):1310-1.
Hui et al., Overview of the progress in the research of the oral absorption enhancer. West China Medical Journal. 2008;23(4):940-942.
Hussain et al., Improvement of the oral bioavailability of naltrexone in dogs: a prodrug approach. J Pharm Sci. May 1987;76(5):356-8.
Hussain et al., Naltrexone-3-salicylate (a prodrug of naltrexone): synthesis and pharmacokinetics in dogs. Pharm Res. Feb. 1988;5(2):113-5.
Hutchinson et al., Assessment in the guinea-pig ileum and mouse vas deferens of benzomorphans which have strong antinociceptive activity but do not substitute for morphine in the dependent monkey. Br J Pharmacol. Dec. 1975;55(4):541-6.
Hutchinson et al., Scintigraphic measurement of ileocaecal transit in irritable bowel syndrome and chronic idiopathic constipation. Gut. Apr. 1995;36(4):585-9.
Iorio et al., Diastereoisomeric Quaternary Morphinium Salts: Synthesis, Stereochemistry and Analgesic Properties. European Journal of Medicinal Chemistry. 1984;19(1):11-16.
Iorio et al., Narcotic agonist/antagonist properties of quaternary diastereoisomers derived from oxymorphone and naloxone. Eur J Med Chem. 1984;19(4):301-3.
IUPAC. Compendium of Chemical Terminology, 2nd ed. (the "Gold Book"). Compiled by A. D. McNaught and A. Wilkinson. Blackwell Scientific Publications, Oxford (1997).XML on-line corrected version: http://goldbook.iupac.org (2006-) https://doi.org/10.1351/goldbook. p. 1.
Jacobson, Annual report: Biological evaluation of compounds for their dependence liability. IV Drug testing program of the Committee on Problems of Drug Dependence, Inc. (1980). Problems of Drug Dependence, 1980: Proceedings of the Annual Scientific Meeting (42nd ). Rockville, MD. National Institute on Drug Abuse; 1981;287-296.
Jalowiec et al., Suppression of juvenile social behavior requires antagonism of central opioid systems. Pharmacol Biochem Behav. Jul. 1989;33(3):697-700.
Jankovic et al., Quaternary naltrexone: its immunomodulatory activity and interaction with brain delta and kappa opioid receptors. Immunopharmacology. Sep.-Oct. 1994;28(2):105-12.
Jasinski, Assessment of the Abuse Potentiality of Morphinelike Drugs (Methods Used in Man). Drug Addiction J. 1997:197-258.
Jasinski, Tolerance and Dependence to opiates. Acta Anaesthesiol Scand. Jan. 1997;41(1 Pt 2):184-6.
Jenab et al., Ethanol and naloxone differentially upregulate delta opioid receptor gene expression in neuroblastoma hybrid (NG 108-15) cells. Brain Res Mol Brain Res. Nov. 1994;27(1):95-102.
Jenke, Suitability-for-Use Considerations for Prefilled Syringes. Retrieved online at: http://www.pharmtech.com/suitability-use-considerations-prefilled-syringes. PharmTech.com, 5 pages, Apr. 1, 2008.

Jiang et al., Tungsten-induced protein aggregation: solution behavior. J Pharm Sci. Dec. 2009;98(12):4695-710.
Jin et al., Overview of the research progress on oral accelerants. West China Medical Journal. Dec. 31, 2008;23(4):940-2.
Johnson et al., Stability of tacrolimus with morphine sulfate, hydromorphone hydrochloride, and ceftazidime during simulated intravenous coadministration. Am J Health Syst Pharm. Jan. 15, 1999;56(2):164-9.
Kakeji et al., Preclinical studies of the combination of angiogenic inhibitors with cytotoxic agents. Invest New Drugs. 1997;15(1):39-48.
Kakemi et al., Absorption and Excretion of Drugs. XL. Enhancement of the Rectal Absorption of Pharmaceutical Amines with Lauryl Sulfate and Saccharine Anions. Chem Pharm Bull. 1969;17(8):1641-1650.
Kararli et al., Ionic Strength Dependence of Dissolution for Eudragit S-100 Coated Pellets. Pharmaceutical Research. 1995;12(11):1813-1816.
Kasamatsu et al., Attenuation of aortic baroreflex responses by microinjections of endomorphin-2 into the rostral ventrolateral medullary pressor area of the rat. Am J Physiol Regul Integr Comp Physiol. Jul. 2005;289(1):R59-67. Epub Feb. 17, 2005.
Kastin et al., EEG evidence that morphine and an enkephalin analog cross the blood-brain barrier. Pharmacol Biochem Behav. Dec. 1991;40(4):771-4.
Kaufman et al., Role of opiate receptors in the regulation of colonic transit. Gastroenterology. Jun. 1988;94(6):1351-6.
Kehlet et al., Review of postoperative ileus. Am J Surg. Nov. 2001;182(5A Suppl):3S-10S. Review.
Keith et al., Failure of naloxone to prevent the emetic activity of apomorphine in dogs. J Vet Pharmacol Ther. Dec. 1981;4(4):315-6.
Kim et al., Assay for methylnaltrexone in rat brain regions and serum by high-performance liquid chromatography with coulometric electrochemical detection. Chromatographia. Oct. 1989;28(7-8):359-63.
Kim et al., The Physical State of Mannitol after Freeze-Drying: Effects of Mannitol Concentration, Freezing Rate, and a Noncrystallizing Cosulute. Journal of Pharmaceutical Sciences. 1998;87(8):931-935.
King et al., Hypothalamic-pituitary-adrenocortical (HPA) axis response and biotransformation of oral naltrexone: preliminary examination of relationship to family history of alcoholism. Neuropsychopharmacology. Jun. 2002;26(6):778-88.
Kinsman et al., Effect of naloxone on feedback regulation of small bowel transit by fat. Gastroenterology. Aug. 1984;87(2):335-7.
Knowles et al., Slow transit constipation: a model of human gut dysmotility. Review of possible aetiologies. Neurogastroenterol Motil. Apr. 2000; 12(2):181-96.
Koblish et al., Behavioral profile of ADL 8-2698, a novel GI-restricted µ opioid receptor antagonist. Society for Neuroscience Abstracts. 2001;27(2):2407. Abstract Only.
Kobylecki et al., N-Methylnalorphine: definition of N-allyl conformation for antagonism at the opiate receptor. J Med Chem. Nov. 1982;25(11):1278-80.
Koch et al., Inhibitory neuropeptides and intrinsic inhibitory innervation of descending human colon. Dig Dis Sci. Jun. 1991;36(6):712-8. Abstract Only.
Koczka, et al., Selective Quaternization of Compounds with Morphine Skeleton. Acta Chimica Academica Scien Hung. 1967;51(4):393-02.
Kodani et al., Delta-opioid receptor-induced late preconditioning is mediated by cyclooxygenase-2 in conscious rabbits. Am J Physiol Heart Circ Physiol. Nov. 2002;283(5):H1943-57.
Koob et al., Effects of opiate antagonists and their quaternary derivatives on heroin self-administration in the rat. J Pharmacol Exp Ther. May 1984;229(2):481-6.
Kosten et al., Naltrexone and morphine alter the discrimination and plasma levels of ethanol. Behav Pharmacol. Feb. 1999;10(1):1-13.
Kostic, The effect of opioid antagonists in local regulation of testicular response to acute stress in adult rats. Steroids 1997 62(11):703-708. Abstract Only.

(56) References Cited

OTHER PUBLICATIONS

Kotake et al., Variations in demethylation of N-methylnaltrexone in mice, rats, dogs, and humans. Xenobiotica. Nov. 1989;19(11):1247-54.

Kotz et al., Acids and Bases. Chemistry & Chemical Reactivity. Chapter 15. Saunders College Publishing, Philadelphia. p. 551-600, (1987).

Koufopoulou et al., Application of the ion pair concept to the n-octanol-water partitioning of cefepime and cefpirome. Int J Pharm. Jun. 19, 2006;316(1-2):52-7.

Kratzel et al., An Effificent Synthesis of 14-Halogenomethyl-Substituted C-Normorphinans. Heterocycles. 1987;26(10):2703-10.

Kratzel et al., Synthesis of 5a, 11b-Propanonaphtho[1,2-e][1,2]oxazepines as Potential Opioid Analgesics. J Chem Soc Perkin 1. 1994;11:1541-43.

Kromer et al., Endogenous opioids, the enteric nervous system and gut motility. Dig Dis. 1990;8(6):361-73.

Kromer et al., The current status of opioid research on gastrointestinal motility. Life Sci. 1989;44(9):579-89.

Lachman et al., The Theory and Practice of Industrial Pharmacy, Third Edition. Varghese Publishing House, Bombay. pp. 190-194, 764. (1987).

Langguth, et al., Intestinal absorption of the quaternary trospium chloride: permeability-lowering factors and bioavailabilities for oral dosage forms. Eur J Pharm Biopharm. 1997;43:265-272.

Langguth, et al., Lipophilisation of hydrophilic compounds. Consequences on transepidermal and intestinal transport of trospium chloride. Arzneimittelforschung. Dec. 1987;37(12):1362-6.

Law et al., Agonist activation of delta-opioid receptor but not mu-opioid receptor potentiates fetal calf serum or tyrosine kinase receptor-mediated cell proliferation in a cell-line-specific manner. Mol Pharmacol. Jan. 1997;51(1):152-60.

Law et al., Properties of delta opioid receptor in neuroblastoma NS20Y: receptor activation and neuroblastoma proliferation. J Pharmacol Exp Ther. Jan. 1995;272(1):322-32.

Law et al., Regulation of opioid receptor activities. J Pharmacol Exp Ther. May 1999;289(2):607-24.

Lazar et al., Synthesis and biological activity of the phosphate and sulfate esters of naloxone and naltrexone. Eur J Med Chem. 1994;29:45-53.

Leander, A kappa opioid effect: increased urination in the rat. J Pharmacol Exp Ther. Jan. 1983;224(1):89-94.

Legen et al., The evaluation of some pharmaceutically acceptable excipients as permeation enhancers for amoxicillin. Int J Pharm. Feb. 3, 2006;308(1-2):84-9.

Levy et al., Effect of Certain Tablet Formulation Factors on Dissolution Rate of the Active Ingredient III, Tablet Lubricants. Journal of Pharmaceutical Sciences. Dec. 1963;52(12):1139-1144.

Li et al., Methadone enhances human immunodeficiency virus infection of human immune cells. J Infect Dis. Jan. 1, 2002;185(1):118-22. Epub Dec. 14, 2001.

Lim et al., Morphine preconditions Purkinje cells against cell death under in vitro simulated ischemia-reperfusion conditions. Anesthesiology. Mar. 2004;100(3):562-8.

Lin et al., Bioavailability of oral methylnaltrexone increases with a phosphatidylcholine-based formulation. Drug Dev Ind Pharm. Feb. 2014;40(2):186-91.

Lindholm, Methylnaltrexone bromide, pH testing. Fresenius Kabi. Test Report. 126 pages. Sep. 21, 2015.

Linn et al., Peripherally restricted µ-opioid receptor antagonists: a review. Tech Reg Anesth Pain Manag. Jul. 2007;11(1):27-32.

Little et al., ADL 8-2698, a GI restricted opioid antagonist, blocks the antisecretory and colorectal transit effects of morphine and loperamide. Society for Neuroscience Abstracts. Nov. 10-15, 2001;27(2):2407.

Livingston et al., Postoperative ileus. Dig Dis Sci. Jan. 1990;35(1):121-32.

Lombardo et al., The Good, the Bad and the Ugly of Distribution Coefficients: Current Status, Views and Outlook. Molecular Drug Properties. Measurement and Prediction (R. Mannhold, Ed.) Chapter 16, pp. 407-437, 2008.

Lopez et al., Demonstration of long-lasting blockade of experimental ileus in rats by an opioid k-agonist. Gastroenterology. 1995;108(4):A640. Abstract.

Lund, Preformulation. The Pharmaceutical Codex, 12th Edition, Principles and Practice of Pharmaceutics. The Pharmaceutical Press, Great Britain. 178-197, (1994).

Lydon et al., Intravenous methylnaltrexone attenuates intrathecal morphine induced delayed gastric emptying in rats. ESA Free Paper Prize Competition. Eur J Anaesthesiol. Apr. 2001;18 Suppl 21:92. Abstract A-327.

Lysle et al., Evidence for the involvement of the caudal region of the periaqueductal gray in a subset of morphine-induced alterations of immune status. J Pharmacol Exp Ther. Jun. 1996;277(3):1533-40.

Lysle et al., Modulation of immune status by a conditioned aversive stimulus: evidence for the involvement of endogenous opioids. Brain Behav Immun. Jun. 1992;6(2):179-88.

Machelska et al., Selectins and integrins but not platelet-endothelial cell adhesion molecule-1 regulate opioid inhibition of inflammatory pain. Br J Pharmacol. Jun. 2004; 142(4):772-80. Epub May 24, 2004.

Mack, Paralytic ileus: response to naloxone. Br J Surg. Oct. 1989;76(10):1101.

Magazine et al., Morphine-induced conformational changes in human monocytes, granulocytes, and endothelial cells and in invertebrate immunocytes and microglia are mediated by nitric oxide. J Immunol. Jun. 15, 1996;156(12):4845-50.

Magnan et al., The binding spectrum of narcotic analgesic drugs with different agonist and antagonist properties. Naunyn Schmiedebergs Arch Pharmacol. Jun. 1982;319(3):197-205.

Maguire et al., Pharmacological profiles of fentanyl analogs at mu, delta and kappa opiate receptors. Eur J Pharmacol. Mar. 24, 1992;213(2):219-25. Abstract Only.

Malspeis et al., Metabolic Reduction of Naltrexone I. Synthesis, Separation and Characterization of Naloxone and Maltrexone Reduction Products and Qualitative Assay of Urine and Bile Following Adminstration of Naltrexone, α-naltrexol, or β-naltrexol. Chem Pathol Pharmacol. 1975;12(1):43-65.

Manara et al., Inhibition of gastrointestinal transit by morphine in rats results primarily from direct drug action on gut opioid sites. J Pharmacol Exp Ther. Jun. 1986;237(3):945-9, Abstract Only.

Manara et al., Peripheral selectivity of quaternary narcotic antagonists: relative ability to prevent gastrointestinal transit inhibition and antinociception in morphinized rats. Adv. Endog. Exog. Opioids, Poroc. Int. Narc. Res. Conf., 12th (1981):402-4.

Manara et al., The central and peripheral influences of opioids on gastrointestinal propulsion. Annu Rev Pharmacol Toxicol. 1985;25:249-73.

Mancev et al., The immunomodulating effects of specific opioid receptor antagonists after their intracerebroventricular application. Intl J Thymol. 1999;7(12-13):589-95.

Manchikanti et al., American Society of Interventional Pain Physicians. American Society of Interventional Pain Physicians (ASIPP) guidelines for responsible opioid prescribing in chronic non-cancer pain: Part 2—guidance. Pain Physician. Jul. 2012;15(3 Suppl):S67-116.

Marmor et al., Coronary artery disease and opioid use. Am J Cardiol. May 15, 2004;93(10):1295-7.

Marshall et al., Tablet Dosage Forms. Modern Pharmaceutics, Second Edition, vol. 40. Marcel Dekker, Inc., New York, Gilbert S. Banker (Ed.). pp. 355-425, (1990).

McBride et al., delta2 opioid receptor agonist facilitates mean arterial pressure recovery after hemorrhage in conscious rats. Shock. Mar. 2005;23(3):264-8.

McCance-Katz et al., Interactions between buprenorphine and antiretrovirals. II. The protease inhibitors nelfinavir, lopinavir/ritonavir, and ritonavir. Clin Infect Dis. Dec. 15, 2006;43 Suppl 4:S235-46.

McCarthy et al., Opioids, opioid receptors, and the immune response. Drug Alcohol Depend. Apr. 1, 2001;62(2):111-23.

(56) References Cited

OTHER PUBLICATIONS

McCarthy et al., Preliminary studies on the use of plasma β-endorphin in horses as an indicator of stress and pain. J Equine Vet Sci. 1993;13(4):216-9.
McNaught et al., aliphatic compounds. IUPAC, International Union of Pure and Applied Chemistry. Gold Book. 1 page, Feb. 24, 2014.
McQuay et al., Opioid problems and morphine metabolism and excretion. http://www.medicine.ox.ac.uk/bandolier/booth/painpag/wisdom/c14.html. Last accessed Feb. 8, 2010. 24 pages.
McQuay, Opioid use in chronic pain. Acta Anaesthesiol Scand. Jan. 1997;41(1 Pt 2):175-83.
Mellon et al., Evidence for central opioid receptors in the immunomodulatory effects of morphine: review of potential mechanism(s) of action. J Neuroimmunol. Mar. 15, 1998;83(1-2):19-28.
Melzig et al., Stimulation of endothelial angiotensin-converting enzyme by morphine via non-opioid receptor mediated processes. Pharmazie. Sep. 1998;53(9):634-7.
Meyer et al., Hydrophobic ion pairing: altering the solubility properties of biomolecules. Pharm Res. Feb. 1998;15(2):188-93.
Mickley et al., Quaternary naltrexone reverses morphine-induced behaviors. Physiol Behav. Aug. 1985;35(2):249-53.
Miedema et al., Methods for decreasing postoperative gut dysmotility. Lancet Oncol. Jun. 2003;4(6):365-72.
Misra et al., Intravenous kinetics and metabolism of [15, 16-3H]naltrexonium methiodide in the rat. J Pharm Pharmacol. Mar. 1987;39(3):225-7.
Miyagi et al., Morphine induces gene expression of CCR5 in human CEMx174 lymphocytes. J Biol Chem. Oct. 6, 2000;275(40):31305-10.
Moerman et al., Evaluation of methylnaltrexone for the reduction of postoperative vomiting and nausea incidences. Acta Anaesthesiol Belg. 1995;46(3-4):127-32.
Moss et al., Development of peripheral opioid antagonists' new insights into opioid effects. Mayo Clin Proc. Oct. 2008;83(10):1116-30.
Moss et al., Glossary of Class Names of Organic Compounds and Reactive Intermediate Based on Structure. Pure & Appl Chem. 1995;67(8/9):1307-1375.
Moss et al., Methylnaltrexone prevents morphine-induced CCR5 receptor expression. Anesthesiology. 2003;99. Abstract A-961.
Moss et al., Opioid-induced changes in pulmonary barrier integrity may explain heroid-induced pulmonary edema. American Society of Anesthesiologists presentation, Oct. 17, 2007 in San Francisco, CA. Abstract A, 1 page, 1980.
Moss et al., Pain Relief without Side Effects: Peripheral Opiate Antagonists. ASA, vol. Thirty-three, Alan Jay Schwartz (Ed.). Chapter 15, pp. 175-186, (2005).
Moss, et al., Selective postoperative inhibition of gastrointestinal opioid receptors. N. Engl. J. Med. 2002;346(6):455.
Movantik, Highlights of Prescribing Information, Initial U.S. Approval 2014. Package Insert, 19 pages, Revised Feb. 2018.
Mucha, Is the motivational effect of opiate withdrawal reflected by common somatic indices of precipitated withdrawal? A place conditioning study in the rat. Brain Res. Aug. 25, 1987;418(2):214-20.
Mucha, Taste aversion involving central opioid antagonism is potentiated in morphine-dependent rats. Life Sci. 1989;45(8):671-8.
Murphy et al., Opioid antagonist modulation of ischaemia-induced ventricular arrhythmias: a peripheral mechanism. J Cardiovasc Pharmacol. Jan. 1999;33(1):122-5.
Murphy et al., Opioid-induced delay in gastric emptying: a peripheral mechanism in humans. Anesthesiology. Oct. 1997;87(4):765-70.
Murphy et al., Pharmacokinetic profile of epidurally administered methylnaltrexone, a novel peripheral opioid antagonist in a rabbit model. Br J Anaesth. Jan. 2001;86(1):120-2.
Murphy et al., Pharmaconkinetic of epidural administered methylnaltrexone a novel peripheral opioid anatagonist. American Society of Anesthesiologists, 1999 annual meeting. Dallas, Texas, USA. Oct. 9-13, 1999. Anesthesiology. Sep. 1999;91(3A Suppl):A349.
Mutschler et al., Arzneimittelwirkungen: Lehrbuch der Pharmakologie und Toxikologie, 8th Edition. Wissenschaftliche Verlagsgesellschaft mbH. pp. 214-219, (2001).
Nair et al., Morphine Modulates the Expression of Chemokines and their Receptors by Peripheral Blood Mononuclear Cells (PBMC) from Normal Donors. J Allergy Clin Immunol. 1998:101(1):S57. Abstract 244.
Naranjo et al., Evidence for a central but not adrenal, opioid mediation in hypertension induced by brief isolation in the rat. Life Sci. May 26, 1986;38(21):1923-30.
Nelson et al., Involvement of central mu- but not delta- or kappa-opioid receptors in immunomodulation. Brain Behav Immun. Sep. 2000; 14(3): 170-84.
Nelson, Morphine modulation of the contact hypersensitivity response: A pharmacological and immunological characterization. University of North Carolina at Chapel Hill. Dissertation Abstracts International. 2001;62/03-B:1635. 94 pages. Abstract Only.
Nemeth-Lefkowitz et al., Hematological and Immunological Effects of Methadone Administration in Mice. Research Communications in Substance Abuse. 1980;1(2):177-83.
Neumann et al., Plasma morphine concentrations during chronic oral administration in patients with cancer pain. Pain. Jul. 1982;13(3):247-52.
Nielsen et al., Glycolamide Esters as Biolabile Prodrugs of Carboxylic Acid Agents: Synthesis, Stability, Biocenversion, and Physicochemical Properties. J Pharma Sci. 1988;77:285-98.
Niemegeers et al., Difenoxine (R 15403), the active metabolite of diphenoxylate (R 1132). 2. Difneozine, a potent, orally active and safe antidiarrheal agent in rats. Arzneimittelforschung. Mar. 1972;22(3):516-8.
Notari, Biopharmaceutics. Biopharmaceutics and Clinical Pharmacokinetics, an Introduction. 4th Edition. Marcel Dekker, New York. Chapter 5, pp. 130-170. (1987).
Novak et al., Tungsten (V) complexes of ethylenediaminetetraacetic acid. Journal of Inorganic and Nuclear Chemistry. May 1974;36(5):1061-1065.
Novick et al., Natural killer cell activity and lymphocyte subsets in parenteral heroin abusers and long-term methadone maintenance patients. J Pharmacol Exp Ther. Aug. 1989;250(2):606-10.
Nusrat et al., Pharmacological Treatment of Opioid-Induced Constipation is Effective but Choice of Endpoints Affects the Therapeutic Gain. Dig Dis Sci. Jan. 2019;64(1):39-49.
O'Keefe et al., Bowel Disorders Impair Functional Status and Quality of Life in the Elderly: A Population-Based Study. J Gerontol. 1995;50:184-89.
Odio et al., Central but not peripheral opiate receptor blockade prolonged pituitary-adrenal responses to stress. Pharmacol Biochem Behav. Apr. 1990;35(4):963-9.
OECD Guideline for the Testing of Chemicals. Partition Coefficient (n-octanol/water): Shake Flask Methods. 4 pages, Jul. 27, 1995.
Osinski et al., Determination of methylnaltrexone in clinical samples by solid-phase extraction and high-performance liquid chromatography for a pharmacokinetics study. J Chromatogr B Analyt Technol Biomed Life Sci. Nov. 25, 2002;780(2):251-9.
Pandit, Solubility and Lipophilicity. Introduction to the Pharmaceutical Sciences. Lippincott Williams & Wilkins, Baltimore. Chapter 3, pp. 27-42, (2007).
Pannemans et al., New developments in the treatment of opioid-induced gastrointestinal symptoms. United European Gastroenterol J. Oct. 2018;6(8):1126-1135.
Papapetropoulos et al., Nitric oxide synthase inhibitors attenuate transforming-growth-factor-beta 1-stimulated capillary organization in vitro. Am J Pathol. May 1997;150(5): 1835-44.
Pappagallo, Incidence, prevalence, and management of opioid bowel dysfunction. Am J Surg. Nov. 2001;182(5A Suppl):11S-18S.
Parolaro et al., Effect of intracerebroventricular administration of morphine upon intestinal motility in rat and its antagonism with naloxone. Eur J Pharmacol. Dec. 15, 1977;46(4):329-38.
Pasi et al., Angiogenesis: modulation with opioids. Gen Pharmacol. 1991;22(6):1077-9.
Patel et al., COX-2 and iNOS in opioid-induced delayed cardioprotection in the intact rat. Life Sci. May 28, 2004;75(2):129-40.

(56) References Cited

OTHER PUBLICATIONS

Patrick, Instant Notes: Organic Chemistry, 2nd Edition. BIOS Scientific Publishers, London. 42 pages, (2004).

Paulekuhn et al., Trends in active pharmaceutical ingredient salt selection based on analysis of the Orange Book database. J Med Chem. Dec. 27, 2007;50(26):6665-72.

Paulson et al., Alvimopan: an oral, peripherally acting, mu-opioid receptor antagonist for the treatment of opioid-induced bowel dysfunction—a 21-day treatment-randomized clinical trial. J Pain. Mar. 2005;6(3):184-92.

Peart et al., Opioid-induced preconditioning: recent advances and future perspectives. Vascul Pharmacol. Apr.-May 2005;42(5-6):211-8. Epub Mar. 17, 2005.

Peeters et al., The motilin antagonist ANQ-11125 blocks motilide-induced contractions in vitro in the rabbit. Biochem Biophys Res Commun. Jan. 28, 1994; 198(2):411-6. Abstract Only.

Pergolizzi et al., Peripherally acting μ-opioid receptor antagonists as treatment options for constipation in noncancer pain patients on chronic opioid therapy. Patient Prefer Adherence. Jan. 17, 2017;11:107-119.

Peterson et al., Morphine promotes the growth of HIV-1 in humanmononuclear cell cocultures. AIDS. Sep. 1990;4(9):869-73.

Pham et al., Drugs of Abuse: Chemistry, Pharmacology, Immunology and AIDS; National Institute of Drug Research 96: Monograph Series. U.S. Department of Health and Human Services; 1990. 243 pages.

Picado et al., Opioid-Induced Constipation. Pharmacy Times, retrieved online at: https://www.pharmacytimes.com/publications/health-system-edition/2018/september2018/opioidinduced-constipation. 4 pages, Sep. 12, 2018.

Polak et al., Enkephalin-like immunoreactivity in the human gastrointestinal tract. Lancet. May 7, 1977;1(8019):972-4.

Polakiewicz et al., mu-Opioid receptor activates signaling pathways implicated in cell survival and translational control. J Biol Chem. Sep. 4, 1998;273(36):23534-41.

Poonawala et al., Opioids heal ischemic wounds in the rat. Wound Repair Regen. Mar.-Apr. 2005;13(2):165-74.

Powell et al., Paradoxical effects of the opioid antagonist naltrexone on morphine analgesia, tolerance, and reward in rats. J Pharmacol Exp Ther. Feb. 2002;300(2):588-96.

Pugsley et al., Cardiovascular actions of the kappa-agonist, U-50,488H, in the absence and presence of opioid receptor blockade. Br J Pharmacol. Mar. 1992;105(3):521-6.

Quang-Cantagrel et al., Long-term methadone treatment: effect on CD4+ lymphocyte counts and HIV-1 plasma RNA level in patients with HIV infection. Eur J Pain. 2001;5(4):415-20.

Quarry et al., Investigation of 4,5-epoxymorphinan degradation during analysis by HPLC. Journal of Pharmaceutical and Biomedical Analysis. 2002;30:99-104.

Quintanar-Guerrero et al., Applications of the ion-pair concept to hydrophilic substances with special emphasis on peptides. Pharm Res. Feb. 1997;14(2):119-27.

Quock et al., Narcotic antagonist potentiation of apomorphine drug effect: a stereospecific, centrally mediated drug action. Prog Neuropsychopharmacol Biol Psychiatry. 1985;9(3):239-43.

Quock et al., Narcotic antagonist-induced hypotension in the spontaneously hypertensive rat. Life Sci. Sep. 2, 1985;37(9):819-26.

Quock, et al., Microwave facilitation of methylnaltrexone antagonism of morphine-induced analgesia in mice. J Bioelect. 1986;5(1):35-46.

Radulovic et al., Opioid receptor-mediated suppression of humoral immune response in vivo and in vitro: involvement of kappa opioid receptors. J Neuroimmunol. Mar. 1995;57(1-2):55-62.

Ramabadran, Effects of N-methylnaloxone and N-methylnaltrexone on nociception and precipitated abstinence in mice. Life Sci. Sep. 20-27, 1982;31(12-13):1253-6.

Rauck et al., Oral Methylnaltrexone for the Treatment of Opioid-Induced Constipation in Patients with Noncancer Pain. Gastroenterology May 1, 2012, 142(5):S-160. Abstract Only.

Read et al., Interpretation of the breath hydrogen profile obtained after ingesting a solid meal containing unabsorbable carbohydrate. Gut. Aug. 1985;26(8):834-42.

Redfern et al., Relationships between preclinical cardiac electrophysiology, clinical QT interval prolongation and torsade de pointes for a broad range of drugs: evidence for a provisional safety margin in drug development. Cardiovasc Res. Apr. 1, 2003;58(1):32-45.

Reisine et al., Opioid Analgesics and Antagonists. In: Goodman & Goodman's The Pharmacological Basis of Therapeutics. 9th Ed. 1996:521-55.

Relistor (methylnaltrexone bromide) Subcutaneous Injection, Initial U.S. Approval: 2008, Highlighst of Prescribing Information. 22 pages, Revised Jun. 2009.

Relistor(R), Orange Book: Approved Drug Products with Therapeutic Equivalence Evaluations. 2 pages, Aug. 21, 2021.

Relistor, Highlights of Prescribing Information, Initial U.S. Approval 2008. Package Insert, 58 pages, Revised Jul. 2016.

Resnick et al., Delayed gastric emptying and postoperative ileus after nongastric abdominal surgery: part I. Am J Gastroenterol. May 1997;92(5):751-62.

Resnick et al., Delayed gastric emptying and postoperative ileus after nongastric abdominal surgery: part II. Am J Gastroenterol. Jun. 1997;92(6):934-40.

Rios et al., Big Shot: Development in Prefilled Syringes. PharmTech.com. 6 pages, Mar. 2, 2007.

Ripin et al., pKa Table. PDF available at The Evans Group, Chemistry and Chemical Biology, Harvard University, http://evans.rc.fas.harvard.edu/, 6 pages, Nov. 4, 2005.

Risdahl et al., Opiates and infection. J Neuroimmunol. Mar. 15, 1998;83(1-2):4-18.

Rivière et al., Fedotozine reverses ileus induced by surgery or peritonitis: action at peripheral kappa-opioid receptors. Gastroenterology. Mar. 1993; 104(3):724-31.

Robinson et al., Oral naloxone in opioid-associated constipation. Lancet. Aug. 31, 1991;338(8766):581-2.

Roger et al., Colonic motor responses in the pony: relevance of colonic stimulation by opiate antagonists. Am J Vet Res. Jan. 1985;46(1):31-5.

Rosow, Methylnaltrexone: reversing the gastrointestinal effects of opioids. Anesthesiology. Oct. 1997;87(4):736-7.

Rowe et al., Handbook of Pharmaceutical Excipients, 5th Edition. Pharmaceutical Press and the American Pharmaceutical Association. pp. 51, 52, 132-135, 139-141, 214-216, 257-263, 430-433, 580-584, 687-689, 665-668. (2006).

Rowe et al., Handbook of Pharmaceutical Excipients, 6th edition, Pharmaceutical Press, 917 pages, 2009.

Rowe, et al., Handbook of Pharmaceutical Excipients, 4th Edition, Pharmaceutical Press, London. pp. 225-228, 2003.

Roy et al., Morphine modulates NF kappa B activation in macrophages. Biochem Biophys Res Commun. Apr. 17, 1998;245(2):392-6.

Russell et al., Antagonism of gut, but not central effects of morphine with quaternary narcotic antagonists. Eur J Pharmacol. Mar. 12, 1982;78(3):255-61.

Sachs et al., Peripheral analgesic blockade of hypernociception: activation of arginine/NO/cGMP/protein kinase G/ATP-sensitive K+ channel pathway. Proc Natl Acad Sci USA. Mar. 9, 2004;101(10):3680-5. Epub Feb. 2, 20047.

Saffran et al., A new approach to the oral administration of insulin and other peptide drugs. Science. Sep. 5, 1986;233(4768):1081-4. Abstract Only.

Sakurada et al., Differential antagonism of endomorphin-1 and endomorphin-2 supraspinal antinociception by naloxonazine and 3-methylnaltrexone. Peptides. May 2002;23(5):895-901.

Sancho-Chust et al., Experimental Studies on the Influence of Surfactants on Intestinal Absorption of Drugs. Cefadroxil as model drug and sodium lauryl suflate as model surfactant: studies in rat colon. Arzneim.-Forsch./Drug Res. 1995;45(5):595-601.

Sandner-Kiesling et al., Pharmacology of opioid inhibition to noxious uterine cervical distension. Anesthesiology. Oct. 2002;97(4):966-71.

Sangster, Octanol-Water Partition Coefficients of Simple Organic Compounds. J Phys Chem Ref Data. 1989;18(3):1111-1227.

(56) References Cited

OTHER PUBLICATIONS

Sathyan et al., Pharmacokinetic profile of a 24-hour controlled-release OROS® formulation of hydromorphone in the presence and absence of food. BMC Clinical Pharmacology. 2007;7(2):1-8.

Satyavan et al., Managing Opioid-Induced Constipation. Pharmacyonline at: https://www.pharmacytimes.com/publications/issue/2009/september2009/counselingconstipation-09009. 4 pages, Sep. 15, 2009.

Sawhney et al., Bioerodible Hydrogels Based on Photopolymerized Poly(ethylene glycol)-co-poly($\alpha$-hydroxy acid) Diacrylate Macromers. Macromolecules. 1993;26:581-87.

Schaefer et al., Effects of opioid antagonists and their quaternary derivatives on locomotor activity and fixed ratio responding for brain self-stimulation in rats. Pharmacol Biochem Behav. Nov. 1985;23(5):797-802.

Schang et al., Beneficial effects of naloxone in a patient with intestinal pseudoobstruction. Am J Gastroenterol. Jun. 1985;80(6):407-11.

Schang et al., How does morphine work on colonic motility? An electromyographic study in the human left and sigmoid colon. Life Sci. Feb. 24, 1986;38(8):671-6.

Schiller et al., Studies of the mechanism of the antidiarrheal effect of codeine. J Clin Invest. Nov. 1982;70(5):999-1008.

Schmidhammer et al., 183. 5-Methylnaloxone and 5-methylnaltrexone: Synthesis and Pharmaceucal Evaluation. Helvetica Chimica Acta. 1990;73(7):1986-1990.

Schmidhammer, et al., Synthesis and biological evaluation of 14-alkoxymorphinans. Part 101-14-O-methyl derivatives of 5-methylnalthrexone and 5-methylnaloxone. Helv Chim Acta. 1994;77(6):1585-9.

Schmidhammer, et al., Synthesis and biological evaluation of 14-alkoxymorphinans. Part 91-14-O-ethyl-5-methylnaltrexone, an opioid antagonist with unusual selectivity. Helv Chim Acta. 1993;76(1):476-80.

Schmidt et al., Alvimopan* (ADL 8-2698) is a novel peripheral opioid antagonist. Am J Surg. Nov. 2001; 182(5A Suppl):27S-38S.

Scholz, Managing constipation that's opioid-induced. RN. Jun. 2000;63(6):103.

Schreier et al., Central regulation of intestinal function: morphine withdrawal diarrhea. Proc West Pharmacol Soc. 1982;25:151-4.

Schubert-Zsilavecz et al., [Das reizdarmsyndrom] The irritable bowel syndrome. Deutsche apotheker zeitung. Aug. 22, 2002;142(34):40-9. German. English translation only.

Schug et al., A long-term survey of morphine in cancer pain patients. J Pain Symptom Manage. Jul. 1992;7(5):259-66. Abstract Only.

Schuller et al., M6G, but not morphine, inhibits GI transit in mu opioid receptor deficient mice. Society of Neuroscience Abstracts. 1998;24:524. Abstract 210.7.

Sezen et al., Renal excretory responses produced by the delta opioid agonist, BW373U86, in conscious rats. J Pharmacol Exp Ther. Oct. 1998;287(1):238-45.

Shahbazian et al., Involvement of mu- and kappa-, but not delta-, opioid receptors in the peristaltic motor depression caused by endogenous and exogenous opioids in the guinea-pig intestine. Br J Pharmacol. Feb. 2002;135(3):741-50.

Shavit et al., Effects of a single administration of morphine or footshock stress on natural killer cell cytotoxicity. Brain Behav Immun. Dec. 1987;1(4):318-28.

Shi et al., Cardioprotective effects of morphine on rat heart suffering from ischemia and reperfusion. Chin Med J (Engl). Jul. 2003;116(7):1059-62.

Sievänen, Exploitation of bile acid transport systems in prodrug design. Molecules. Aug. 16, 2007;12(8):1859-89.

Simonin et al., kappa-Opioid receptor in humans: cDNA and genomic cloning, chromosomal assignment, functional expression, pharmacology, and expression pattern in the central nervous system. Proc Natl Acad Sci USA. Jul. 18, 1995;92(15):7006-10.

Simonin et al., The human delta-opioid receptor: genomic organization, cDNA cloning, functional expression, and distribution in human brain. Mol Pharmacol. Dec. 1994;46(6):1015-21. Abstract Only.

Singleton et al., Attenuation of vascular permeability by methylnaltrexone: role of mOP-R and S1P3 transactivation. Am J Respir Cell Mol Biol. Aug. 2007;37(2):222-31.

Snyder Bulik, AstraZeneca and Daiichi Sankyo field backlash over Super Bowl OIC awareness ad, retrieved online at: https://www.fiercepharma.com/marketing/astrazeneca-uses-snails-and-overstuffed-luggage-topush-oic-awareness-and-its-branded. 2 pages, Feb. 12, 2016.

Snyder Bulik, AstraZeneca uses snails and overstuffed luggage to push OIC awareness—and its branded solution, retrieved online at: https://www.fiercepharma.com/sales-and-marketing/astrazeneca-and-daiichi-sankyo-fieldbacklash-over-super-bowl-oic-awareness-ad. 2 pages, Aug. 26, 2015.

Soldani et al., Central and peripheral involvement of mu receptors in gastric secretory effects of opioids in the dog. Eur J Pharmacol. Nov. 19, 1985;117(3):295-301.

Solvason et al., Naltrexone blocks the expression of the conditioned elevation of natural killer cell activity in BALB/c mice. Brain Behav Immun. Sep. 1989;3(3):247-62.

Spierings et al., Lubiprostone for Opioid-Induced Constipation Does Not Interfere with Opioid Analgesia in Patients with Chronic Noncancer Pain. Pain Pract. Mar. 2017;17(3):312-319.

Stankski et al., Kinetics of intravenous and intramuscular morphine. Clin Pharmacol Ther. Jul. 1978;24(1):52-9.

Steele et al., HIV-1 Infection and Opioid Administration Modulate the Expression of Chemokine Receptors. Drug and Alcohol Dependence. 2000:60(Supp 1):S212. Abstract 599.

Steele et al., Preformulation as an Aid to Product Design in Early Drug Development. Pharmaceutical Preformulation and Formulation, A Practical Guide from Candidate Drug Selection to Commercial Dosage Form. Mark Gibson (Ed.), CRC Press. Chapter 6, pp. 175-237 (2001).

Stefano et al., Delta2 opioid receptor subtype on human vascular endothelium uncouples morphine stimulated nitric oxide release. Int J Cardiol. Apr. 30, 1998;64 Suppl 1:S43-51.

Stefano et al., Long-term exposure of human blood vessels to HIV gp 120, morphine, and anandamide increases endothelial adhesion of monocytes: uncoupling of nitric oxide release. J Cardiovasc Pharmacol. Jun. 1998;31(6):862-8.

Stefano et al., Morphine enhances nitric oxide release in the mammalian gastrointestinal tract via the micro(3) opiate receptor subtype: a hormonal role for endogenous morphine. J Physiol Pharmacol. Mar. 2004;55(1 Pt 2):279-88.

Stefano et al., Presence of the mu3 opiate receptor in endothelial cells. Coupling to nitric oxide production and vasodilation. J Biol Chem. Dec. 22, 1995;270(51):30290-3.

Steinbrook et al., An opioid antagonist for postoperative ileus. N Engl J Med. Sep. 27, 2001;345(13):988-9.

Stephenson et al., Methylnaltrexone reverses opioid-induced constipation. Lancet Oncol. Apr. 2002;3(4):202.

Sternini et al., The opioid system in the gastrointestinal tract. Neurogastroenterol Motil. Oct. 2004; 16 Suppl 2:3-16.

Stewart et al., Central and peripheral actions of morphine on intestinal transit. J Pharmacol Exp Ther. Jun. 1978;205(3):547-55.

Stiene-Martin et al., Regional, developmental, and cell cycle-dependent differences in mu, delta, and kappa-opioid receptor expression among cultured mouse astrocytes. Glia. Mar. 1998;22(3):249-59.

Suzuki et al., Morphine suppresses lymphocyte apoptosis by blocking p53-mediated death signaling. Biochem Biophys Res Commun. Sep. 5, 2003;308(4):802-8.

Swan, et al., NIDA plays key role in studying links between AIDS and drug abuse. AIDS Research, NIDA Notes. 1995; 10(3):1-4.

Swift et al., BIOT 15—Tungsten, prefilled syringes and protein aggregation. Biophysical and Biomolecular Symposium: Protein Stability. The 234th ACS National Meeting, Boston, MA, Aug. 19-23, 2007. Abstract. Retrieved on May 25, 2016 at<oasys2.confex.com/acs/234nm/techprogram/P1096944.HTM>. 1 page.

(56) References Cited

OTHER PUBLICATIONS

Sykes, Chapter 9. Using oral naloxone in management of opioid bowel dysfunction. Handbook of Opioid Bowel Syndrome, New York, Haworth Medical Press, Yuan, C-S, editor. 2005:175-95.
Sykes, Oral naloxone in opioid-associated constipation. Lancet. Jun. 15, 1991;337(8755):1475.
Symproic, Highlights of Prescribing Information, Initial U.S. Approval 2017. Package Insert, 14 pages, Revised Mar. 2017.
Szabo et al., Interactions of opioid receptors, chemokines, and chemokine receptors. Adv Exp Med Biol. 2001;493:69-74.
Taguchi et al., Selective postoperative inhibition of gastrointestinal opioid receptors. N Engl J Med. Sep. 27, 2001;345(13):935-40.
Takacs-Novak et al., Ion-pair partition of quarternary ammonium drugs: the influence of counter ions of different lipophilicity, size, and flexibility. Pharm Res. Oct. 1999;16(10):1633-8.
Talley et al., Pharmacologic therapy for the irritable bowel syndrome. Am J Gastroenterol. Apr. 2003;98(4):750-8.
Tavani et al., Morphine is most effective on gastrointestinal propulsion in rats by intraperitoneal route: evidence for local action. Life Sci. Dec. 8, 1980;27(23):2211-7.
Tegeder et al., Opioids as modulators of cell death and survival—unraveling mechanisms and revealing new indications. Pharmacol Rev. Sep. 2004;56(3):351-69.
The United States Pharmacopeia, The National Formulary. Monograph for Naltrexone. USP 29, NF 24, pp. 1476-1478, 2556-2557, Jan. 1, 2006.
Thomas et al., A phase III double-blind placebo-controlled trial of methylnaltrexone (MNTX) for opioid-induced constipation (OIC) in advanced medical illness (AMI). Abstract No. LBA8003 from the 2005 ASCO Annual Meeting. 3 pages.
Thomas et al., Amelioration of peripheral side effects of opioids: clinical experience with methylnaltrexone (MNTX). Proc World Congr Anesth. 2004:107. Abstract Only.
Thompson et al., Laxatives: clinical pharmacology and rational use. Drugs. Jan. 1980;19(1):49-58.
Thompson et al., Opioid stimulation in the ventral tegmental area facilitates the onset of maternal behavior in rats. Brain Res. Dec. 16, 1996;743(1-2):184-201.
Tobyn et al., Physicochemical comparison between microcrystalline cellulose and silicified microcrystalline cellulose. International Journal of Pharmaceutics. 1998;169:183-194.
Tomiyasu et al., Analysis of intercostal nerve damage associated with chronic post-thoracotomy pain. Anesthesiology. 2001;95. Abstract A-964.
Troy et al., Remington, The Science and Practice of Pharmacy, 21st Edition. Lippincott Williams & Wilkins, a Wolters Kluwer Company, Philadelphia. pp. 680-684, 891-894 and 941-942, (2006).
Tryoen-Toth et al., Regulation of kappa-opioid receptor mRNA level by cyclic AMP and growth factors in cultured rat glial cells. Brain Res Mol Brain Res. Mar. 30, 1998;55(1):141-50.
Twycross et al., Stimulant laxatives and opioid-induced constipation. J Pain Symptom Manage. Feb. 2012;43(2):306-13.
U.S. Department of Health and Human Services et al., Guidance for Industry. Dissolution Testing of Immediate Release Solid Oral Dosage Forms. http://www.fda.gov/cder/guidance.htm. 17 pages, Aug. 1997.
U.S. Pharmacopeia, U.S. Pharmacopeia 29. U.S. Pharmacopeia, Jan. 1, 2006. 6 pages.
UChicagoMedicine, Drug developed at the University of Chicago wins FDA approval. Retrieved online at: https://www.uchicagomedicine.org/forefront/news/2008/april/drug-developed-at-the-university-of-chicago-wins-fda-approval. 4 pages, Apr. 25, 2008.
Ukai et al., Suppression of deprivation-induced water intake in the rat by opioid antagonists: central sites of action. Psychopharmacology (Berl). 1987;91(3):279-84.
University of California, Berkley Buffer website (citing data from Ruzin, 1999, Plant Microtechnique and Microscopy), at web address: microscopy.berkeley.edu/Resources/instructions/buffers.html. 6 pages, (1999).

Uwai et al., Syntheses and receptor-binding studies of derivatives of the opioid antagonist naltrexone. Bioorg Med Chem. Jan. 15, 2004;12(2):417-21.
Vaczek, Promoting dosing accuracy with prefilled syringes. Packaging Digest Apr. 29, 2007. 7 pages.
Valentino et al., Quaternary naltrexone: evidence for the central mediation of discriminative stimulus effects of narcotic agonists and antagonists. J Pharmacol Exp Ther. Jun. 1981;217(3):652-9.
Valentino et al., Receptor binding, antagonist, and withdrawal precipitating properties of opiate antagonists. Life Sci. Jun. 20, 1983;32(25):2887-96.
Vallejo et al., Opioid therapy and immunosuppression: a review. Am J Ther. Sep.-Oct. 2004;11(5):354-65.
Van De Waterbeemd et al., Intestinal Permeability: Predication from Theory. Oral Drug Absorption: Predication and Assessment. Marcel Dekkers, Inc., New York. Jennifer B. Dressman (Ed.). Chapter 4, pp. 31-49, (2000).
Van Hoogdalem et al., Intestinal drug absorption enhancement: an overview. Pharmacol Ther. 1989;44(3):407-43.
Vaughan et al., Human antibodies by design. Nat Biotechnol. Jun. 1998;16(6):535-9.
Venn, Principles and Practice of Bioanalysis. Taylor & Francis, London. p. 71, (2000).
Vermiere et al., Stability and compatibility of morphine. International Journal of Pharmaceutics. 1999; 187:17-51.
Voet et al., Biochemistry. John Wiley & Sons, Inc., pp. 36-39, (1990).
Voigt, Lehrbuch der pharmazeutischen Technologie. VCH, pp. 395, 503, (1987).
Von Hans Naumer et al., Untersuchungsmethoden in der Chemie, Einfuhrung in die moderne Analytik. Georg Thieme Verlag Stuttgart, New York. pp. 64-66 (1986).
Waldhoer et al., Opioid receptors. Annu Rev Biochem. 2004;73:953-90.
Walker, et al., Role of central versus peripheral opioid receptors in analgesia induced by repeated administration of opioid antagonists. Psychopharmacology. 1991;104(2):164-6.
Wall et al., Metabolism and disposition of naltrexone in man after oral and intravenous administration. Drug Metab Dispos. Jul.-Aug. 1981;9(4):369-75.
Walsh et al., The symptoms of advanced cancer: relationship to age, gender, and performance status in 1,000 patients. Support Care Cancer. May 2000;8(3):175-9. Abstract Only.
Wang et al., A non-peptide substance P antagonist (CP-96,345) inhibits morphine-induced NF-kappa B promoter activation in human NT2-N neurons. J Neurosci Res. Feb. 15, 2004;75(4):544-53.
Wang et al., Determination of tungsten in bulk drug substance and intermediates by ICP-AES and ICP-MS. J Pharm Biomed Anal. May 1999;19(6):937-43. Abstract Only.
Wang et al., Human mu opiate receptor. cDNA and genomic clones, pharmacologic characterization and chromosomal assignment. FEBS Lett. Jan. 31, 1994;338(2):217-22. Abstract Only.
Wang et al., Mobilization of calcium from intracellular stores as one of the mechanisms underlying the antiopioid effect of cholecystokinin octapeptide. Peptides. Sep.-Oct. 1992; 13(5):947-51.
Wang et al., Morphine negatively regulates interferon-gamma promoter activity in activated murine T cells through two distinct cyclic AMP-dependent pathways. J Biol Chem. Sep. 26, 2003;278(39):37622-31. Epub Jul. 3, 2003.
Wang et al., The immunosuppressive effects of chronic morphine treatment are partially dependent on corticosterone and mediated by the mu-opioid receptor. J Leukoc Biol. May 2002;71(5):782-90.
Wantong et al., Ion Pair Complex for Drug Delivery System. Isan Journal of Pharmaceutical Sciences. Jul. 2008. 11 pages.
Warren et al., Effects of quaternary naltrexone and chlordiazepoxide in squirrel monkeys with enhanced sensitivity to the behavioral effects of naltrexone. J Pharmacol Exp Ther. Nov. 1985;235(2):412-7.
Wei et al., Effects of Subcutaneous Methylnaltrexone on Morphine-Induced Gut Motility Changes: A Clinical Trial. Abstracts of the 2002 Annual Meeting of the American Society for Clinical Pharmacology and Therapeutics. Atlanta, Georgia, USA. Mar. 24-27, 2002. Clin Pharmacol Ther. Feb. 2002;71(2). Abstract MPI-26.

(56) References Cited

OTHER PUBLICATIONS

Wei et al., Opioid-induced immunosuppression: is it centrally mediated or peripherally mediated? Biochem Pharmacol. Jun. 1, 2003;65(11):1761-6.
Wei et al., Pharmacokinetics of subcutaneous methylnaltrexone: different route administration comparison. 2001. ASA Annual Meeting Abstracts. Oct. 14-18, 2001. Chicago, IL. Abstract A-962.
Wells, Pharmaceutical performulation: the physicochemical properties of drug substances. Pharmaceutics, The Science of Dosage Form Design, 2nd Edition. Michael E. Aulton (Ed.). Churchill Livingstone, Edinburgh. Chapter 8, pp. 113-138, (2002).
Wentland et al., Synthesis and opioid receptor binding properties of a highly potent 4-hydroxy analogue of naltrexone. Bioorg Med Chem Lett. Apr. 15, 2005;15(8):2107-10.
Whistler et al., Functional dissociation of mu opioid receptor signaling and endocytosis: implications for the biology of opiate tolerance and addiction. Neuron. Aug. 1999;23(4):737-46.
Whitehead et al., Safe and Effective Permeation Enhancers for Oral Drug Delivery. Pharmaceutical Research. 7 pages, (2007). DOI: 10.1007/s11095-007-9488-9.
Willett et al., Direct evidence that the VEGF-specific antibody bevacizumab has antivascular effects in human rectal cancer. Nat Med. Feb. 2004;10(2):145-7. Epub Jan. 25, 2004.
Willette, et al., Evidence for anticholinergic effects of naltrexone methylbromide. Res Comm Subst Abuse. 1983;4(4):325-37.
Wilmore et al., Can we minimize the effects of opioids on the bowel and still achieve adequate pain control? Am J Surg. Nov. 2001; 182(5A Suppl):1S-2S.
Wingo et al., Cancer statistics, 1995. CA Cancer J Clin. Jan.-Feb. 1995;45(1):8-30.
Witkin et al., Pharmacology of 2-amino-indane hydrochloride (Su-8629): a potent non-narcotic analgesic. J Pharmacol Exp Ther. Sep. 1961;133:400-8. Abstract Only.
Wittert et al., Tissue distribution of opioid receptor gene expression in the rat. Biochem Biophys Res Commun. Jan. 26, 1996;218(3):877-81.
Wolff et al., Alvimopan, a novel, peripherally acting mu opioid antagonist: results of a multicenter, randomized, double-blind, placebo-controlled, phase III trial of major abdominal surgery and postoperative ileus. Ann Surg. Oct. 2004;240(4):728-34; discussion 734-5.
Wolinsky, Drug companies fight generics with coupons. Modern Healthcare, retrieved online at: https://www.modernhealthcare.com/article/20160611/MAGAZINE/306119980. 5 pages, Jun. 11, 2016.
Woods et al., Annual report: Evaluation of new compounds for opioid activity (1980). Problems of Drug Dependence, 1980: Proceedings of the Annual Scientific Meeting (42nd). Rockville, MD. National Institute on Drug Abuse, 1981;327-366.
Wybran et al., Suggestive evidence for receptors for morphine and methionine-enkephalin on normal human blood T lymphocytes. J Immunol. Sep. 1979;123(3):1068-70.
Wyeth Canada, PrRelistor, Methylnaltrexone bromide injection, 20 mg/mL, for Subcutaneous use, mu-opioid receptor antagonist. 57 pages, Mar. 27, 2008.
Yamamoto et al., Inhibition of stress-stimulated colonic propulsion by alpha 2-adrenoceptor antagonists in rats. Neurogastroenterol Motil. Dec. 1998; 10(6):523-32. Abstract Only.
Yeh et al., Stability of Morphine in Aqueous Solution III. Journal of Pharmaceutical Sciences. Jan. 1961;50(1):35-42.
Yeh et al., Stability of morphine in aqueous solution. Am J Hosp Pharmacy. 1960;17(2):101-103.
Yoshida et al., Effect of surgical stress on endogenous morphine and cytokine levels in the plasma after laparoscopoic or open cholecystectomy. Surg Endosc. Feb. 2000;14(2):137-40.
Yu et al., Enhancing Oral Bioavailability of Methylnaltrexone Using an Emulsion Formulation. Letters in Drug Design & Discovery. 2011;8:87-92.
Yuan et al., Antagonism of chronic opioid-induce gut effects. Anesth Analg. 2000;90:S1-S23. Abstract S479.
Yuan et al., Antagonism of gastrointestinal opioid effects. Reg Anesth Pain Med. Nov.-Dec. 2000;25(6):639-42.
Yuan et al., Clinical status of methylnaltrexone, a new agent to prevent and manage opioid-induced side effects. J Support Oncol. Mar.-Apr. 2004;2(2):111-7; discussion 119-22.
Yuan et al., Dose-related effects of oral acetaminophen on cold-induced pain: a double-blind, randomized, placebo-controlled trial. Clin Pharmacol Ther. Mar. 1998;63(3):379-83.
Yuan et al., Effects of enteric-coated methylnaltrexone in preventing opioid-induced delay in oral-cecal transit time. Clin Pharmacol Ther. Apr. 2000;67(4):398-404.
Yuan et al., Effects of intravenous methylnaltrexone on opioid-induced gut motility and transit time changes in subjects receiving chronic methadone therapy: a pilot study. Pain. Dec. 1999;83(3):631-5.
Yuan et al., Effects of low-dose morphine on gastric emptying in healthy volunteers. J Clin Pharmacol. Nov. 1998;38(11):1017-20.
Yuan et al., Effects of methylnaltrexone on chronic opioid induced gut motility and transit time changes. Br J Anaesth. 1998;81(1):94. Abstract Only.
Yuan et al., Effects of methylnaltrexone on chronic opioid-induced gut motility and transit time changes. University of Leicester—Abstracts from the Eighth International Symposium on Pain, Anaesthesia and Endocrinology. Sep. 18-19, 1997. 1 page.
Yuan et al., Effects of methylnaltrexone on morphine-induced inhibition of contraction in isolated guinea-pig ileum and human intestine. Eur J Pharmacol. Mar. 24, 1995;276(1-2):107-11.
Yuan et al., Effects of methylnaltrexone on morphine-induced inhibition of contractions in isolated guinea-pig and human intestine. Anesthesiology. Sep. 1995; 83(3A). Abstract A358.
Yuan et al., Effects of subcutaneous methylnaltrexone on morphine-induced peripherally mediated side effects: a double-blind randomized placebo-controlled trial. J Pharmacol Exp Ther. Jan. 2002;300(1):118-23.
Yuan et al., Efficacy of orally administered methylnaltrexone in decreasing subjective effects after intravenous morphine. Drug Alcohol Depend. Oct. 1, 1998;52(2):161-5.
Yuan et al., Gastric effects of methylnaltrexone on mu, kappa, and delta opioid agonists induced brainstem unitary responses. Neuropharmacology. Mar. 1999;38(3):425-32.
Yuan et al., Gastric effects of mu-, delta- and kappa-opioid receptor agonists on brainstem unitary responses in the neonatal rat. Eur J Pharmacol. Oct. 24, 1996;314(1-2):27-32.
Yuan et al., Gut and brain effects of American ginseng root on brainstem neuronal activities in rats. Amer J Chin Med. 1998; 26: 47-55.
Yuan et al., Gut motility and transit changes in patients receiving long-term methadone maintenance. J Clin Pharmacol. Oct. 1998;38(10):931-5.
Yuan et al., Methylnaltrexone (MNTX) for chronic opioid-induced constipation. 2002 ASCO Annual Meeting. Proc Am Soc Clin Oncol. 2002;21:376a. Abstract 1501.
Yuan et al., Methylnaltrexone (MNTX) reverses chronic opioid constipation: a double-blind, randomized, placebo-controlled trial. Anesthesiology. Sep. 1999; 91 (3A). Abstract A973.
Yuan et al., Methylnaltrexone changes gut motility and transit time in chronic methadone-maintained subjects. Anesth Analg. 1999;88: S1-424. Abstract S404.
Yuan et al., Methylnaltrexone effects on morphine-induced inhibition in isolated guinea-pig and human intestine. Clin Pharm & Therapeut. Feb. 1995;57:138. Abstract PI-11.
Yuan et al., Methylnaltrexone for reversal of constipation due to chronic methadone use: a randomized controlled trial. JAMA. Jan. 19, 2000;283(3):367-72.
Yuan et al., Methylnaltrexone prevents morphine-induced delay in oral-cecal transit time without affecting analgesia: a double-blind randomized placebo-controlled trial. Clin Pharmacol Ther. Apr. 1996;59(4):469-75.
Yuan et al., Methylnaltrexone prevents morphine-induced kaolin intake in the rat. Anesthesiology. 2003;99. Abstract A-922.
Yuan et al., Methylnaltrexone reduces oral-cecal transit time in humans. Dig Dis Week Abstr. 2003:A-578. Abstract T1840.
Yuan et al., Methylnaltrexone reverses morphine-induced changes in gastrointestinal motility: a clinical study. Anesthesiology Sep. 1995; 83(3A): Abstract A360.

(56) References Cited

OTHER PUBLICATIONS

Yuan et al., Methylnaltrexone, a novel peripheral opioid receptor antagonist for the treatment of opioid side effects. Expert Opin Investig Drugs. May 2006;15(5):541-52.
Yuan et al., Methylnaltrexone: investigation of clinical applications. Drug Develop Res. 2000;50(2):133-41.
Yuan et al., Opioid analgesia without gut side effects: effects of methylnaltrexone as a novel peripheral opioid antagonist. Assoc Univ Anesth Abst. 2003: PD2.
Yuan et al., Oral methylnaltrexone for opioid-induced constipation. JAMA. Sep. 20, 2000;284(11):1383-4.
Yuan et al., Oral methylnaltrexone reverses chronic opioid-induced constipation. Anesthesiology. Sep. 2000;93(3A). Abstract A-872.
Yuan et al., Oral methylnaltrexone reverses morphine-induced changes in gastrointestinal motility. Anesthesiology. Sep. 1995;85(3A). Abstract A335.
Yuan et al., Pain control without side effects: clinical studies on methylnaltrexone as a novel peripheral opioid antagonist. 7th America-Japan Anesth Congr. Yamanashi, Japan. 2002:41.
Yuan et al., Pharmacokinetics of intravenous vs. oral methylnaltrexone: evidence for direct gut effects. Anesth Analg. 2001;92: S1-363. Abstract S274.
Yuan et al., Safety and tolerance of oral methylnaltrexone in healthy volunteers. Anesth Analg. 1997;84:S1-599. Abstract S574.
Yuan et al., Subcutaneous methylnaltrexone prevents morphine-induced delay in gut transit time: a clinical trial. Anesthesiology. 2001;95. Abstract A-963.
Yuan et al., The safety and efficacy of oral methylnaltrexone in preventing morphine-induced delay in oral-cecal transit time. Clin Pharmacol Ther. Apr. 1997;61(4):467-75.
Yuan et al., Tolerability, gut effects, and pharmacokinetics of methylnaltrexone following repeated intravenous administration in humans. J Clin Pharmacol. May 2005;45(5):538-46.
Zagon et al., Opioid antagonists inhibit the growth of metastatic murine neuroblastoma. Cancer Lett. Nov. 1983;21(1):89-94.
Zagon et al., Opioid growth factor regulates the cell cycle of human neoplasias. Int J Oncol. Nov. 2000;17(5):1053-61.
Zagon et al., Opioids and differentiation in human cancer cells. Neuropeptides. Oct. 2005;39(5):495-505. Epub Sep. 15, 2005.
Zagon et al., Opioids and the apoptotic pathway in human cancer cells. Neuropeptides. Apr. 2003;37(2):79-88.
Zhang et al., Dynorphin A as a potential endogenous ligand for four members of the opioid receptor gene family. J Pharmacol Exp Ther. Jul. 1998;286(1):136-41.
Zhang et al., Effect of the endogenous kappa opioid agonist dynorphin A(1-17) on cocaine-evoked increases in striatal dopamine levels and cocaine-induced place preference in C57BL/6J mice. Psychopharmacology (Berl). Apr. 2004;172(4):422-9. Epub Jan. 8, 2004.
Zimmerman et al., Discovery of a potent, peripherally selective trans-3,4-dimethyl-4-(3-hydroxyphenyl) piperidine opioid antagonist for the treatment of gastrointestinal motility disorders. J Med Chem. Jul. 22, 1994, 37(15):2262-5.
Declaration in Appeal T 1609/17-3.3.01 (EP 2 368 553). 3 pages. Mar. 13, 2018.
European Search Report for Application No. 11157837.3 dated Jun. 24, 2011.
International Search Report and Written Opinion for PCT/US2004/010997, dated Feb. 9, 2005.
International Search Report and Written Opinion for PCT/US2007/017430 mailed May 7, 2008.
International Search Report and Written Opinion for PCT/US2007/019556 mailed Mar. 12, 2008.
International Search Report for Application No. PCT/US2011/027913, dated Jul. 15, 2011.
Office Action, mailed Dec. 10, 2010, for U.S. Appl. No. 12/639,862.
Office Action, mailed Jan. 26, 2009, for U.S. Appl. No. 11/890,034.
Office Action, mailed Mar. 12, 2009 for U.S. Appl. No. 10/821,811.
Office Action, mailed Oct. 2, 2008, for U.S. Appl. No. 10/821,811.
Office Action, mailed Oct. 23, 2009, for U.S. Appl. No. 11/890,034.
Opposition filed on Mar. 6, 2009 in Ecuadoran Patent Application No. SP-08-8752.
Written Opinion for SG 200506463-9 mailed May 4, 2006.
Written Opinion of PCT/US2004/010996 mailed Aug. 16, 2004.
Written Opinion of PCT/US2004/010998 mailed Sep. 1, 2004.
U.S. Appl. No. 12/495,324, filed Jun. 30, 2009, 2010-0087472, Abandoned.
U.S. Appl. No. 13/230,193, filed Sep. 12, 2011, 2012-0190702, Abandoned.
U.S. Appl. No. 13/533,578, filed Jun. 26, 2012, 2012-0277260, Abandoned.
U.S. Appl. No. 12/639,862, filed Dec. 16, 2009, U.S. Pat. No. 8,552,025, Issued.
U.S. Appl. No. 12/639,892, filed Dec. 16, 2009, 2010-0261746, Abandoned.
U.S. Appl. No. 12/639,880, filed Dec. 16, 2009, 2010-0267758, Abandoned.
U.S. Appl. No. 12/639,889, filed Dec. 16, 2009, 2010-0261745, Abandoned.
U.S. Appl. No. 14/039,866, filed Sep. 27, 2013, U.S. Pat. No. 9,669,0096, Issued.
U.S. Appl. No. 15/474,614, filed Mar. 30, 2017, U.S. Pat. No. 10,376,584, Issued.
U.S. Appl. No. 16/440,304, filed Jun. 13, 2019, 2019-0358328, Abandoned.
U.S. Appl. No. 11/890,034, filed Aug. 3, 2007, 2008-0070975, Abandoned.
U.S. Appl. No. 12/726,113, filed Mar. 17, 2010, 2010-0249169, Abandoned.
U.S. Appl. No. 14/105,805, filed Dec. 13, 2013, 2015-0025100, Abandoned.
U.S. Appl. No. 15/158,967, filed May 19, 2016, 2016-0338946, Abandoned.
U.S. Appl. No. 16/433,788, filed Jun. 6, 2019, Abandoned.
U.S. Appl. No. 16/514,722, filed Jul. 17, 2019, 2020-0179270, Abandoned.
U.S. Appl. No. 17/357,023, filed Jun. 24, 2021, 2022-0023200, Published.
U.S. Appl. No. 13/045,108, filed Mar. 10, 2011, U.S. Pat. No. 8,524,276, Issued.
U.S. Appl. No. 13/966,779, filed Aug. 14, 2013, U.S. Pat. No. 8,956,651, Issued.
U.S. Appl. No. 13/956,050, filed Jul. 31, 2013, U.S. Pat. No. 9,314,461, Issued.
U.S. Appl. No. 15/070,555, filed Mar. 15, 2016, 2016-0206612, Abandoned.
U.S. Appl. No. 16/219,159, filed Dec. 13, 2018, U.S. Pat. No. 10,376,505, Issued.
U.S. Appl. No. 16/219,681, filed Dec. 13, 2018, U.S. Pat. No. 10,307,417, Issued.
U.S. Appl. No. 16/450,157, filed Jun. 24, 2019, U.S. Pat. No. 10,507,206, Issued.
U.S. Appl. No. 16/664,239, filed Oct. 25, 2019, 2020-0121673, Published.
U.S. Appl. No. 13/720,235, filed Dec. 19, 2012, 2013-0317050, Abandoned.
U.S. Appl. No. 16/206,570, filed Nov. 30, 2018, 2019-0231771, Abandoned.
U.S. Appl. No. 17/495,413, filed Oct. 6, 2020, Pending.
U.S. Appl. No. 10/821,811, filed Apr. 8, 2004, 2004-0266806, Abandoned.
U.S. Appl. No. 10/778,268, filed Feb. 12, 2004, 2004-0162306, Abandoned.
U.S. Appl. No. 10/357,669, filed Feb. 4, 2003, 2003-0187010, Abandoned.
U.S. Appl. No. 09/669,358, filed Sep. 26, 2000, U.S. Pat. No. 6,559,158, Issued.
U.S. Appl. No. 09/120,703, filed Jul. 22, 1998, U.S. Pat. No. 6,274,591, Issued.
U.S. Appl. No. 08/962,742, filed Nov. 3, 1997, U.S. Pat. No. 5,972,954, Issued.

FORMULATIONS FOR PARENTERAL DELIVERY OF COMPOUNDS AND USES THEREOF

CROSS-REFERENCE TO RELATED APPLICATIONS

The present application is a continuation of U.S. application Ser. No. 17/357,023, filed Jun. 24, 2021, which, in turn, is a continuation of U.S. application Ser. No. 16/514,722, filed Jul. 17, 2019, which, in turn, is a continuation of U.S. application Ser. No. 15/158,967, filed May 19, 2016, which, in turn, is a continuation of U.S. application Ser. No. 14/105,805, filed Dec. 13, 2013, which, in turn, is a continuation of U.S. application Ser. No. 12/726,113, filed Mar. 17, 2010, which, in turn, is a continuation of U.S. application Ser. No. 11/890,034, filed Aug. 3, 2007, which, in turn, claims priority to U.S. Provisional Application No. 60/835,574, filed Aug. 4, 2006. The entire contents of each of the aforementioned applications are incorporated herein by reference.

BACKGROUND OF THE INVENTION

Opioids are widely used in patients with advanced cancers and other terminal diseases to lessen suffering. Opioids are narcotic medications that activate opioid receptors located in the central nervous system to relieve pain. Opioids, however, also react with receptors outside of the central nervous system, resulting in side effects including constipation, nausea, vomiting, urinary retention and severe itching. Most notable are the effects in the gastrointestinal tract (GI) where opioids inhibit gastric emptying and propulsive motor activity of the intestine, thereby decreasing the rate of intestinal transit which can produce constipation. The effectiveness of opioids for pain is often limited due to resultant side effects, which can be debilitating and often cause patients to cease use of opioid analgesics.

In addition to analgesic opioid induced side effects, studies have suggested that endogenous opioid compounds and receptors may also affect activity of the gastrointestinal (GI) tract and may be involved in normal regulation of intestinal motility and mucosal transport of fluids in both animals and man. (Koch, T. R, et al., Digestive Diseases and Sciences 1991, 36, 712-728; Schuller, A. G. P., et al., Society of Neuroscience Abstracts 1998, 24, 524, Reisine, T., and Pasternak, G., Goodman & Gilman's The Pharmacological Basis of Therapeutics Ninth Edition 1996, 521-555 and Bagnol, D., et al., Regul. Pept. 1993, 47, 259-273). Thus, an abnormal physiological level of endogenous compounds and/or receptor activity may lead to bowel dysfunction.

For example, patients who have undergone surgical procedures, especially surgery of the abdomen, often suffer from bowel dysfunction, such as post-operative (or post-surgical) ileus, that may be caused by fluctuations in natural opioid levels. Similarly, women who have recently given birth commonly suffer from post-partum ileus, which is thought to be caused by similar natural opioid fluctuations as a result of birthing stress. Bowel dysfunction associated with post-operative or post partum ileus can typically last for 3 to 5 days, with some severe cases lasting more than a week. Administration of opioid analgesics to a patient after surgery, which is now an almost universal practice, may exacerbate bowel dysfunction, thereby delaying recovery of normal bowel function, prolonging hospital stays, and increasing medical care costs.

Opioid antagonists such as naloxone, naltrexone, and nalmefene, have been studied as a means of antagonizing undesirable peripheral effects of opioids. However, these agents act not only on peripheral opioid receptors, but also on central nervous system sites, so that they sometimes reverse the beneficial analgesic effects of opioids, or cause symptoms of opioid withdrawal. Preferable approaches for use in controlling opioid-induced side effects include use of peripheral opioid antagonist compounds that do not readily cross the blood-brain barrier. For example, the peripheral µ opioid antagonist compound methylnaltrexone and related compounds have been disclosed for use in curbing opioid-induced side effects in patients (e.g., constipation, pruritus, nausea, and/or vomiting). See, e.g., U.S. Pat. Nos. 5,972,954, 5,102,887, 4,861,781, and 4,719,215; and Yuan, C.—S. et al. Drug and Alcohol Dependence 1998, 52, 161.

Formulations of peripheral µ opioid receptor antagonist methylnaltrexone have been described (e.g., see, for example, U.S. Pat. Nos. 6,608,075, 6,274,591, and 6,559,158). However, methylnaltrexone in certain mediums and under certain conditions has been found to form degradation products. For example, see US 2004266806A1. It is desirable to provide dosage forms that are capable of effective delivery of methylnaltrexone without extensive degradation of the methylnaltrexone under refrigeration and/or room temperature conditions.

SUMMARY OF THE INVENTION

The present invention provides certain methylnaltrexone formulations. In some embodiments, the invention provides formulations having improved shelf-life stability characteristics of active compound under refrigeration as well as at room temperature conditions. Provided formulations are useful for parenteral administration of methylnaltrexone. The invention includes methods for production and use of such formulations, as well as products and kits containing provided formulations.

In certain embodiments a pharmaceutical composition is provided containing an effective amount of at least one active compound selected from at least methylnaltrexone, or a pharmaceutically acceptable salt thereof, and a calcium salt chelating agent in an aqueous solution.

In other embodiments, liquid formulations containing methylnaltrexone, or a pharmaceutically acceptable salt thereof, a calcium salt, a chelating agent, an isotonic agent, and an aqueous solvent are provided. In certain embodiments, a calcium salt and a chelating agent are provided together as a calcium salt chelating agent. In some embodiments, a calcium salt chelating agent is selected from calcium ethylenediaminetetraacetic acid (EDTA), calcium diethylenetriaminepentaacetic acid (DTPA), calcium hydroxyethylenediaminetriacetic acid (HEDTA), calcium ethylene glycol-bis-(2-aminoethyl)-N,N,N',N'-tetraacetic acid (EGTA), calcium nitrilotriacetic acid (NTA), calcium citrate, and calcium salt derivatives thereof. In some embodiments a calcium salt chelating agent is calcium EDTA.

In some embodiments, formulations further comprise an additional stabilizing agent. In some embodiments, a stabilizing agent is selected from glycine, benzoic acid, citric, glycolic, lactic, malic, and maleic acid. In certain embodiments, a stabilizing agent is glycine.

In certain embodiments, a formulation comprises methylnaltrexone or a pharmaceutically acceptable salt thereof, a calcium chelating agent, a stabilizing agent, an isotonic agent, and an aqueous solvent. In some embodiments, a formulation comprises methylnaltrexone or a pharmaceutically acceptable salt thereof, calcium EDTA, glycine, and sodium chloride, in an aqueous solution.

In general, provided formulations are useful for preventing, treating or reducing severity of side effects resulting from use of opioids, including inhibition of gastrointestinal dysfunction (e.g., constipation, bowel hypomotility, impaction, gastric hypomotility, GI sphincter constriction, increased sphincter tone, inhibition of gastrointestinal motility, inhibition of intestinal motility, inhibition of gastric emptying, delayed gastric emptying, incomplete evacuation, nausea, emesis (vomiting), bloating, abdominal distension), cutaneous flushing, sweating, dysphoria, pruritis, urinary retention, etc. Provided formulations are useful for administration to patients receiving short term opioid treatment (e.g., patients recovering from surgery (abdominal, orthopedic, surgery from trauma injuries etc.), patients recovering from trauma injuries, and patients recovering from child birth). Formulations are also useful for administration to subjects receiving chronic opioid administration (e.g., terminally ill patients receiving opioid therapy (e.g., an AIDS patient, a cancer patient, a cardiovascular patient); subjects receiving chronic opioid therapy for pain management (e.g., back pain); subjects receiving opioid therapy for maintenance of opioid withdrawal).

Additional uses of provided formulations include prevention, treatment or reduction of severity of symptoms associated with disorders or conditions resulting from normal or aberrant activity of endogenous opioids. Such disorders or conditions include, among others, ileus (e.g., post-partum ileus, paralytic ileus), gastrointestinal dysfunction that develops following abdominal surgery (e.g., colectomy, including but not limited to, right hemicolectomy, left hemicolectomy, transverse hemicolectomy, colectomy takedown, and low anterior resection) such as post-operative ileus, and idiopathic constipation. Provided formulations are also useful in treatment of conditions including, for example, cancers involving angiogenesis, inflammatory disorders (e.g., irritable bowel disorder), immune suppression, cardiovascular disorders (e.g., bradycardia, hypotension) chronic inflammation and/or chronic pain, sickle cell anemia, vascular wounds, and retinopathy, decreased biliary secretion, decreased pancreatic secretion, biliary spasm, and increased gastroesophageal reflux.

BRIEF DESCRIPTION OF THE DRAWING

(FIG. 1A) and room temperature, 250 (FIG. 1B). Both calcium EDTA and sodium EDTA are effective inhibitors of formation of the 2',2' bis methylnaltrexone degradant.

(FIG. 2A) and room temperature, 25° (FIG. 2B) was assessed. Calcium EDTA but not sodium EDTA is an effective inhibitor of formation of the 7-dihydroxy-methylnaltrexone degradant. The effect of CaEDTA on the formation of 7-dihydroxy methylnaltrexone in solution following one month storage at room temperature (FIG. 2C) and at 40° C. (FIG. 2D) was assessed. The presence of CaEDTA reduced formation of 7-dihydroxy methylnaltrexone at either temperature. After one month at room temperature, the level was reduced from 0.34% to 0.11%; and at 40° C./75% RH, the level was reduced from 0.64% to 0.14%. The presence of NaEDTA in the samples may even increase levels of 7-dihydroxy methylnaltrexone formed.

(FIG. 3B) was assessed. Calcium EDTA was not effective at inhibiting formation of the 0.79 degradant, and may increase levels of degradant formation.

DETAILED DESCRIPTION OF CERTAIN EMBODIMENTS OF THE INVENTION

Figure 1A:
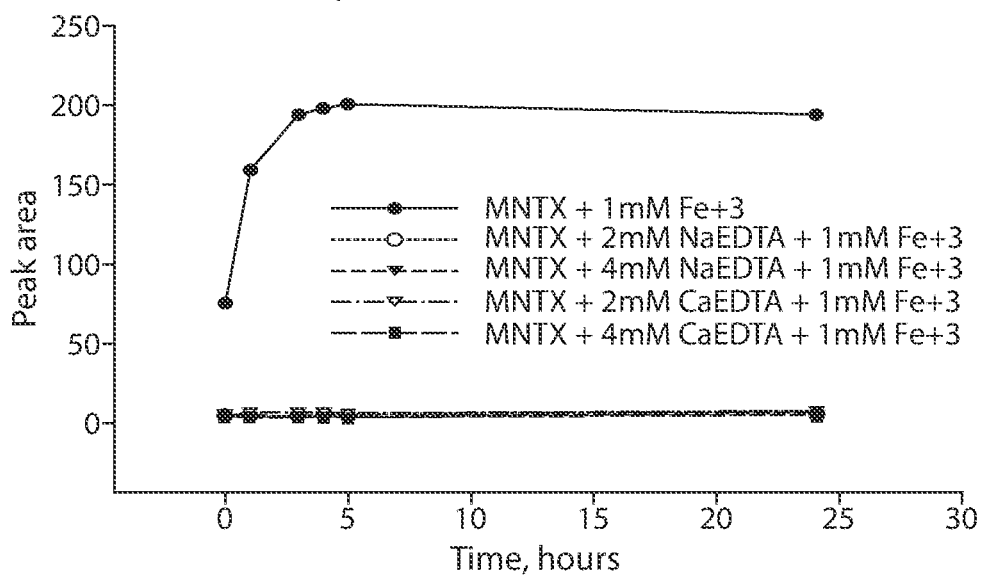
FIG. 1A and FIG. 1B: Effect of CaEDTA and NaEDTA on the formation of 2',2-bis methylnaltrexone in the presence of iron at 40° C.

Provided are pharmaceutical formulations having improved stability characteristics under certain conditions. Compositions, kits, and products including provided formulations allow for extended storage periods and also for storage under favorable room temperature conditions. Compositions and kits and products containing provided formulations thus allow for improved delivery of therapeutics to subjects benefiting from use of methylnaltrexone.

For example, provided formulations are useful to treat, prevent, delay, or decrease severity or incidence of side effects associated with opioid administration, including gastrointestinal dysfunction (e.g., constipation, bowel hypomotility, impaction, gastric hypomotility, GI sphincter constriction, increased sphincter tone, inhibition of gastrointestinal motility, inhibition of intestinal motility, inhibition of gastric emptying, delayed gastric emptying, incomplete evacuation, nausea, emesis (vomiting), bloating, abdominal distension), dysphoria, pruritis, urinary retention, depression of respiration, papillary constriction, cardiovascular effects, chest wall rigidity and cough suppression, depression of stress response, and immune suppression associated with use of narcotic analgesia, etc. Additional effects of opioid administration can include, e.g., aberrant migration or proliferation of endothelial cells (e.g., vascular endothelial cells), increased angiogenesis, and increase in lethal factor production from opportunistic infectious agents (e.g., *Pseudomonas aeruginosa*). Formulations are useful for administration to patients receiving short term treatment with opioids (e.g., patients suffering from post-operative gastrointestinal dysfunction receiving short term opioid administration). Formulations are also useful for administration to subjects receiving chronic opioid administration (e.g., terminally ill patients receiving opioid therapy such as an AIDS patient, a cancer patient, a cardiovascular patient; subjects receiving chronic opioid therapy for pain management; subjects receiving opioid therapy for maintenance of opioid withdrawal).

Further uses of provided formulations include, for example, prevention, delay, treatment or reduction of severity of symptoms associated with disorders or conditions resulting from normal or aberrant activity of endogenous opioids. Such disorders or condition include, among others, ileus (e.g., post-partum ileus, paralytic ileus), gastrointestinal dysfunction that develop following abdominal surgery (e.g., colectomy, including but not limited to, right hemicolectomy, left hemicolectomy, transverse hemicolectomy, colectomy takedown, and low anterior resection) such as post-operative ileus, and idiopathic constipation. Provided formulations are also useful in treatment of conditions including cancers involving angiogenesis, immune suppression, sickle cell anemia, vascular wounds, retinopathy, and treatment of inflammation associated disorders (e.g., irritable bowel syndrome), immune suppression, and chronic inflammation.

Definitions

The term "dose-concentrate" refers to a pharmaceutical composition comprising a provided formulation, wherein the concentration of active agent(s) is higher than a typical unit dosage form concentration administered directly to a subject. A dose-concentrate may be used as provided for administration to a subject, but is generally further diluted to a typical unit dosage form concentration in preparation for administration to a subject. The entire volume of a dose-concentrate, or aliquots thereof, may be used in preparing unit dosage form(s) for treatment, for example, by the methods provided herein. In some embodiments, a dose-concentrate is about 2 fold, about 5-fold, about 10-fold, about 25-fold, about 50-fold, about 100-fold, or about 200-fold more concentrated than a unit dosage form. In certain embodiments, a dose concentrate is about 50-fold, about 100-fold, or about 200-fold more concentrated than a unit dosage form.

As used herein, an "effective amount" of a compound or pharmaceutically acceptable formulation can achieve a desired therapeutic and/or prophylactic effect. In some embodiments, an "effective amount" is at least a minimal amount of a compound, or formulation containing a compound, which is sufficient for treating one or more symptoms of a disorder or condition associated with modulation of peripheral µ opioid receptors, such as side effects associated with opioid analgesic therapy (e.g., gastrointestinal dysfunction (e.g., dysmotility constipation, etc.), nausea, emesis, (e.g., vomiting), etc.). In certain embodiments, an "effective amount" of a compound, or formulation containing a compound, is sufficient for treating symptoms associated with, a disease associated with aberrant endogenous peripheral opioid or p opioid receptor activity (e.g., idiopathic constipation, ileus, etc.).

The term "formulation" refers to a composition that includes at least one pharmaceutically active compound (e.g., at least methylnaltrexone) in combination with one or more excipients or other pharmaceutical additives for administration to a subject. In general, particular excipients and/or other pharmaceutical additives are typically selected with the aim of enabling a desired stability, release, distribution and/or activity of active compound(s) for applications.

The term "subject", as used herein, means a mammal to whom a formulation or composition comprising a formulation is administered, and includes human and animal subjects, such as domestic animals (e.g., horses, dogs, cats, etc.).

"Therapeutically active compound" or "active compound" refers to a substance, including a biologically active substance, that is useful for therapy (e.g., human therapy, veterinary therapy), including prophylactic and/or therapeutic treatment. Therapeutically active compounds can be organic molecules that are drug compounds, peptides, proteins, carbohydrates, monosaccharides, oligosaccharides, polysaccharides, nucleoprotein, mucoprotein, lipoprotein, synthetic polypeptide or protein, small molecules linked to a protein, glycoprotein, steroid, nucleic acid, DNA, RNA, nucleotide, nucleoside, oligonucleotides, antisense oligonucleotides, lipid, hormone, and vitamin. Alternatively or additionally, therapeutically active compounds can be any substance used as a medicine for treatment, prevention, delay, reduction or amelioration of a disease, condition, or disorder. Among therapeutically active compounds useful in the formulations of the present invention are opioid antagonist compounds, opioid analgesic compounds, and the like. Further detailed description of compounds useful as therapeutically active compounds is provided below. A therapeutically active compound includes a compound that increases the effect or effectiveness of a second compound, for example, by enhancing potency or reducing adverse effects of a second compound. The terms "treat" or "treating," as used herein, refers to partially or completely alleviating, inhibiting, delaying onset of, reducing the incidence of, ameliorating and/or relieving a disorder or condition, or one or more symptoms of the disorder, disease or condition.

The expression "unit dosage" as used herein refers to a physically discrete unit of a formulation appropriate for a subject to be treated. It will be understood, however, that the total daily usage of a formulation of the present invention will be decided by the attending physician within the scope of sound medical judgment. The specific effective dose level for any particular subject or organism will depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/ or additional therapies used in combination or coincidental with specific compound(s) employed, and like factors well known in the medical arts.

The expression "dosage form" refers to means by which a formulation is stored and/or administered to a subject. For example, the formulation may be stored in a vial or syringe. The formulation may also be stored in a container which protects the formulation from light (e.g., UV light). Alternatively a container or vial which itself is not necessarily protective from light may be stored in a secondary storage container (e.g., an outer box, bag, etc.) which protects the formulation from light.

The present invention provides formulations and dosage forms for parenteral administration of methylnaltrexone, including pharmaceutically acceptable salts thereof. As used herein, "methylnaltrexone" includes N-methylnaltrexone and salts thereof. Methylnaltrexone is described for example in U.S. Pat. Nos. 4,176,186; 4,719,215; 4,861,781; 5,102, 887; 5,972,954; 6,274,591; United States published patent application numbers 20020028825 and 20030022909; and PCT publications WO99/22737 and WO98/25613; the contents of each of which are hereby incorporated by reference.

In general, pharmaceutically acceptable salts include, but are not limited to, chloride, bromide, iodide, nitrate, sulfate, bisulfate, phosphate, acid phosphate, isonicotinate, acetate, lactate, salicylate, citrate, tartrate, pantothenate, bitartrate, carbonate, ascorbate, succinate, maleate, gentisinate, fumarate, gluconate, glucaronate, saccharate, formate, carboxylate, benzoate, glutamate, sulfonate, methanesulfonate, ethanesulfonate, benzensulfonate, p-toluenesulfonate, selenate, and pamoate (i.e., 1,1'-methylene-bis-(2-hydroxy-3-naphthoate)) salts of compounds. In some embodiments, salts of use in formulations of the invention are those that have been described for methylnaltrexone, e.g., methylnaltrexone bromide, etc. However, the invention is not limited to these specific salts. Other salts and mixtures thereof can be adapted and used in a dose formulation according to the invention so as to achieve the appropriate compound delivery profiles of the invention (e.g., chloride, sulfate, bisulfate, tartrate, nitrate, citrate, bitartrate, phosphate, malate, maleate, bromide, iodide, fumarate, sulfonate, carboxylate, or succinate salts, etc.). Alternatively or additionally, peripheral opioid receptor antagonist (e.g., methylnaltrexone) base, chemical and chiral derivatives thereof and other salts can be used, as appropriate.

The bromide salt of methylnaltrexone is also referred to, for example, N-methylnaltrexone bromide, N-methylnaltrexone hydrobromide, methylnaltrexone bromide, methylnaltrexone hydrobromide, naltrexone methobromide, N-methylnaltrexone, MNTX, SC-37359, MRZ-2663-BR, and N-cyclopropylmethylnoroxy-morphine-metho-bromide. Methylnaltrexone is available in a powder form from Mallinckrodt Pharmaceuticals, St. Louis, Mo., provided as a white crystalline powder freely soluble in water. Its melting point is 254-256° C. In some embodiments, the invention provides formulations in a vial. In certain embodiments, a formulation is provided in a vial containing a unit dosage of methylnaltrexone. In such embodiments, a formulation may comprise about 0.5 mg to about 200 mg methylnaltrexone bromide. In some embodiments, a unit dosage can contain from about 1 mg to about 80 mg, from about 5 mg to about 40 mg, or from about 8 mg to 12 mg to about 18 mg to about 24 mg.

Methylnaltrexone has chiral centers and can therefore occur as stereochemical isomers by virtue of the substituent placement on those chiral centers. Such stereochemical isomers are within the scope of the compounds contemplated for use in the present formulations. In the compositions and methods of the present invention, compounds employed may be individual stereoisomers, as well as mixtures of stereoisomers. In certain aspects, methods of the present invention utilize compounds which are substantially pure stereoisomers. All tautomers are also intended to be encompassed within the compositions of the present invention.

The terms "R" and "S" are used herein, as commonly used in organic chemistry nomenclature, to denote specific configuration of a chiral center. The term "R" refers to "right" and is used to designate the configuration of a chiral center with a clockwise relationship of group priorities (highest to second lowest) when viewed along the bond toward the lowest priority group. The term "S" or "left" is used to designate the configuration of a chiral center with a counterclockwise relationship of group priorities (highest to second lowest) when viewed along the bond toward the lowest priority group. The priority of groups is based upon their atomic number (heaviest isotope first). A partial list of priorities and a discussion of stereochemistry is contained in the book: The Vocabulary of Organic Chemistry, Orchin, et al., John Wiley and Sons Inc., page 126 (1980), which is incorporated herein by reference in its entirety.

In some embodiments, isolated R—N isomers of methylnaltrexone may be utilized in formulations and methods. As used herein, the designation of "R—N-isomer" of methylnaltrexone refers to such compounds in the (R) configuration with respect to the nitrogen. Isolated isomer compounds include, but are not limited to, R—N isomer methylnaltrexone compounds described in U.S. patent application Ser. No. 11/441,395 filed May 25, 2006, published WO2006/127899, which is hereby incorporated herein by reference. In some embodiments, the active compound is an R—N isomer methylnaltrexone, or a salt thereof. The R—N isomer of methylnaltrexone has been found in U.S. Ser. No. 11/441,395 to be an opioid antagonist.

In some embodiments, isolated S—N isomers of methylnaltrexone may be utilized in formulations and methods. As used herein, the designation of "S—N-isomer" of methylnaltrexone refers to such compounds in the (S) configuration with respect to the nitrogen. Isolated isomer compounds include, but are not limited to, S—N isomer of methylnaltrexone compounds described in U.S. patent application Ser. No. 11/441,452, filed May 25, 2006, published WO2006/127898, which is hereby incorporated by reference. In some embodiments, the active compound is an S—N isomer methylnaltrexone, or a salt thereof. The S—N isomer of methylnaltrexone has been found in U.S. Ser. No. 11/441,452 to be an opioid agonist.

In certain embodiments, the methylnaltrexone of formulations described herein is a mixture of stereoisomers characterized in that it has an opioid antagonist effect. For example, the methylnaltrexone may be a mixture of R—N and S—N methylnaltrexone such that a mixture itself has an antagonist effect and would be useful for methods of use described herein for opioid antagonists. In certain embodiments, R—N methylnaltrexone is used which is substantially free of S—N methylnaltrexone.

In certain embodiments of the present invention, at least about 99.6%, 99.7%, 99.8%, 99.85%, 99.9%, or 99.95% of methylnaltrexone is in the (R) configuration with respect to nitrogen. Methods for determining the amount of (R)—N-isomer, present in a sample as compared to the amount of (S)—N-isomer present in that same sample, are described in detail in WO2006/127899, the entirety of which is hereby incorporated herein by reference. In other embodiments, methylnaltrexone contains 0.15%, 0.10%, or less (S)—N-isomer.

The exact amount of methylnaltrexone (or combination of methylnaltrexone and any other particular active agent) that is required to achieve a pharmaceutically effective amount will vary from subject to subject, depending on species, age, and general condition of a subject, severity of the side effects or disorder, identity of the particular compound(s), mode of administration, and the like. A total daily dosage of methylnaltrexone (e.g., methylnaltrexone bromide) will typically be in the range 10-200 mg, preferably 20-100 mg for a 70 kg adult human. A unit dosage formulation according to the invention will usually contain 1-250 mg of active compound (e.g., methylnaltrexone bromide) per unit, 5-100 mg of active compound per unit, 10-50 mg of active compound per unit, or about 8 mg or about 12 mg or about 24 mg of active compound per unit. In certain embodiments, an effective amount of a methylnaltrexone for administration to a 70 kg adult human may comprise about 10 mg to about 50 mg of compound (e.g., methylnaltrexone bromide) per unit dosage, to be administered one or more times a day. It will be appreciated that dose ranges set out above provide guidance for the administration of active compound to an adult. The amount to be administered to for example, an infant or a baby can be determined by a medical practitioner or person skilled in the art and can be lower or the same as that administered to an adult.

Formulations

The present invention provides formulations that are capable of maintenance of integrity of methylnaltrexone without substantial production of degradants following storage, including storage at room temperature. Thus, the provided formulations are capable of conferring improved storage stability characteristics of delivered methylnaltrexone. For example, in some embodiments, a formulation comprises methylnaltrexone, a calcium salt chelating agent, an isotonic agent, and a carrier. In some embodiments, a formulation comprises methylnaltrexone, a calcium salt chelating agent, an isotonic agent, a stabilizing agent, and a carrier. In some embodiments, the pH of the formulation is between about a pH of 2 to about a pH of 5.

The present invention provides formulations and methods for delivery of methylnaltrexone for improved storage and maintenance of pharmaceutical compositions. In particular, the present invention provides formulations that are stable formulations for parenteral administration of methylnaltrexone compositions. Formulations provided for parenteral administration may include sterile solution for injection, sterile suspension for injection, sterile emulsions, and dispersions.

For example, in some embodiments, formulations comprise methylnaltrexone, and a calcium salt-chelating agent in an isotonic solution. In some embodiments, fomulations comprise methylnaltrexone, a calcium salt chelating agent, and a stabilizing agent in an isotonic solution.

Generally, provided formulations will include one or more active compound(s) together with one or more excipients, such as, for example, one or more chelating agents, a calcium ion, isotonic agents, carriers, buffers, co-solvents, diluents, preservatives, and/or surfactants, or combinations thereof. One skilled in the art will readily appreciate that the same ingredient can sometimes perform more than one function, or can perform different functions in the context of different formulations, and/or portions of a formulation, depending upon the amount of the ingredient and/or the presence of other ingredients and/or active compound(s). Active compound may comprise about 0.5 mg to about 200 mg methylnaltrexone bromide. In some embodiments, active compound may comprise about 1 mg to about 80 mg, from about 5 mg to about 40 mg, or about 8, or about 12 mg, about 16 mg, about 18 mg, or about 24 mg methylnaltrexone bromide.

In some embodiments, the formulation comprises a chelating agent. In some embodiments, a chelating agent may be present in an amount from about 0.01 mg/mL to about 2 mg/mL or about 0.1 mg/mL to about 1 mg/mL in the formulation, or about 0.2 mg/mL to about 0.8 mg/mL of the formulation. In some embodiments, a chelating agent may be present in an amount from about 0.2 mg/mL, about 0.3 mg/mL, about 0.4 mg/mL, about 0.5 mg/mL, or about 0.6 mg/mL, in the formulation.

We have found use of a chelating agent is effective as inhibiting at least one degradant formation. Thus, addition of at least one chelating agent is particularly useful in formulations that include methylnaltrexone, and provides protection from metal-catalyzed degradant production, and/or from precipitation. Appropriate chelating agents include any pharmaceutically acceptable chelating agents and salts thereof. Examples of chelating agents include, but are not limited to ethylenediaminetetraacetic acid (also synonymous with EDTA, edetic acid, versene acid, and sequestrene), and EDTA derivatives, such as sodium EDTA, and potassium EDTA, diammonium EDTA, dipotassium EDTA, disodium EDTA, TEA-EDTA, tetrasodium EDTA, tripotassium EDTA, trisodium EDTA, HEDTA, and trisodium HEDTA, and related salts thereof. Other chelating agents include niacinamide and derivatives thereof and sodium desoxycholate and derivatives thereof, ethylene glycol-bis-(2-aminoethyl)-N,N,N', N'-tetraacetic acid (EGTA) and derivatives thereof, diethylenetriaminepentaacetic acid (DTPA) and derivatives thereof, N,N-bis(carboxymethyl)glycine (NTA) and derivatives thereof, nitrilotriacetic acid and derivatives thereof. Still other chelating agents include citric acid and derivatives thereof. Citric acid also is known as citric acid monohydrate. Derivatives of citric acid include anhydrous citric acid and trisodiumcitrate-dihydrate. In some embodiments, chelating agent is selected from EDTA or an EDTA derivative or EGTA or an EGTA derivative. In some embodiments chelating agent is EDTA disodium such as, for example, EDTA disodium hydrate.

In some embodiments, a provided formulation comprises a calcium salt. In some embodiments, a calcium salt may be present in an amount from about 0.01 mg/mL to about 2 mg/mL or about 0.1 mg/mL to about 1 mg/mL in the formulation, or about 0.2 mg/mL to about 0.8 mg/mL of the formulation. In some embodiments, a calcium salt may be present in an amount from about 0.2 mg/mL, about 0.3 mg/mL, about 0.4 mg/mL, about 0.5 mg/mL, or about 0.6 mg/mL, in the formulation.

We have found the presence of a calcium ion is effective as inhibiting formation of at least one degradant. Thus, addition of at least one calcium salt is particularly useful in formulations that include methylnaltrexone, and provides protection from metal-catalyzed degradant production, and/or from precipitation. Appropriate calcium salts include any pharmaceutically acceptable calcium salts. Examplary of calcium salts include, but are not limited to calcium chloride, calcium acetate, calcium citrate, calcium sulfate, etc.

In some embodiments, a formulation comprises a calcium ion and a chelating agent included as a single component of the formulation. Thus in some embodiments a calcium salt chelating agent may be present in an amount from about 0.01 mg/mL to about 2 mg/mL or about 0.1 mg/mL to about 1 mg/mL in the formulation, or about 0.2 mg/mL to about 0.8 mg/mL of the formulation. In some embodiments, calcium salt chelating agent may be present in an amount from about 0.2 mg/mL, about 0.3 mg/mL, about 0.4 mg/mL, about 0.5 mg/mL, or about 0.6 mg/mL, in the formulation.

We have found use of a calcium salt chelating agent is particularly effective as inhibiting formation of at least one degradant. Thus, addition of at least one calcium salt chelating agent is particularly useful in formulations that include methylnaltrexone, and provides protection from metal-catalyzed production of 2,2' bis-methylnaltrexone, and 7-dihydroxy methylnaltrexone, and/or from precipitation. In some embodiments, the formulation comprises a calcium salt chelating agent.

Appropriate calcium salt chelating agents include any pharmaceutically acceptable chelating agents and calcium salts thereof. Common calcium salt chelating agents include, but are not limited to calcium ethylenediaminetetra acetic acid (EDTA) and calcium salt EDTA derivatives, calcium ethylene glycol-bis-(2-aminoethyl)-N,N,N', N'-tetraacetic acid (EGTA) and calcium salt EGTA derivatives, calcium diethylenetriaminepentaacetic acid (DTPA) and calcium salt DTPA derivatives, calcium N,N-bis(carboxymethyl)glycine (NTA) and calcium salt NTA derivatives, and calcium citrate and derivatives thereof. In some embodiments, chelating agent is selected from calcium EDTA or a calcium salt EDTA derivative or calcium EGTA or a calcium salt EGTA derivative. In some embodiments chelating agent is calcium EDTA disodium such as, for example, calcium EDTA disodium hydrate.

In some embodiments, a provided formulation comprises at least methylnaltrexone, a calcium salt chelating agent and an isotonic agent. An isotonic agent useful in the present formulations can be any pharmaceutically acceptable isotonic agent. Common isotonic agents include agents selected from the group consisting of sodium chloride, mannitol, lactose, dextrose (hydrous or anhydrous), sucrose, glycerol, and sorbitol, and solutions of the foregoing. In certain embodiments, the formulation comprises methylnaltrexone, an isotonic agent which is sodium chloride, and a calcium salt chelating agent which is calcium EDTA or a calcium salt EDTA derivative. In some embodiments, the EDTA is calcium EDTA disodium.

In some embodiments, the formulation comprises at least methylnaltrexone, an isotonic agent, a calcium salt chelating agent and a carrier vehicle. In certain embodiments, the carrier vehicle is an aqueous carrier. Aqueous carrier vehicles are known in the art, and include, but are not limited to sterile water, water for injection, sodium chloride, Ringer's injection, isotonic dextrose injection, dextrose and lactated Ringers injection. In some embodiments, the formulation comprises water for injection. In some embodiments, formulations comprise methylnaltrexone or a pharmaceutically acceptable salt thereof, calcium EDTA or a calcium salt EDTA derivative, water for injection, and sodium chloride in an amount such that the final solution is isotonic (e.g., 0.1%, 0.25%, 0.45% 0.65%, 0.9% sodium chloride). In some embodiments, the sodium chloride is present in an isotonic amount, such that final concentration of sodium chloride is 0.65%.

Still additional components such as stabilizing agents, buffers, co-solvents, diluents, preservatives, and/or surfactants, etc. may be included in provided formulations. In some embodiments, formulations may contain such additional agents which comprise from about 1% to about 30% or about 1% to about 12% of the formulation or about 1% to about 10%, based upon total weight of the formulation. In some embodiments, additional agents may comprise from about 1%, about 2%, about 5%, about 8% or about 10% of the formulation, based upon total weight of the formulation. Optionally included additional ingredients are described below.

In some embodiments, provided formulations comprise a stabilizing agent. In some embodiments, stabilizing agent may be present in an amount from about 0.01 mg/mL to about 2 mg/mL or about 0.05 mg/mL to about 1 mg/mL in the formulation, or about 0.1 mg/mL to about 0.8 mg/mL in the formulation. In some embodiments, stabilizing agent may be present in an amount from about 0.15 mg/mL, about 0.2 mg/mL, about 0.25 mg/mL, about 0.3 mg/mL, about 0.35 mg/mL, or about 0.4 mg/mL.

Suitable stabilizing agents for use in formulations of the invention include, but are not limited to glycine, benzoic acid, citric, glycolic, lactic, malic, and maleic acid. In some embodiments, the formulation comprises glycine. In some embodiments, glycine comprises glycine-HCl. In some embodiments, formulations comprise methylnaltrexone, calcium EDTA or a calcium salt EDTA derivative, water for injection, sodium chloride in an amount such that the final concentration is 6.5 mg/mL isotonic sodium chloride, and glycine such as glycine HCl.

In certain embodiments, a stabilizing agent is added to the formulation in an amount sufficient to adjust and maintain the pH of the formulation. Thus, in some embodiments, a stabilizing agent acts as a buffer function in addition to its role as a stabilizer. In some embodiments, a stabilizing agent may act as a buffer agent, so as to maintain the pH of the formulation. In certain embodiments, the pH is between about pH 2.0 and about pH 6.0. In some embodiments, the pH of the formulation is between about pH 2.6 and about pH 5.0. In some embodiments, the pH of the formulation is between about pH 3.0 and about pH 4.0. In some embodiments, the pH of the formulation is between about pH 3.4 and about pH 3.6. In some embodiments, the pH of the formulation is about pH 3.5.

In some embodiments, provided formulations comprise methylnaltrexone, calcium EDTA or a calcium salt EDTA derivative, water for injection, sodium chloride in an amount such that the final concentration is 6.5 mg/mL isotonic sodium chloride, glycine, and the pH of the formulation is between about pH 3.0 and about pH 4.0. In some embodiments, formulations comprise methylnaltrexone or a pharmaceutically acceptable salt thereof, calcium EDTA or a calcium salt EDTA derivative, water for injection, sodium chloride in an amount such that the final concentration is 6.5 mg/mL isotonic sodium chloride, glycine, and the pH of the formulation is between about pH 3.4 and about pH 3.6. In some embodiments, formulations comprise methylnaltrexone bromide, calcium EDTA or a calcium salt EDTA derivative, water for injection, sodium chloride in an amount such that the final concentration is 6.5 mg/mL isotonic sodium chloride, and glycine, and the formulation has a pH of about 3.5. In certain embodiments, the pH is adjusted with glycine. In some embodiments, glycine is glycine HCl.

In some embodiments, provided formulations comprise methylnaltrexone bromide, calcium EDTA, water for injection, isotonic sodium chloride, glycine HCl, and the formulation has a pH between about 3.4 and about 3.6. In some embodiments, provided formulations comprise methylnaltrexone bromide at a concentration about 20 mg/mL, calcium EDTA at a concentration about 0.4 mg/mL, sodium chloride in an amount such that the final concentration is 6.5 mg/mL isotonic sodium chloride, and glycine HCl at a concentration about 0.3 mg/mL, and the formulation has a pH of about 3.5. In some embodiments, formulations comprise methylnaltrexone bromide at a concentration about 10 mg/mL, calcium EDTA at a concentration about 0.2 mg/mL, sodium chloride in an amount such that the final concentration is 3.25 mg/mL isotonic sodium chloride, and glycine HCl at a concentration about 0.15 mg/mL, and the formulation has a pH of about 3.5.

One of ordinary skill in the art will recognize that additional pH adjustments may be required to ensure that a provided formulation has desired pH. Thus, in certain embodiments, further pH adjustment is performed with hydrochloric acid and/or sodium hydroxide.

Additional Components

In some embodiments, formulations may comprise one or more additional agents for modification and/or optimization of release and/or absorption characteristics. For example, as mentioned above, incorporation of buffers, co-solvents, diluents, preservatives, and/or surfactants may facilitate dissolution, absorption, stability, and/or improved activity of active compound(s), and may be utilized in formulations of the invention. In some embodiments, where additional agents are included in a formulation, the amount of additional agents in the formulation may optionally include: buffers about 10% to about 90%, co-solvents about 1% to about 50%, diluents about 1% to about 10%, preservative agents about 0.1% to about 8%, and/or surfactants about 1% to about 30%, based upon total weight of the formulation, as applicable.

Suitable co-solvents (i.e., water miscible solvents) are known in the art. For example, suitable co-solvents include, but are not limited to ethyl alcohol, propylene glycol.

Physiologically acceptable diluents may optionally be added to improve product characteristics. Physiologically acceptable diluents are known in the art and include, but are not limited to, sugars, inorganic salts and amino acids, and solutions of any of the foregoing. Representative examples of acceptable diluents include dextrose, mannitol, lactose, and sucrose, sodium chloride, sodium phosphate, and calcium chloride, arginine, tyrosine, and leucine, and the like, and aqueous solutions thereof.

Suitable preservatives are known in the art, and include, for example, benzyl alcohol, methyl paraben, propyl paraben, sodium salts of methyl paraben, thimerosal, chlorobutanol, phenol. Suitable preservatives include but are not limited to: chlorobutanol (0.3-0.9% W/V), parabens (0.01-5.0% W/V), thimerosal (0.004-0.2% W/V), benzyl alcohol (0.5-5% W/V), phenol (0.1-1.0% W/V), and the like.

Suitable surfactants are also known in the art and include, e.g., poloxamer, polyoxyethylene ethers, polyoxyethylene sorbitan fatty acid esters polyoxyethylene fatty acid esters, polyethylene glycol fatty acid esters, polyoxyethylene hydrogenated castor oil, polyoxyethylene alkyl ether, polysorbates, cetyl alcohol, glycerol fatty acid esters (e.g., triacetin, glycerol monostearate, and the like), polyoxymethylene stearate, sodium lauryl sulfate, sorbitan fatty acid esters, sucrose fatty acid esters, benzalkonium chloride, polyethoxylated castor oil, and docusate sodium, and the like, and combinations thereof. In some embodiments the formulation may further comprise a surfactant.

Dosage Forms

As indicated, the present invention provides dosage forms including unit dosage forms, dose-concentrates, etc. for parenteral administration. Parenteral administration of provided formulations may include any of intravenous injection, intravenous infusion, intradermal, intralesional, intramuscular, subcutaneous injection or depot administration of a unit dose. A unit dosage may or may not constitute a single "dose" of active compound(s), as a prescribing doctor may choose to administer more than one, less than one, or precisely one unit dosage in each dose (i.e., each instance of administration). For example, unit dosages may be administered once, less than once, or more than once a day, for example, once a week, once every other day (QOD), once a day, or 2, 3 or 4 times a day, more preferably 1 or 2 times per day.

In certain embodiments, a provided dosage form is administered to a rehab patient (patients undergoing rehabilitation for orthopaedic surgery, e.g. joint replacement) every other day or every day. In other embodiments, provided dosage is 12 mg methylnaltrexone.

In certain embodiments, a provided dosage form is administered to a chronic pain patient every other day or every day. In some embodiments, the pain is malignant or nonmalignant. In other embodiments, provided dosage is 12 mg methylnaltrexone.

The present invention provides variety of different dosage forms useful for parenteral administration, including, for example, a methylnaltrexone formulation provided in a container (e.g., a vial, ampoule, syringe, bag, dispenser, etc).

In one embodiment, the formulation is in a vial filled with methylnaltrexone solution, where the solution comprises at least one active compound which is methylnaltrexone, and a calcium salt chelating agent, in an isotonic solution. In one embodiment, a provided formulation is in a vial where the vial is filled with a provided formulation, as described above and herein. In some embodiments, provided formulation is in a vial from about 1 mL capacity to about 50 mL capacity. In some embodiments, a vial is about 1 mL, about 2 mL, about 5 mL, about 10 mL, about 25 mL or about 50 mL capacity.

In one embodiment, a provided formulation is in a syringe or other dispenser filled a provided formulation as described above and herein. In some embodiments, a syringe or dispenser has a capacity from about 1 mL to about 20 mL. In some embodiments a syringe or dispenser has a capacity of about 1 mL, about 2 mL, about 2.5 mL, about 5 mL, about 7.5 mL, about 10 mL, about 15 mL, or about 20 mL. In some embodiments, a syringe or dispenser utilizes a hypodermic needle for administration of contents of the syringe or dispenser to a subject. In certain embodiments, a syringe or dispenser utilized a needle-less adapter for transfer of contents of the container to a subject, or, alternatively to a second container for mixing and/or dilution of contents with another solution. A dose-concentrate of a provided formulation can be in a sealed container holding an amount of the pharmaceutical formulation of the invention to be employed over a standard treatment interval such as immediately upon dilution, or up to 24 hours after dilution, as necessary. A solution for intravenous administration can be prepared, for example, by adding a dose-concentrate formulation to a container (e.g., glass or plastic bottles, vials, ampoules) in combination with diluent so as to achieve desired concentration for administration. The amount of dose concentrate added to diluent is a sufficient amount to treat a subject for a period ranging from about 6 hours to about 1 week, but preferably from about 6 or 12 hours to about 24 hours. The container preferably also contains an empty space of sufficient size to permit (i) addition of aqueous solvent plus (ii) additional space as necessary to permit agitation and effect complete mixture of diluted dose concentrate formulation with the added aqueous solvent. A container may be equipped with a penetrable or spikable top, for example, a rubber seal, such that aqueous solvent may be added by penetrating the seal with a hypodermic syringe or other type non-needle based, penetrable seal in order to transfer concentrate contents. In certain embodiments, a provided formulation is provided in a spikable vial. In some embodiments, a provided formulation is provided in a 10 mL spikable vial.

Addition of aqueous solvent to a liquid dose concentrate may be conveniently used to form unit dosages of liquid pharmaceutical formulations by removing aliquot portions or entire contents of a dose concentrate for dilution. Dose concentrate may be added to an intravenous (IV) container containing a suitable aqueous solvent. Useful solvents are standard solutions for injection as previously described (e.g., 5% dextrose, saline, lactated ringer's, or sterile water for injection, etc.). Typical unit dosage IV bags are conventional glass or plastic containers having inlet and outlet means and having standard (e.g., 25 mL, 50 mL, 100 mL and 150 mL) capacities. Dose concentrate solution of a pharmaceutical formulation of the invention is added to a unit dosage IV container in an amount to achieve a concentration of about 0.1 to about 1.0 mg of methylnaltrexone per mL and preferably from about 0.24 to about 0.48 mg per mL.

In other embodiments, it may be desirable to package a provided dosage form in a container to protect the formulation from light until usage. In some embodiments, use of such a light-protective container may inhibit one or more degradation pathways. For example, a vial may be a light container which protects contents from being exposed to light. Additionally and/or alternatively, a vial may be packaged in any type of container which protects a formulation from being exposed to light (e.g., secondary packaging of a vial). Similarly, any other type of container may be a light protective container, or packaged within a light protective container.

Preparation of Provided Formulations

Formulations of the present invention may be prepared in accordance with any of a variety of known techniques, for example as described by M. E. Aulton in "Pharmaceutics:

The Science of Dosage Form Design" (1988) (Churchill Livingstone), the relevant disclosures of which are hereby incorporated by reference.

In one embodiment, a provided formulation is prepared as follows: dry components of a formulation, including active compound (e.g., methylnaltrexone bromide), and calcium salt chelating agent (e.g., calcium EDTA) are dissolved in an appropriate solvent (e.g., an isotonic solution (e.g., isotonic sodium chloride for injection)). Optionally, additional dry and/or wet ingredients (e.g., solvent (e.g., water)), stabilizing agent, or surfactant, may be added. Optionally, additional components, such as stabilizing agents, or surfactants are added to solvent prior to dissolving other components. A provided formulation may be prepared under low oxygen conditions.

In another embodiment, a provided formulation is prepared as follows: dry components of a formulation, including active compound (e.g., methylnaltrexone bromide), and calcium salt chelating agent (e.g., calcium EDTA) are dissolved in an appropriate solvent (e.g., an isotonic solution (e.g., isotonic sodium chloride for injection)). Alternatively, dry components of a formulation, including active compound (e.g., methylnaltrexone bromide), and isotonic agent (e.g., sodium chloride) are dissolved in an aqueous solvent (e.g., water for injection) to generate an active compound in an isotonic solution (e.g., methylnaltrexone in isotonic sodium chloride for injection), followed by further addition and dissolution of calcium salt chelating agent (e.g., calcium EDTA) to the solution. Next, the pH of the solution may be adjusted. For example, addition of glycine may adjust the pH to the desired level. For example, addition of glycine HCl may be utilized for addition to the solution to adjust pH to a desired pH (e.g., pH 3-4, pH 3.4-3.6, pH 3.5). Optionally, additional dry and/or wet ingredients (e.g., solvent (e.g., water), stabilizing agent (e.g., glycine), or surfactant, may be added. Optionally, additional components, such as stabilizing agents, surfactants are added to solvent prior to dissolving other components. A provided formulation may be prepared under low oxygen conditions.

In one embodiment, prepared formulations are incorporated into vials, ampoules, syringes, or dispensers, either alone, or with additional excipients. Typical excipients added to a provided formulation include, but are not limited to surfactants, preservatives, diluents, buffers, co-solvents, etc. Typical amounts of additional excipients added to a solution may include, for example, buffers about 10% to about 90%, co-solvents about 1% to about 50%, diluents about 1% to about 10%, preservative agents about 0.1% to about 8%, and surfactants about 1% to about 30%, based upon total weight.

A prepared formulation may be subjected to a filtration process in advance of packaging. The filtration process may include, for example in the case of injection preparations, a sterilizing filtration and/or an ultra filtration of the processing solution before packaging to eliminate microorganisms or other contaminating matter from the processing solution.

A prepared formulation may be subjected to a distributing process to vials (e.g., clear glass vial, amber vials), ampoules, syringes, or dispensers (e.g., auto-dispensers). The distributing process includes, for example in the case of vial packaging, a process distributing a suitable volume of the solution into vials taking the concentration of methylnaltrexone into consideration in order that contained products carry a desired amount of methylnaltrexone.

Isolation and Identification of Degradant Products

We have identified degradants occurring in methylnaltrexone solutions, as well as certain catalysis routes for formation of degradant(s). Still further, in certain respects, we have identified means to control formation of degradants, thus resulting in lower levels of degradants in liquid formulations containing methylnaltrexone. Provided in further detail in the Example 1 herein are methods and results of such identification, including structures of resulting degradant compounds. Additional Examples further provide characterization of prepared solutions, and identification of mechanisms of catalysis of formation and/or inhibition of formation of degradants.

Thus, provided are methods for determining the presence of one or more degradants in methylnaltrexone formulations. In certain embodiments, methods of detection of degradants below a designated level are preferred for production of a methylnaltrexone formulation. Detection of individual degradant formation in a methylnaltrexone formulation by HPLC analysis and determining a formulation comprises one or more degradants below a specified level are preferred. In some embodiments the method provides analyzing a methylnaltrexone formulation by HPLC analysis and determining that the level of one or more specified degradants is not exceeded. Preferred concentration levels which are not exceeded for one or more degradants are described in the following paragraphs relating to levels of degradants in provided formulations.

Further provided are formulations which inhibit formation of methylnaltrexone degradant(s), and confer improved stability characteristics to formulations and compositions and products containing methylnaltrexone formulations. In some embodiments, methylnaltrexone formulations are provided wherein the concentration of total degradation products does not exceed about 2% of methylnaltrexone in the preparation following twelve or eighteen months of storage conditions. In some embodiments, methylnaltrexone formulations are provided wherein the concentration of total degradation products does not exceed about 1.5% of methylnaltrexone in the preparation following twelve or eighteen months of storage conditions. In more particular embodiments, methylnaltrexone formulations are provided wherein the concentration of total degradation products does not exceed about 1% of methylnaltrexone in the preparation following twelve or eighteen months of storage conditions. Preferred storage conditions include room temperature storage.

In some embodiments, methylnaltrexone formulations are provided wherein the concentration of total degradation products does not exceed about 1.5% of methylnaltrexone in the preparation following six months of room temperature storage conditions. In some embodiments, methylnaltrexone formulations are provided wherein the concentration of total degradation products does not exceed about 1% of methylnaltrexone in the preparation following six months of room temperature storage conditions. In more particular embodiments, methylnaltrexone formulations are provided wherein the concentration of total degradation products does not exceed about 0.5% of methylnaltrexone in the preparation following six months of room temperature storage conditions.

In some embodiments, methylnaltrexone formulations are provided wherein the concentration of 2,2' bis-methylnaltrexone degradant product (RRT 1.55) does not exceed about 0.5% of methylnaltrexone in the preparation following six months of room temperature storage conditions. In some embodiments, methylnaltrexone formulations are provided wherein the concentration 2,2' bis-methylnaltrexone degradant product (RRT 1.55) does not exceed about 0.2% of methylnaltrexone in the preparation following six months of room temperature storage conditions. In more particular embodiments, methylnaltrexone formulations are provided wherein the concentration of 2,2' bis-methylnaltrexone degradant product (RRT 1.55) does not exceed about 0.1% of methylnaltrexone in the preparation following six months of room temperature storage conditions.

In some embodiments, methylnaltrexone formulations are provided wherein the concentration of 7-dihydroxymethylnaltrexone degradant product (RRT 0.67) does not exceed about 0.5% of methylnaltrexone in the preparation following six months of room temperature storage conditions. In some embodiments, methylnaltrexone formulations are provided wherein the concentration 7-dihydroxymethylnaltrexone degradant product (RRT 0.67) does not exceed about 0.2% of methylnaltrexone in the preparation following six months of room temperature storage conditions. In more particular embodiments, methylnaltrexone formulations are provided wherein the concentration of 7-dihydroxymethylnaltrexone degradant product (RRT 0.67) does not exceed about 0.1% of methylnaltrexone in the preparation following six months of room temperature storage conditions.

In some embodiments, methylnaltrexone formulations are provided wherein the concentration of the ring contracted methylnaltrexone degradant product (RRT 0.79) does not exceed about 0.5% of methylnaltrexone in the preparation following six months of room temperature storage conditions. In some embodiments, methylnaltrexone formulations are provided wherein the concentration the ring contracted methylnaltrexone degradant product (RRT 0.79) does not exceed about 0.2% of methylnaltrexone in the preparation following six months of room temperature storage conditions. In more particular embodiments, methylnaltrexone formulations are provided wherein the concentration of the ring contracted methylnaltrexone degradant product (RRT 0.79) does not exceed about 0.1% of methylnaltrexone in the preparation following six months of room temperature storage conditions.

In some embodiments, methylnaltrexone formulations are provided wherein the concentration of the aldol dimer methylnaltrexone degradant product (RRT 1.77) does not exceed about 0.5% of methylnaltrexone in the preparation following six months of room temperature storage conditions. In some embodiments, methylnaltrexone formulations are provided wherein the concentration the aldol dimer methylnaltrexone degradant product (RRT 1.77) does not exceed about 0.2% of methylnaltrexone in the preparation following six months of room temperature storage conditions. In more particular embodiments, methylnaltrexone formulations are provided wherein the concentration of the aldol dimer methylnaltrexone degradant product (RRT 1.77) does not exceed about 0.1% of methylnaltrexone in the preparation following six months of room temperature storage conditions.

In some embodiments, methylnaltrexone formulations are provided wherein the concentration of the Hoffman elimination methylnaltrexone degradant product (RRT 2.26) does not exceed about 0.5% of methylnaltrexone in the preparation following six months of room temperature storage conditions. In some embodiments, methylnaltrexone formulations are provided wherein the concentration the Hoffman elimination methylnaltrexone degradant product (RRT 2.26) does not exceed about 0.2% of methylnaltrexone in the preparation following six months of room temperature storage conditions. In more particular embodiments, methylnaltrexone formulations are provided wherein the concentration of the Hoffman elimination methylnaltrexone degradant product (RRT 2.26) does not exceed about 0.1% of methylnaltrexone in the preparation following six months of room temperature storage conditions.

In some embodiments, methylnaltrexone formulations are provided wherein the concentration of O-methyl methylnaltrexone (RRT 1.66) does not exceed about 0.5% of methylnaltrexone in the preparation following six months of room temperature storage conditions. In some embodiments, methylnaltrexone formulations are provided wherein the concentration O-methyl methylnaltrexone (RRT 1.66) does not exceed about 0.25% of methylnaltrexone in the preparation following six months of room temperature storage conditions. In more particular embodiments, methylnaltrexone formulations are provided wherein the concentration of O-methyl methylnaltrexone (RRT 1.66) does not exceed about 0.15% of methylnaltrexone in the preparation following six months of room temperature storage conditions.

In some embodiments, methylnaltrexone formulations where the amount of S—N methyl naltrexone in the starting formulation is less than 0.5 wt % (relative to the total amount of methylnaltrexone) are provided wherein the concentration of the S-methylnaltrexone degradant product (RRT 0.89) does not exceed about 0.5% of methylnaltrexone in the preparation following six months of room temperature storage conditions. In some embodiments, methylnaltrexone formulations are provided wherein the concentration the S-methylnaltrexone degradant product (RRT 0.89) does not exceed about 0.2% of methylnaltrexone in the preparation following six months of room temperature storage conditions. In more particular embodiments, methylnaltrexone formulations are provided wherein the concentration of the S-methylnaltrexone degradant product (RRT 0.89) does not exceed about 0.1% of methylnaltrexone in the preparation following six months of room temperature storage conditions.

In some embodiments, methylnaltrexone formulations are provided wherein the concentration of total degradation products does not exceed about 1.25% of methylnaltrexone in the preparation following six months of room temperature storage conditions, the concentration 2,2' bis-methylnaltrexone degradant product (RRT 1.55) does not exceed about 0.2% of methylnaltrexone, wherein the concentration 7-dihydroxymethylnaltrexone degradant product (RRT 0.67) does not exceed about 0.2% of methylnaltrexone, the concentration the ring contracted methylnaltrexone degradant product (RRT 0.79) does not exceed about 0.2% of methylnaltrexone, the aldol dimer methylnaltrexone degradant product (RRT 1.77) does not exceed about 0.2% of methylnaltrexone, the Hoffman elimination methylnaltrexone degradant product (RRT 2.26) does not exceed about 0.2% of methylnaltrexone, and the concentration of O-methyl methylnaltrexone (RRT 1.66) does not exceed about 0.25% of methylnaltrexone in the preparation following six months of room temperature storage conditions.

In some embodiments, methylnaltrexone formulations are provided wherein the concentration of total degradation products does not exceed about 0.75% of methylnaltrexone in the preparation following six months of room temperature storage conditions, the concentration of 2,2' bis-methylnaltrexone degradant product (RRT 1.55) does not exceed about 0.1% of methylnaltrexone, wherein the concentration of 7-dihydroxymethylnaltrexone degradant product (RRT 0.67) does not exceed about 0.1% of methylnaltrexone, the concentration of the ring contracted methylnaltrexone degradant product (RRT 0.79) does not exceed about 0.15% of methylnaltrexone, the concentration of aldol dimer methylnaltrexone degradant product (RRT 1.77) does not exceed about 0.05% of methylnaltrexone, the concentration of the Hoffman elimination methylnaltrexone degradant product (RRT 2.26) does not exceed about 0.1% of methylnaltrexone, and the concentration of O-methyl methylnaltrexone (RRT 1.66) does not exceed about 0.15% of methylnaltrexone in the preparation following six months of room temperature storage conditions.

In other embodiments, methylnaltrexone formulations are provided wherein the concentration of 2,2' bis-methylnaltrexone degradant product (RRT 1.55) does not exceed about 0.2% of methylnaltrexone, wherein the concentration of 7-dihydroxymethylnaltrexone degradant product (RRT 0.67) does not exceed about 0.2% of methylnaltrexone, the concentration of the ring contracted methylnaltrexone degradant product (RRT 0.79) does not exceed about 0.2% of methylnaltrexone, and the concentration of the Hoffman elimination methylnaltrexone degradant product (RRT 2.26) does not exceed about 0.2% of methylnaltrexone in the preparation following six months of room temperature storage conditions.

Combination Products and Combined Administration

In some embodiments, formulations include one or more other active compounds in addition to methylnaltrexone. In such combination formulations, additional compound(s) may be included in one or more portion(s) that includes methylnaltrexone, may be missing from one or more portions that include methylnaltrexone, and/or may be included in one or more portions that does not include methylnaltrexone. Specifically, the invention encompasses formulations that deliver at least methylnaltrexone and at least one other active compound. Additionally, the invention encompasses formulations that deliver at least two independent portions of methylnaltrexone, and that further deliver at least one other active compound(s).

In some embodiments, formulations comprise both an opioid and methylnaltrexone (e.g., a μ opioid receptor antagonist). Such combination products, containing both an opioid and an opioid antagonist, would allow simultaneous relief of pain and minimization of opioid-associated side effects (e.g., gastrointestinal effects (e.g., delayed gastric emptying, altered GI tract motility), etc.).

Opioids useful in treatment of analgesia are known in the art. For example, opioid compounds include, but are not limited to, alfentanil, anileridine, asimadoline, bremazocine, burprenorphine, butorphanol, codeine, dezocine, diacetylmorphine (heroin), dihydrocodeine, diphenoxylate, ethylmorphine, fedotozine, fentanyl, funaltrexamine, hydrocodone, hydromorphone, levallorphan, levomethadyl acetate, levorphanol, loperamide, meperidine (pethidine), methadone, morphine, morphine-6-glucoronide, nalbuphine, nalorphine, nicomorphine, opium, oxycodone, oxymorphone, papaveretum, pentazocine, propiram, propoxyphene, remifentanyl, sufentanil, tilidine, trimebutine, and tramadol. In some embodiments the opioid is at least one opioid selected from alfentanil, buprenorphine, butorphanol, codeine, dezocine, dihydrocodeine, fentanyl, hydrocodone, hydromorphone, levorphanol, meperidine (pethidine), methadone, morphine, nalbuphine, nicomorphine, oxycodone, oxymorphone, papaveretum, pentazocine, propiram, propoxyphene, sufentanil and/or tramadol. In certain embodiments, the opioid is selected from morphine, codeine, oxycodone, hydrocodone, dihydrocodeine, propoxyphene, fentanyl, tramadol, and mixtures thereof. In a particular embodiment, the opioid is loperamide. In another particular embodiment, the opioid is hydromorphone. In other embodiments, the opioid is a mixed agonist such as butorphanol. In some embodiments, the subjects are administered more than one opioid, for example, morphine and heroin or methadone and heroin.

The amount of additional active compound(s) present in combination compositions of this invention will typically be no more than the amount that would normally be administered in a composition comprising that active compound as the only therapeutic agent. In certain embodiments, the amount of additional active compound will range from about 50% to 100% of the amount normally present in a composition comprising that compound as the only therapeutic agent.

In certain embodiments, formulations may also be used in conjunction with and/or in combination with additional active compounds and/or conventional therapies for treatment of gastrointestinal dysfunction to aid in the amelioration of constipation and bowel dysfunction, For example, conventional therapies include, but may not be limited to functional stimulation of the intestinal tract, stool softening agents, laxatives (e.g., diphelymethane laxatives, cathartic laxatives, osmotic laxatives, saline laxatives, etc), bulk forming agents and laxatives, lubricants, intravenous hydration, and nasogastric decompression.

Kits and Uses of Formulations

Uses

As discussed above, the present invention provides formulations useful in antagonizing undesirable side effects of opioid analgesic therapy (e.g., gastrointestinal effects (e.g., delayed gastric emptying, altered GI tract motility), etc.). Furthermore, formulations of the invention may be used to treat subjects having disease states that are ameliorated by binding μ opioid receptors, or in any treatment wherein temporary suppression of the μ opioid receptor system is desired (e.g., ileus, etc.). In certain embodiments, methods of use of formulations are in human subjects.

Accordingly, administration of provided formulations may be advantageous for treatment, prevention, amelioration, delay or reduction of side effects of opioid administration, such as, for example, gastrointestinal dysfunction (e.g., inhibition of intestinal mobility, constipation, GI sphincter constriction, nausea, emesis (vomiting), biliary spasm, opioid bowel dysfunction, colic) dysphoria, pruritis, urinary retention, depression of respiration, papillary constriction, cardiovascular effects, chest wall rigidity and cough suppression, depression of stress response, and immune suppression associated with use of narcotic analgesia, etc, or combinations thereof. Use of provided formulations may thus be beneficial from a quality of life standpoint for subjects receiving administration of opioids, as well as to reduce complications arising from chronic constipation, such as hemorrhoids, appetite suppression, mucosal breakdown, sepsis, colon cancer risk, and myocardial infarction.

In some embodiments, provided formulations are useful for administration to a subject receiving short term opioid administration. In some embodiments, provided formulations are useful for administration to patients suffering from post-operative gastrointestinal dysfunction.

In other embodiments, provided formulations are also useful for administration to subjects receiving chronic opioid administration (e.g., terminally ill patients receiving opioid therapy such as an AIDS patient, a cancer patient, a cardiovascular patient; subjects receiving chronic opioid therapy for pain management; subjects receiving opioid therapy for maintenance of opioid withdrawal). In some embodiments, the subject is a subject using opioid for chronic pain management. In some embodiments, the subject is a terminally ill patient. In other embodiments the subject is a person receiving opioid withdrawal maintenance therapy.

Additional uses for formulations described herein may be to treat, reduce, inhibit, or prevent effects of opioid administration including, e.g., aberrant migration or proliferation of endothelial cells (e.g., vascular endothelial cells), increased angiogenesis, and increase in lethal factor production from opportunistic infectious agents (e.g., *Pseudomonas aeruginosa*). Additional advantageous uses of provided formulations include treatment of opioid-induced immune suppression, inhibition of angiogenesis, inhibition of vascular proliferation, treatment of pain, treatment of inflammatory conditions such as inflammatory bowel syndrome, treatment of infectious diseases and diseases of the musculokeletal system such as osteoporosis, arthritis, osteitis, periostitis, myopathies, and treatment of autoimmune diseases.

In certain embodiments, formulations of the invention may be used in methods for preventing, inhibiting, reducing, delaying, diminishing or treating gastrointestinal dysfunction, including, but not limited to, irritable bowel syndrome, opioid-induced bowel dysfunction, colitis, post-operative, paralytic ileus, or postpartum ileus, nausea and/or vomiting, decreased gastric motility and emptying, inhibition of the stomach, and small and/or large intestinal propulsion, increased amplitude of non-propulsive segmental contractions, constriction of sphincter of Oddi, increased anal sphincter tone, impaired reflex relaxation with rectal distention, diminished gastric, biliary, pancreatic or intestinal secretions, increased absorption of water from bowel contents, gastro-esophageal reflux, gastroparesis, cramping, bloating, abdominal or epigastric pain and discomfort, constipation, idiopathic constipation, post-operative gastrointestinal dysfunction following abdominal surgery (e.g., colectomy (e.g., right hemicolectomy, left hemicolectomy, transverse hemicolectomy, colectomy takedown, low anterior resection) or hernia repair), and delayed absorption of orally administered medications or nutritive substances.

Provided formulations are also useful in treatment of conditions including cancers involving angiogenesis, immune suppression, sickle cell anemia, vascular wounds, and retinopathy, treatment of inflammation associated disorders (e.g., irritable bowel syndrome), immune suppression, chronic inflammation.

In still further embodiments, veterinary applications (e.g., treatment of domestic animals, e.g. horse, dogs, cats, etc.) of use of formulations are provided. Thus, use of provided formulations in veterinary applications analogous to those discussed above for human subjects is contemplated. For example, inhibition of equine gastrointestinal motility, such as colic and constipation, may be fatal to a horse. Resulting pain suffered by the horse with colic can result in a death-inducing shock, while a long-term case of constipation may also cause a horse's death. Treatment of equines with peripheral opioid antagonists has been described, e.g., in U.S. Patent Publication No. 20050124657 published Jan. 20, 2005.

It will also be appreciated that formulations of the present invention can be employed in combination therapies, that is, methylnaltrexone and compositions thereof, can be administered concurrently with, prior to, or subsequent to, one or more other desired therapeutics or medical procedures. Particular combination therapies (therapeutics or procedures) to employ in a combination regimen will take into account compatibility of the desired therapeutics and/or procedures and the desired therapeutic effect to be achieved. It will also be appreciated that therapies employed may achieve a desired effect for the same disorder (for example, a formulation may be administered concurrently with another compound used to treat the same disorder), or they may achieve different effects (e.g., control of any adverse effects). As used herein, additional therapeutic compounds which are normally administered to treat or prevent a particular disease, or condition, are known as "appropriate for the disease, or condition, being treated".

In other embodiments, provided formulations and dosage forms are useful in preparation of medicaments, including, but not limited to medicaments useful in the treatment of side effects of opioid administration (e.g., gastrointestinal side effects (e.g., inhibition of intestinal motility, GI sphincter constriction, constipation, nausea, emesis) dysphoria, pruritis, etc.) or a combination thereof. Provided formulations are useful for preparations of medicaments, useful in treatment of patients receiving short term opioid therapy (e.g., patients suffering from post-operative gastrointestinal dysfunction receiving short term opioid administration) or subjects using opioids chronically (e.g., terminally ill patients receiving opioid therapy such as an AIDS patient, a cancer patient, a cardiovascular patient; subjects receiving chronic opioid therapy for pain management; or subjects receiving opioid therapy for maintenance of opioid withdrawal). Still further, preparation of medicaments useful in the treatment of pain, treatment of inflammatory conditions such as inflammatory bowel syndrome, treatment of infectious diseases, treatment of diseases of the musculokeletal system such as osteoporosis, arthritis, osteitis, periostitis, myopathies, treatment of autoimmune diseases and immune suppression, therapy of post-operative gastrointestinal dysfunction following abdominal surgery (e.g., colectomy (e.g., right hemicolectomy, left hemicolectomy, transverse hemicolectomy, colectomy takedown, low anterior resection), idiopathic constipation, and ileus), and treatment of disorders such as cancers involving angiogenesis, chronic inflammation and/or chronic pain, sickle cell anemia, vascular wounds, and retinopathy.

Pharmaceutical Kits and Packaging

Still further encompassed by the invention are pharmaceutical packs and/or kits. Pharmaceutical packs and/or kits provided may comprise a formulation and a container (e.g., a vial, ampoule, bottle, syringe, and/or dispenser package, or other suitable container). In some embodiments, provided kits may optionally further include a second container comprising a suitable aqueous carrier for dilution of the reconstitute for preparation of administration to a subject via IV administration. In some embodiments, contents of provided formulation container and solvent container combine to form a unit dosage form.

In some embodiments, a formulation of the invention may be useful in conjunction with patient controlled analgesia (PCA) devices, wherein a patient can administer opioid analgesia as required for pain management. In such instances, co-administration of provided formulations may be useful to prevent adverse side effects of opioid administration. Thus, kits of the invention may comprise a formulation for administration of methylnaltrexone contained within a cartridge for use in conjunction with PCA device.

In some embodiments, a formulation of the invention may be useful in conjunction with a diluent container suitable for frozen storage, wherein a formulation is diluted in suitable diluent, and provided in a container suitable for freezing. In some embodiments, such frozen containers may be thawed prior to intravenous administration of methylnaltrexone to a subject. Thus, kits of the invention may comprise a formulation for administration of methylnaltrexone in a container suitable for frozen storage, and thawing prior to administration to a subject. In some embodiment, such a container is a frozen intravenous bag.

Optionally, a single container may comprise one or more compartments for containing lyophilized formulation, and/or appropriate aqueous carrier for dilution. In some embodiments, a single container may be appropriate for modification such that the container may receive a physical modification so as to allow combination of compartments and/or components of individual compartments. For example, a foil or plastic bag may comprise two or more compartments separated by a perforated seal which may be broken so as to allow combination of contents of two individual compartments once the signal to break the seal is generated. A pharmaceutical pack or kit may thus comprise such multi-compartment containers including lyophilized formulation and appropriate solvent for reconstitution and/or appropriate aqueous carrier for dilution of reconstitute. Optionally, instructions for use are additionally provided in such kits.

In some embodiments, a pharmaceutical kit comprises a formulation in a dilution package or container wherein a needle-less exchange mechanism allows for combination of formulation and with isotonic solution for preparation for intravenous administration. For example, in certain non-limiting examples, a formulation of the invention may be utilized in conjunction with a MINIBAG® Plus diluent container system (Baxter), or an ADD VANTAGE® diluent container (Hospira) system.

Optionally, instructions for use are additionally provided in such kits of the invention. Such instructions may provide, generally, for example, instructions for dosage and administration. In other embodiments, instructions may further provide additional detail relating to specialized instructions for particular containers and/or systems for administration. Still further, instructions may provide specialized instructions for use in conjunction and/or in combination with additional therapy. In one non-limiting example, the formulations of the invention may be used in conjunction with opioid analgesia administration, which may, optionally, comprise use of a patient controlled analgesia (PCA) device. Thus, instructions for use of provided formulations may comprise instructions for use in conjunction with PCA administration devices.

In order that the invention described herein may be more fully understood, the following examples are set forth. It should be understood that these examples are for illustrative purposes only and are not to be construed as limiting this invention in any manner.

EXEMPLIFICATION

Part I: Stability of Provided Formulations

Example 1

Identification and Characterization of Degradants of Methylnaltrexone Formulations.

Previously, at least three degradation products were demonstrated from HPLC analysis in 20 mg/mL isotonic saline solution (identified as RRT peaks at about 0.72, 0.89, and 1.48 when products were analyzed by HPLC). See, e.g., US Patent Application Publication No. 20040266806A1, published Dec. 30, 2004. We examined 20 mg/mL saline methylnaltrexone solutions for production of degradants, and identification of degradants, as well as identification of inhibitors of formation of different degradant products. We have identified and characterized degradants which accumulate in certain methylnaltrexone solutions. In these degradation experiments, and in the formulations prepared in the examples, R—N-methylnaltrexone was used having less than 0.15 weight percent S—N-methylnaltrexone based on the total weight of methylnaltrexone.

For HPLC analysis, two (2) different methods were utilized to obtain the data set forth herein. These methods are summarized below:

Method A:
　Column: Prodigy ODS-3 15 cm×2.0 mm, 3 μm particles (Phenomenex)
　Flow rate: 0.25 mL/min
　Detection: UV, 280 nm
　Mobile phase: strength: Isocratic: 75:25 (v/v) 0.1% TFA in Water/Methanol
　Mobile phase: purity: Gradient as follows:
　　Solvent A: 95:5 (v/v) 0.1% TFA in Water/Methanol
　　Solvent B: 35:65 (v/v) 0.1% TFA in Water/Methanol
　Sample Solvent: 0.05M Dibasic Sodium Phosphate pH 6.8
　Gradient Program:

| Time (Min) | % Mobile Phase A |
|---|---|
| 0 | 100 |
| 45 | 50 |
| 45.1 | 100 |
| 60 | 100 |

Column Temperature: 50° C.

Method B: (Purity)
　Column: Prodigy ODS-3 15 cm×4.6 mm, 3 μm particles (Phenomenex)
　Flow rate: 1.5 mL/min
　Detection: UV, 280 nm
　Mobile phase: Gradient as follows:
　　Solvent A: 95:5 (v/v) 0.1% TFA in Water/Methanol
　　Solvent B: 25:75 (v/v) 0.1% TFA in Water/Methanol
　Sample Solvent: 0.05M Dibasic Sodium Phosphate pH 6.8
　Gradient Program:

| Time (Min) | % Mobile Phase A |
|---|---|
| 0 | 100 |
| 45 | 50 |
| 45.1 | 100 |
| 60 | 100 |

Method B: (Strength)
　Column: Prodigy ODS-3 15 cm×4.6 mm, 3 μm particles (Phenomenex)
　Flow rate: 1.0 mL/min
　Detection: UV, 280 nm
　Mobile phase: Gradient as follows:
　　Solvent A: 95:5 (v/v) 0.1% TFA in Water/Methanol
　　Solvent B: 25:75 (v/v) 0.1% TFA in Water/Methanol
　Sample Solvent: 0.05M Dibasic Sodium Phosphate pH 6.8

Gradient Program:

| Time (Min) | % Mobile Phase A |
|---|---|
| 0 | 95 |
| 1.0 | 85 |
| 12.0 | 50 |
| 15.0 | 95 |
| 20.0 | 95 |

The following compounds were identified in the stability studies using HPLC analysis (Method A) of samples under the indicated storage conditions, and, unless otherwise noted, had the following associated calculated relative retention times:

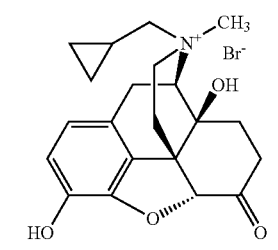

Methylnaltrezone bromide
RRT 1.00

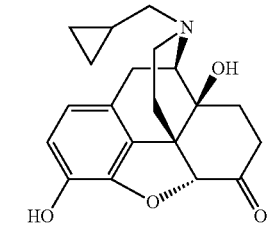

Naltrezone base
RRT 1.17

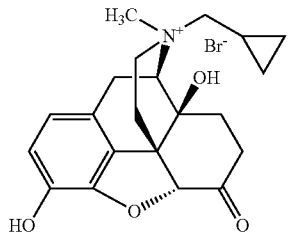

S-Methylnaltrezone
RRT 0.86 or 0.89

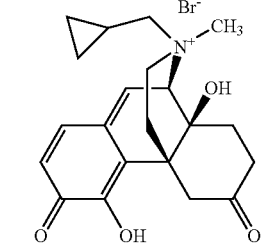

Quinone
RRT 0.89
(for Tables 11C-2, 11C-3,
12A-2, 12B-2, 12C-2, 12-D2)

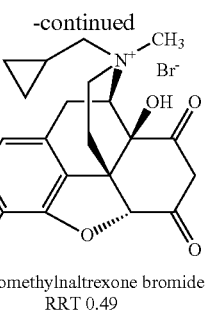

8-ketomethylnaltrexone bromide
RRT 0.49

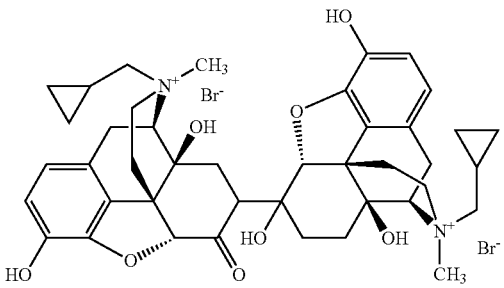

Aldol dimer
RRT 1.77

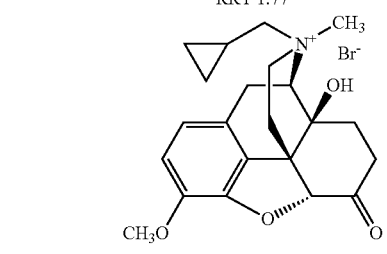

O-Methyl methalnaltrexone
RRT 1.66
(3-methoxy nalrexone methobromide)

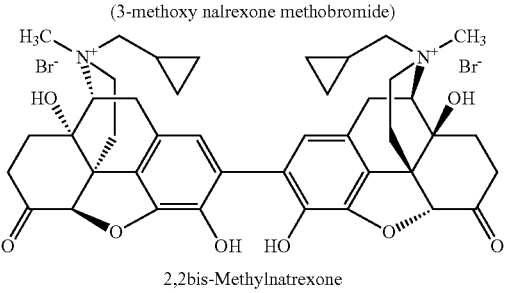

2,2bis-Methylnatrexone
RTT 1.55

Naltrexone base, S-methylnaltrexone, and O-methyl methylnaltrexone are each compounds found in initial production samples. Additional impurities/degradants formed and identified in methylnaltrexone formulations include 8-ketomethylnaltrexone bromide (RRT 0.49), the aldol dimer (RRT 1.77), O-methyl methylnaltrexone (RRT 1.66), and the 2,2 bis-methylnaltrexone (RRT 1.55), as well as additional degradants resulting at relative retention time of 0.67, 0.79 and 2.26.

Each of the three additional degradants were identified by NMR analysis following isolation from column eluates, and further characterized as described herein. The 0.67 degradant has been identified as 7-dihydroxy methylnaltrexone; the 0.79 degradant has been identified as a ring contracted form ((3R,4R,4aS,6aR,11bS)-6-carboxy-3-(cyclopropylmethyl)-4a,6,8-trihydroxy-3-methyl-1,2,3,4,4a,5,6,6a-octahydro-4,11-methano[1]benzofuro[3',2':2,3]cyclopenta[1,2-c]pyridin-3-ium); and the 2.26 degradant has been identified as a Hoffman elimination product (see the following compound names, relative retention times, and associated structure; see also, FIG. 4).

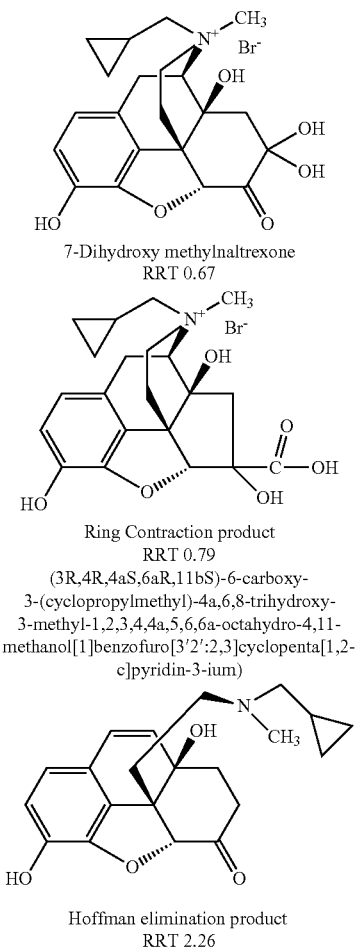

7-Dihydroxy methylnaltrexone
RRT 0.67

Ring Contraction product
RRT 0.79
(3R,4R,4aS,6aR,11bS)-6-carboxy-
3-(cyclopropylmethyl)-4a,6,8-trihydroxy-
3-methyl-1,2,3,4,4a,5,6,6a-octahydro-4,11-
methanol[1]benzofuro[3'2':2,3]cyclopenta[1,2-
c]pyridin-3-ium)

Hoffman elimination product
RRT 2.26

Figure 4:
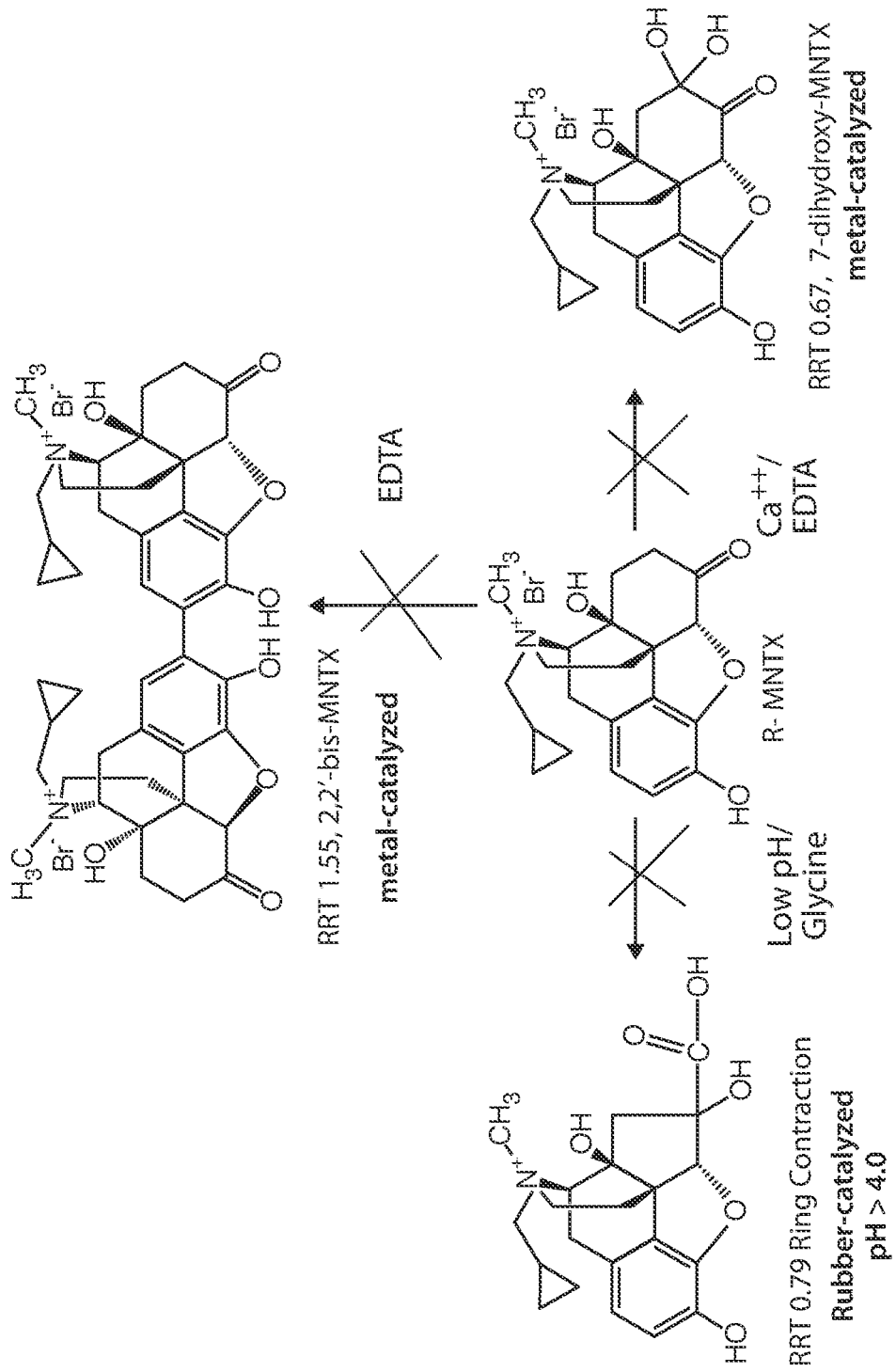
FIG. 4 depicts identified degradants of methylnaltrexone, respective relative retention times (RRT), and associated catalysis and/or inhibitors of formation which have been identified.

Results of stability studies in tables set forth in the following examples demonstrate resulting levels of each of the degradants identified in samples using HPLC analysis. Stability test procedures used in the following examples include standard pharmaceutical stability studies according to ICH guidelines, under conditions of 25° C./60% relative humidity, 40° C./65% relative humidity, and/or 70° C. FIG. 4 depicts three of the major resulting degradants, and the associate proposed mechanisms for catalysis of formation and/or methods of inhibition of formation which have been identified and further described in the examples that follow.

One of ordinary skill in the art will appreciate that minor modifications in an HPLC method or sample preparation can result in a shift of RRT. Thus, it will be appreciated that the RRT values reported herein may shift depending upon actual conditions.

Example 2

Inhibition of Metal and Calcium Mediated Degradation of Methylnaltrexone Formulations.

Figure 1B:
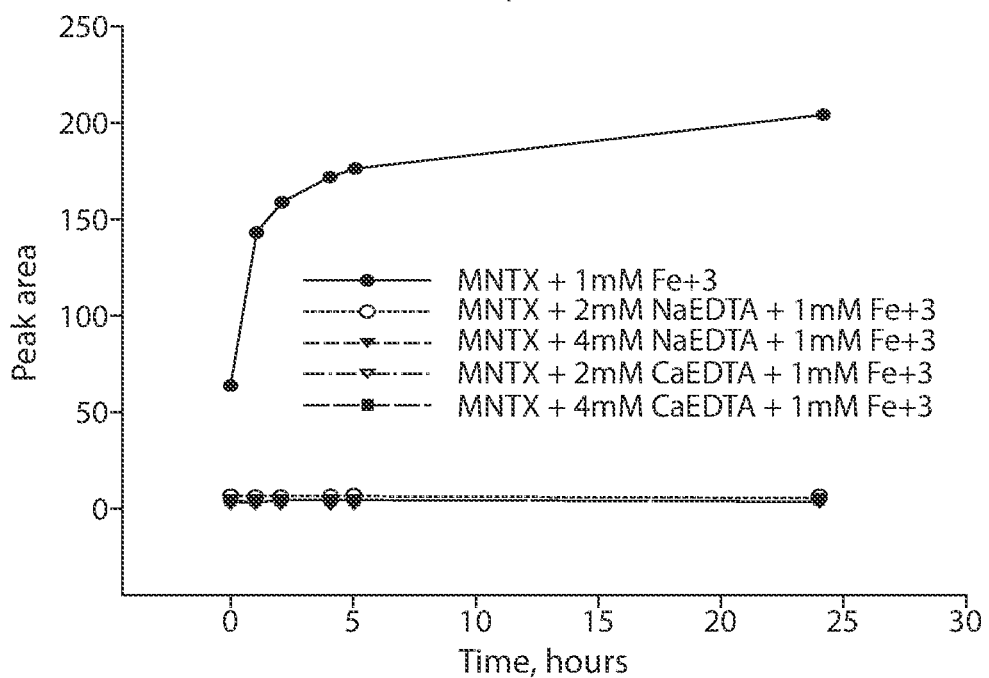

Inhibition of metal-catalyzed formation of 2,2'bis methylnaltrexone. We have found $Fe^{3+}$ facilitates degradation of methylnaltrexone bromide in solution, resulting in formation of a 2,2'bis methylnaltrexone degradant. We have found by HPLC analysis (Method B) the 2,2'bis methylnaltrexone degradant results in a peak having an RRT about 1.55. $Fe^{3+}$ is an ion that can get into the liquid formulation from several sources. For example, it can be leached from stainless steel process equipment, syringe needles, stoppers and amber vials. EDTA, as a metal chelating agent sequesters the available $Fe^{3+}$ in the solution, thereby preventing catalysis of the undesirable metal-catalyzed reactions. Methylnaltrexone solutions were prepared in 0.9% NaCl, in the presence of iron and various concentrations of sodium EDTA and calcium EDTA. Used throughout the experiments sodium EDTA is EDTA disodium dihydrate, and the terms sodium EDTA, EDTA disodium dihydrate, and NaEDTA are used interchangeably throughout. Used throughout the experiments calcium EDTA is calcium EDTA disodium, and the terms calcium EDTA, calcium EDTA disodium, and CaEDTA are used interchangeably throughout. Formation of 2,2'bis methylnaltrexone was assessed at room temperature as well as at 40° C. Addition of either sodium or calcium EDTA solution was effective at inhibiting formation of the 2,2'bis methylnaltrexone degradant. See FIG. 1A and FIG. 1B. Thus, chelating action will facilitate methylnaltrexone bromide stability in solution at room temperature.

Inhibition of metal-catalyzed formation of 7-dihydroxy-methylnaltrexone. We have found EDTA inhibits metal catalyzed formation of a 7-dihydroxy-methylnaltrexone degradant in methylnaltrexone solution. We have found by HPLC analysis (Method B) the 0.67 peak degradant to be the presence of 7-dihydroxy methylnaltrexone. Methylnaltrexone solutions were prepared in 0.9% NaCl, in the presence of iron and various concentrations of EDTA. Formation of 7-dihydroxy methylnaltrexone was assessed. Addition of either EDTA solution was effective at inhibiting formation of the 7-dihydroxy methylnaltrexone degradant. See Table 1.

TABLE 1

| | Peak area of RRT 0.67 degradant of 20 mg/ml MNTX at room temperature in presence of 1 mm Fe + 3 | | | | |
|---|---|---|---|---|---|
| Sample name | Initial | 1 hour | 2 hours | 3 hours | 4 hours |
| MNTX + 1 mmFe + 3 | 0.7 (0.017%) | 0.7 (0.019%) | 0.99 (0.024%) | 1.16 (0.028%) | 1.42 (0.035%) |
| MNTX + 0.25 mmEDTA + 1 mm Fe + 3 | 0 | 0.72 (0.018%) | 0.88 (0.019%) | 0.9 (0.022%) | 1.2 (0.029%) |
| MNTX + 0.5 mmEDTA + 1 mm Fe + 3 | 0 | 0.6 (0.015%) | 0.87 (0.02%) | 0.95 (0.023%) | 1.19 (0.029%) |
| MNTX + 0.75 mmEDTA + 1 mm Fe + 3 | 0 | 0.58 (0.014%) | 0.62 (0.013%) | 0.75 (0.018%) | 0.81 (0.02%) |
| MNTX + 1 mmEDTA + 1 mm Fe + 3 | 0 | 0.46 (0.011%) | 0.57 (0.012%) | 0.68 (0.016%) | 0.68 (0.016%) |

Figure 2A:
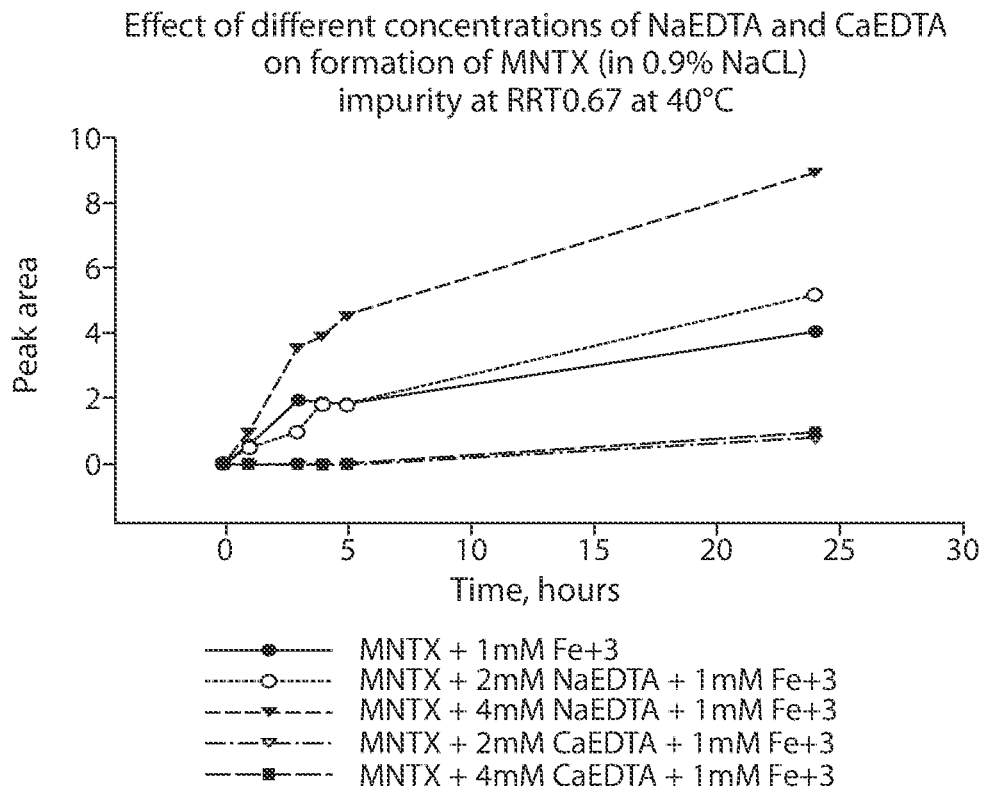
FIGS. 2A, 2B, 2C, and 2D: Effect of CaEDTA on the formation of 7-dihydroxy methylnaltrexone in solutions. The effect of CaEDTA and NaEDTA on the formation of 7-dihydroxy methylnaltrexone in the presence of iron at 40° C.
Figure 2B:
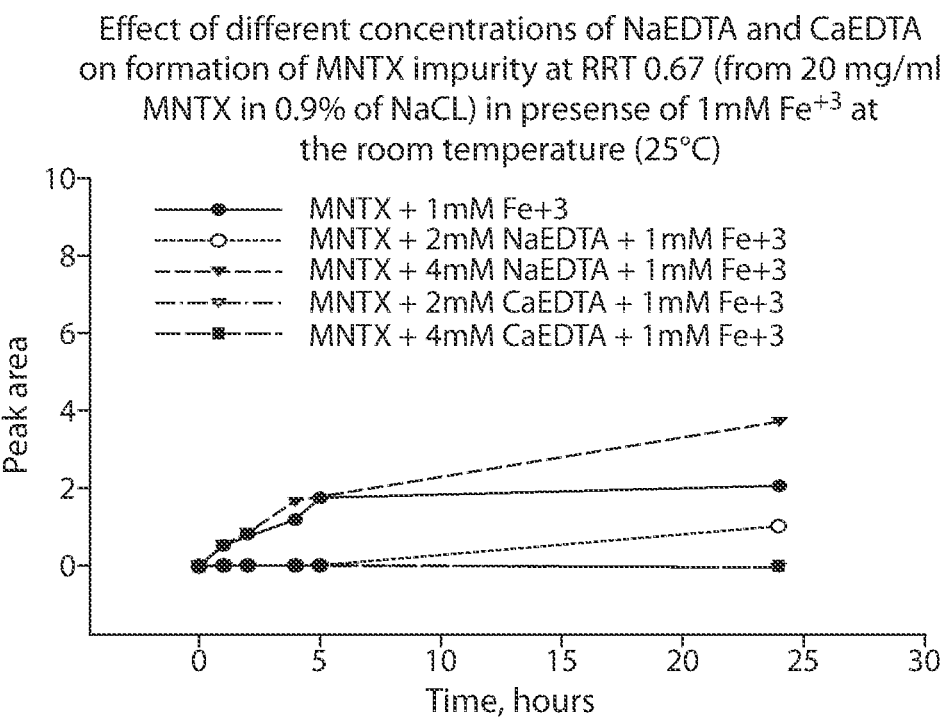
Figure 2C:
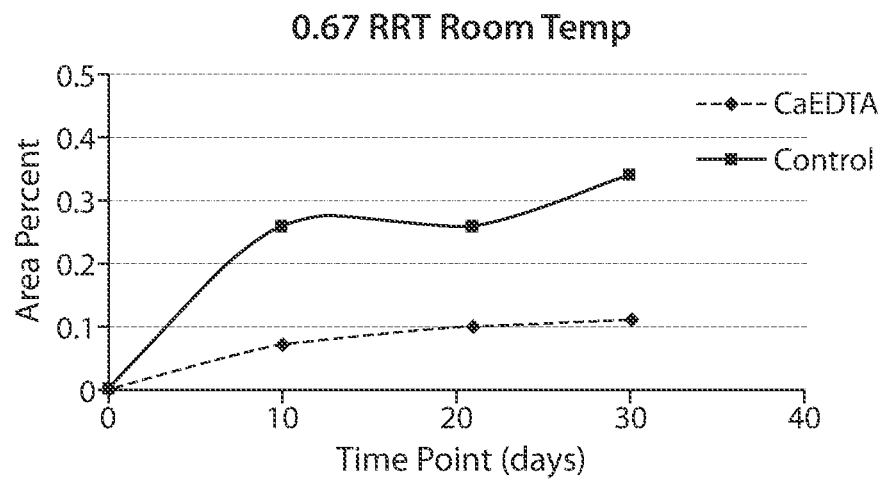
Figure 2D:
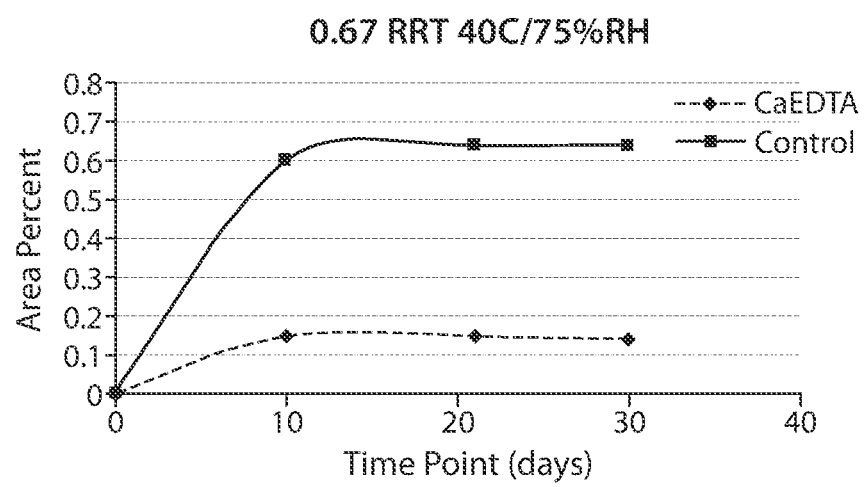

We have found $Ca^{2+}$ chelating agent provides additional inhibition of formation of a 7-dihydroxy-methylnaltrexone degradant as compared to $Na^{2+}$ chelating agent. Methylnaltrexone solutions were prepared in 0.9% NaCl, in the presence of iron and various concentrations of sodium EDTA and calcium EDTA. Formation of 7-dihydroxy-methylnaltrexone was assessed at room temperature as well as at 40° C. Addition of calcium EDTA solution was highly effective at inhibiting formation of the 7-dihydroxy-methylnaltrexone degradant at both temperatures. See FIG. 2A and FIG. 21B. Use of calcium facilitates methylnaltrexone bromide stability in solution at room temperature. Furthermore, long term storage of solution at either room temperature or 40° C./75% relative humidity also demonstrated stabilization and inhibition of 7-dihydroxy methylnaltrexone degradant formation when calcium EDTA was present. After one month at room temperature, resultant production of 7-dihydroxy-methylnaltrexone was reduced from 0.34% to 0.11% in the presence of calcium EDTA. Furthermore, at 40° C./75% RH, degradant was reduced from 0.64% in saline solution alone to 0.14% in sample containing calcium EDTA. See FIG. 2C and FIG. 2D.

Preparation of an improved room temperature methylnaltrexone formulation. Our results have shown a methylnaltrexone formulation comprising a saline solution of active compound plus calcium salt-chelating agent results in a formulation having improved room temperature stability characteristics. Preparation of such improved formulations comprise use of the following exemplary components:

| | | |
|---|---|---|
| Active | Methylnaltrexone bromide | (5 to 40 mgs) |
| Chelating agent | Calcium EDTA | (0.05 to 1.5 mgs) |
| Isotonic Delivery Vehicle | 0.9% Normal Saline | (1 to 1.25 mL) |

For a 0.6 mL fill or 1.25 mL fill, 20 or 30 mgs of methylnaltrexone bromide were dissolved in 0.9% sodium chloride; and 0.24 mg or 0.5 mg of calcium EDTA were also dissolved in the solution. Resulting solutions were prepared and filter sterilized at ambient conditions, and resulting formulations filled into clear glass vials, ampoules, syringes or auto-dispensers.

TABLE 2

Formulation

| INGREDIENTS | 0.6 mL/VIAL | 1.25 mL/VIAL |
|---|---|---|
| Methylnaltrexone bromide | 20 mg | 30 mg |
| Calcium EDTA, NF | 0.24 mg | 0.5 mg |
| Sodium Chloride | 0.65% | 0.65% |

Example 3

Inhibition of pH Dependent Degradation of Methylnaltrexone Formulations

Inhibition of pH influenced formation of methylnaltrexone degradants. We have found in the presence of $Ca^{2+}$ and EDTA, degradation of methylnaltrexone bromide in solution occurs under some stability conditions, resulting in formation of a third-methylnaltrexone degradant. We have found by HPLC analysis (Method B) the degradant results in a peak having an RRT about 0.79. Identification and production of the 0.79 degradant is described in U.S. provisional patent application 60/835,687, filed Aug. 4, 2006, filed concurrently with the present application, the contents of which are incorporated herein in their entirety by reference.

Figure 3A:
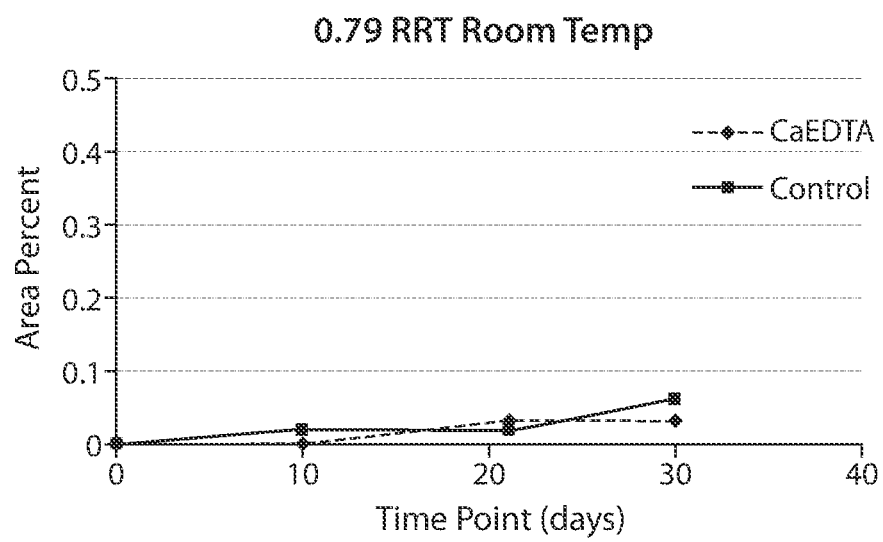
FIG. 3A and FIG. 3B: Effect of CaEDTA in methylnaltrexone solution on the formation of a methylnaltrexone degradant having an RRT 0.79 ("the 0.79 degradant"). The effect of CaEDTA and NaEDTA on the formation of the 0.79 degradant at room temperature, 25° (FIG. 3A) and at 40° C.
Figure 3B:
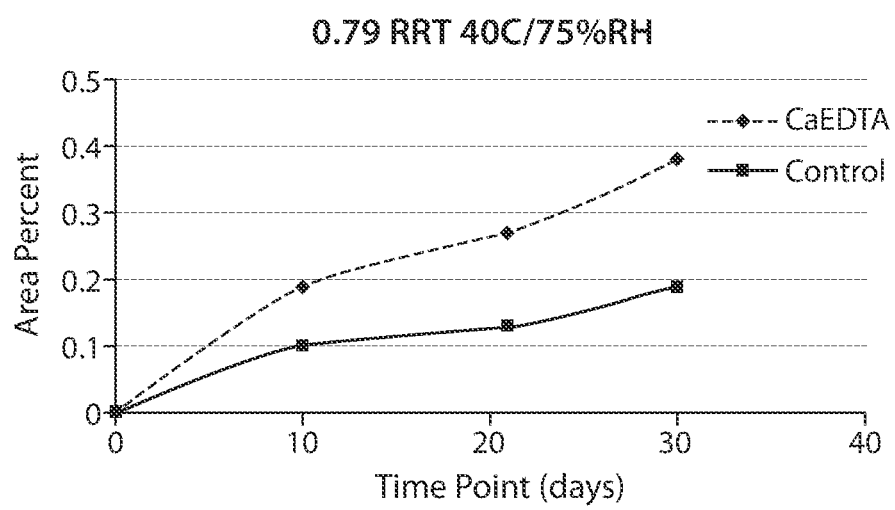

Formation of the 0.79 methylnaltrexone degradant was lower at room temperature in the CaEDTA formulation described in Example 2 above as compared to refrigerated methylnaltrexone in saline solution. Methylnaltrexone solution as described in Example 2 containing CaEDTA was compared to a control refrigerated methylnaltrexone solution in saline and formulations assessed for production of 0.79 degradant formation (room temperature CaEDTA 0.03% vs. refrigerated control saline 0.06%). See FIG. 3A and FIG. 3B. Use of calcium EDTA appears to facilitate production of the 0.79 degradant under our accelerated stability conditions, however, as it was found at 40° C./75% RH the 0.79 degradant increases from control 0.19% to 0.38% in the presence of CaEDTA. Furthermore, the peak RRT 0.79 degradant increases from 0.03% at room temperature to 0.4% at 40° C./75% RH in 1 month. Thus, while the formulation described above in Example 2 controls degradants RRT 0.67 and RRT 1.55, degradant appearing at RRT 0.79 remains under accelerated stability conditions of 40° C./75% RH.

We found reduction in pH as well as the presence of glycine resulted in stabilization of the 0.79 degradant. Table 4, summarizes the formulation stability without pH control at 70° C. The formulation has a pH of 5.6. The data confirms that a formulation containing Ca EDTA does limit the formation of 0.67 and RRT 1.55 but does not reduce RRT 0.79. After only a few days RRT 0.79 grows to over 1.0%. Each of the peaks resulting in the HPLC is represented in the table. For those products identified by the peaks: RRT 0.89 represents S-MNTX; RRT 1.17 represents naltrexone base; RRT 1.55 represent 2,2 bis methylnaltrexone; RRT 1.66 represents O-methyl-methylnaltrexone; RRT 1.77 represents aldol dimer formation; and RRT 2.26 represents Hoffman elimination degradant formation. BRL=below recordable limit.

We tested whether the 0.79 degradant is pH dependent, and the optimum pH range for a solution. Table 5 summarizes the stability of prepared solutions. Additionally, Table 6 summarizes stability of prepared solutions at 40° C./75% Relative Humidity and at 70° C., with and without pH adjustment with glycine. We found that as additional glycine HCl is added to solution, the amount of degradant at RRT 0.79 formed is greatly reduced and confirms the stability of the formulation with respect to RRT 0.79 is stabilized by the presence of glycine. See Tables 5 and 6.

TABLE 4

Stability data of MNTX 12 mg/vial, 0.28 mg/vial CaEDTA and 0.65% Sodium Chloride pH(5.6) at 70° C.

| | Initial (mg) | RRT 0.38 | RRT 0.49 | RRT 0.67 | RRT 0.79 | RRT 0.89 | RRT 1.17 | RRT 1.55 | RRT 1.66 | RRT 1.77 | RRT 1.89 | RRT 1.96 | RRT 2.01 | RRT 2.26 | Total |
|---|---|---|---|---|---|---|---|---|---|---|---|---|---|---|---|
| Specifications | NA | 0.2 | 0.5 | 0.5 | 0.5 | 0.15 | 0.15 | 0.5 | 0.15 | 0.5 | 0.2 | 0.2 | 0.2 | 0.5 | NA |
| Initial | 20 (100) | BRL | BRL | BRL | BRL | BRL | BRL | BRL | 0.12 | BRL | BRL | BRL | BRL | BRL | 0.12 |
| 70° C. | | | | | | | | | | | | | | | |
| Time and Days | | | | | | | | | | | | | | | |
| 3 | 19.9 (99.5) | BRL | BRL | 0.07 | 1.0 | BRL | BRL | BRL | 0.13 | BRL | BRL | BRL | BRL | 1.02 | 2.22 |
| 7 | 19.7 (98.5) | BRL | BRL | 0.09 | 1.5 | BRL | BRL | BRL | 0.11 | BRL | BRL | BRL | BRL | 1.58 | 3.28 |

TABLE 5

Stability of MNTX formulation 20 mg/ml, 0.4 mg/ml CaEDTA,
0.65% Sodium Chloride with pH adjusted with Glycine HCl

| | Initial (mg) | RRT 0.38 | RRT 0.49 | RRT 0.67 | RRT 0.79 | RRT 0.89 | RRT 1.17 | RRT 1.55 | RRT 1.66 | RRT 1.77 | RRT 1.89 | RRT 1.96 | RRT 2.01 | RRT 2.26 | Total |
|---|---|---|---|---|---|---|---|---|---|---|---|---|---|---|---|
| Specifications | NA | 0.2 | 0.5 | 0.5 | 0.5 | 0.15 | 0.15 | 0.5 | 0.15 | 0.5 | 0.2 | 0.2 | 0.2 | 0.5 | NA |
| pH 3 at 40° C./75% Relative Humidity | | | | | | | | | | | | | | | |
| Time and Days | | | | | | | | | | | | | | | |
| Initial | 19.8 | BRL | BRL | BRL | BRL | BRL | BRL | BRL | 0.11 | BRL | BRL | BRL | BRL | BRL | 0.11 |
| 14 | 19.9 | BRL | BRL | BRL | BRL | BRL | BRL | BRL | 0.12 | BRL | BRL | BRL | BRL | BRL | 0.12 |
| 21 | 19.9 | BRL | BRL | BRL | BRL | BRL | BRL | BRL | 0.12 | BRL | BRL | BRL | BRL | BRL | 0.12 |
| 30 | 20.1 | BRL | BRL | BRL | BRL | BRL | BRL | BRL | 0.12 | BRL | BRL | BRL | BRL | BRL | 0.12 |
| pH 3.5 at 40° C./75% Relative Humidity | | | | | | | | | | | | | | | |
| Initial | 19.9 | BRL | BRL | BRL | BRL | BRL | BRL | BRL | 0.12 | BRL | BRL | BRL | BRL | BRL | 0.12 |
| 7 | 20.1 | BRL | BRL | BRL | BRL | BRL | BRL | BRL | 0.12 | BRL | BRL | BRL | BRL | BRL | 0.12 |
| 14 | 20.0 | BRL | BRL | BRL | BRL | BRL | BRL | BRL | 0.12 | BRL | BRL | BRL | BRL | BRL | 0.12 |
| 21 | 20.3 | BRL | BRL | BRL | BRL | BRL | BRL | BRL | 0.11 | BRL | BRL | BRL | BRL | BRL | 0.11 |
| 30 | 20.1 | BRL | BRL | BRL | BRL | BRL | BRL | BRL | 0.12 | BRL | BRL | BRL | BRL | BRL | 0.12 |
| pH 4 at 40° C./75% Relative Humidity | | | | | | | | | | | | | | | |
| Initial | 20.0 | BRL | BRL | BRL | BRL | BRL | BRL | BRL | 0.12 | BRL | BRL | BRL | BRL | BRL | 0.12 |
| 14 | 20.1 | BRL | BRL | BRL | BRL | BRL | BRL | BRL | 0.11 | BRL | BRL | BRL | BRL | BRL | 0.11 |
| 21 | 20.1 | BRL | BRL | BRL | BRL | BRL | BRL | BRL | 0.14 | 0.06 | BRL | BRL | BRL | BRL | 0.20 |
| 30 | 19.9 | BRL | BRL | BRL | BRL | BRL | BRL | BRL | 0.11 | 0.06 | BRL | BRL | BRL | BRL | 0.17 |

TABLE 6

Stability of MNTX formulation 20 mg/ml, 0.4 mg/ml CaEDTA,
0.65% Sodium Chloride with pH adjusted with Glycine HCl

| | Initial (mg) | RRT 0.38 | RRT 0.49 | RRT 0.67 | RRT 0.79 | RRT 0.89 | RRT 1.17 | RRT 1.55 | RRT 1.66 | RRT 1.77 | RRT 1.89 | RRT 1.96 | RRT 2.01 | RRT 2.26 | Total |
|---|---|---|---|---|---|---|---|---|---|---|---|---|---|---|---|
| Specifications | NA | 0.2 | 0.5 | 0.5 | 0.5 | 0.15 | 0.15 | 0.5 | 0.15 | 0.5 | 0.2 | 0.2 | 0.2 | 0.5 | NA |
| pH 3 at 70° C. | | | | | | | | | | | | | | | |
| Time and Days | | | | | | | | | | | | | | | |
| Initial | 19.8 (100) | BRL | BRL | BRL | BRL | BRL | BRL | BRL | 0.11 | BRL | BRL | BRL | BRL | BRL | 0.11 |
| 10 | 19.6 (99) | BRL | BRL | 0.04 | 0.04 | BRL | BRL | BRL | 0.12 | BRL | BRL | BRL | BRL | 0.06 | 0.12 |
| 14 | | BRL | BRL | 0.07 | 0.05 | BRL | BRL | BRL | 0.11 | BRL | BRL | BRL | BRL | 0.09 | 0.32 |
| pH 3.5 at 70° C. | | | | | | | | | | | | | | | |
| Initial | 19.9 (100) | BRL | BRL | BRL | BRL | BRL | BRL | BRL | 0.12 | BRL | BRL | BRL | BRL | BRL | 0.12 |
| 5 | 20.2 (101.5) | BRL | BRL | 0.06 | BRL | BRL | BRL | BRL | 0.13 | BRL | BRL | BRL | BRL | 0.08 | 0.27 |
| 7 | 20.1 | BRL | BRL | 0.08 | 0.07 | BRL | BRL | BRL | 0.12 | BRL | BRL | BRL | BRL | 0.11 | 0.38 |
| 12 | 20.2 | BRL | BRL | 0.06 | 0.15 | BRL | BRL | BRL | 0.11 | 0.06 | BRL | BRL | BRL | 0.18 | 0.56 |
| pH 4 at 70° C. | | | | | | | | | | | | | | | |
| Initial | 20.0 (100) | BRL | BRL | BRL | BRL | BRL | BRL | BRL | 0.12 | BRL | BRL | BRL | BRL | BRL | 0.12 |
| 10 | 19.9 (99.5) | BRL | BRL | 0.05 | 0.21 | BRL | BRL | BRL | 0.13 | BRL | BRL | BRL | BRL | 0.23 | 0.39 |
| 14 | | BRL | BRL | 0.04 | 0.27 | BRL | BRL | BRL | 0.13 | BRL | BRL | BRL | BRL | 0.28 | 0.72 |

Preparation of a pH adjusted, improved room temperature formulation. Listed below, in Table 7 and Table 8, are developed formulations containing glycine HCl, including a pH adjustment step in the process, where the range of pH is 3.4-3.6 with a target pH 3.5. While not being bound by theory, this is based on the idea that while pH 3.0 is stable, the amount of irritation and sting at the site of injection would be undesirable. Furthermore, at pH 4.0, RRT 0.79 degradant begins to form. Glycine HCl is commonly used in subcutaneous formulations for pH adjustment, and has less propensity to cause site of injection stinging as results with use of citrate buffer. When glycine HCl is used to adjust the pH of formulations containing methylnaltrexone, controlling degradation is also evident. A solution containing methylnaltrexone including both CaEDTA and 0.3 mg/mL glycine HCl where the pH is adjusted to 3.4-3.6 will inhibit the formation of RRT 1.55 and greatly reduce the formation of degradants RRT 0.67 and RRT 0.79. A room temperature liquid formulation consisting of methylnaltrexone, CaEDTA, 0.65% NaCl, 0.3 mg/mL glycine HCl with a pH to 3.5 may be developed as either a subcutaneous administration or intravenous administration formulation.

Preparation of such improved formulations comprises use of the following exemplary components:

| | | |
|---|---|---|
| Active | Methylnaltrexone bromide | (5 to 40 mgs) |
| Chelating agent | Calcium EDTA | (0.05 to 1.5) |

-continued

| Isotonic Delivery Vehicle | 0.65% Normal Saline | (0.5 to 1.75 mL) |
|---|---|---|
| Stabilizer | glycine HCl | 0.3 mg/mL |
| QS to final Volume | | pH 3.4-3.6 |

TABLE 7

Formulation

| INGREDIENTS | 12 Mg/VIAL[A] | 16 Mg/VIAL[A] | |
|---|---|---|---|
| Methylnaltrexone bromide | 12 mg | 16 mg | 20 mg/mL |
| Calcium EDTA disodium dihydrate, NF | 0.24 mg | 0.0.32 mg | 0.4 mg/mL |
| Sodium Chloride | 3.9 mg | 5.20 mg | 6.5 mg/mL |
| Glycine HCL | 0.18 mg | 0.0.24 mg | 0.3 mg/mL |
| | pH 3.5 | pH 3.5 | pH 3.5 |
| Water for Injection, USP | QS to 0.6 | QS to 0.8 | |

[A]3 mL West flint glass vial with 13 mm West 4432/50 Fluorotec stopper and West 13 FO CS TE 3769 Blue Cap.

For example, for preparation of a 12 mg/Vial, 12 mgs of methylnaltrexone bromide and 3.9 mg sodium chloride were dissolved in water for injection; then 0.24 mg of calcium EDTA added and dissolved the final solution brought to a final fill volume of 0.6 mL. The pH was adjusted with Glycine HCl to between 3.4-3.6, optimally pH 3.5. Resulting solution was prepared, and filtered through 0.45 and 0.22 micron PVDF filters. Resulting solution was filled into clear glass vials under low oxygen conditions. Any suitable containers, including vials, ampoules, syringes or auto-dispensers may be utilized. Resulting preparations are stored at or below room temperature, without freezing. Resultant formulation may be used for parenteral administration, either for subcutaneous administration, or for intravenous administration applications. See Table 7.

Similarly, the levels of ingredients may be adapted to a final fill volume of 0.8 (or any other preferred final volume) to obtain the same concentrations. See Table 7.

TABLE 8

Formulation

| INGREDIENTS | 12 Mg/VIAL[A] | 16 Mg/VIAL[A] | |
|---|---|---|---|
| Methylnaltrexone bromide | 12 mg | 16 mg | 10 mg/mL |
| Calcium EDTA disodium dihydrate, NF | 0.24 mg | 0.0.32 mg | 0.2 mg/mL |
| Sodium Chloride | 3.9 mg | 5.20 mg | 3.25 mg/mL |
| Glycine HCL | 0.18 mg | 0.0.24 mg | 0.15 mg/mL |
| | pH 3.5 | pH 3.5 | pH 3.5 |
| Water for Injection, USP | QS to 1.2 | QS to 1.6 | |

[A]3 mL West flint glass vial with 13 mm West 4432/50 Fluorotec stopper and West 13 FO CS TE 3769 Blue Cap.

In an alternative exemplary formulation, for a 12 mg/Vial, 12 mgs of methylnaltrexone bromide and 3.9 mg sodium chloride were dissolved in water for injection; then 0.24 mg of calcium EDTA added and dissolved and the final solution brought to a final fill volume of 1.2 mL. The pH was adjusted with Glycine HCl to between 3.4-3.6, optimally pH 3.5. Resulting solution was prepared, and filtered through 0.45 and 0.22 micron PVDF filters. Resulting solution was filled into clear glass vials under low oxygen conditions. Any suitable containers, including vials, ampoules, syringes or auto-dispensers may be utilized. Resulting preparations are stored at or below room temperature, without freezing. Resultant formulation may be used for parenteral administration, either for subcutaneous administration, or for intravenous administration applications. See Table 8.

Similarly, the levels of ingredients may be adapted to a final fill volume of 1.6 (or any other preferred final volume) to obtain the same concentrations. See Table 8.

Example 4

Comparison and Evaluation of Buffer Compatibility

Evaluation of phosphate buffers solution stability. We have also assessed different buffers to determine compatibility and whether various conditions would convey further stability to methylnaltrexone solutions. Table 9 and Table 10 show results (HPLC Method A) of total degradant formation over time in methylnaltrexone solutions prepared in phosphate solution (Table 9), and glycine solution (Table 10). We found at pH 7, glycine provides better stability characteristics to samples than phosphate.

TABLE 9

Stability of MNTX in pH 7, 0.02M Phosphate* Solution

| Condition | Elapsed Time | Strength (mg/ml) | % Initial | Total Impurities (% Total Area) | pH of Formulation | Appearance and Description |
|---|---|---|---|---|---|---|
| Room Temperature | 0 time | 0.988 | 100 | 0.025 | 7.09 | Clear, colorless solution |
| | 1 day | 0.988 | 100 | 0.134 | 7.12 | Clear, colorless solution |
| | 2 days | 0.996 | 100.8 | 0.262 | 7.11 | Clear, colorless solution |
| | 6 days | 0.999 | 101.1 | 0.786 | 7.14 | Clear, colorless solution |
| | 9 days | 0.999 | 101.1 | 1.25 | 7.14 | Clear, colorless solution |
| | 14 days | 0.988 | 100.0 | 1.561 | 7.14 | Clear, colorless solution |
| | 21 days | 0.971 | 98.3 | 2.07 | 7.09 | Clear, colorless solution |
| 40° C. | 0 time | 1.092 | 100 | 0.06 | 7.08 | Clear, colorless solution |
| | 1 day | 1.069 | 97.9 | 0.471 | 7.15 | Clear, colorless solution |

TABLE 9-continued

Stability of MNTX in pH 7, 0.02M Phosphate* Solution

| Condition | Elapsed Time | Strength (mg/ml) | % Initial | Total Impurities (% Total Area) | pH of Formulation | Appearance and Description |
|---|---|---|---|---|---|---|
| | 2 days | 1.066 | 97.6 | 1.771 | 7.36 | Clear, colorless solution |
| | 6 days | 1.043 | 95.5 | 4.297 | 7.12 | Clear, colorless solution |
| | 9 days | 1.027 | 94.0 | 5.648 | 7.11 | Clear, colorless solution |
| | 14 days | 1.006 | 92.1 | 8.3 | 7.09 | Clear, very slightly yellow sol. |
| | 21 days | 0.973 | 89.1 | 11.613 | 7.08 | Clear, very slightly yellow sol. |
| 60° C. | 0 time | 1.092 | 100 | 0.06 | 7.08 | Clear, colorless solution |
| | 1 day | 1.028 | 94.1 | 6.109 | 7.12 | Clear, colorless solution |
| | 2 days | 0.991 | 90.8 | 10.291 | 7.17 | Clear, colorless solution |
| | 6 days | 0.877 | 80.3 | 22.512 | 7.08 | Clear, colorless solution |
| | 9 days | 0.806 | 73.8 | 28.351 | 7.06 | Clear, yellow solution |
| | 14 days | 0.726 | 66.5 | 35.59 | 7.04 | Clear, yellow solution |
| | 21 days | 0.745 | 68.2 | 42.23 | 6.94 | Clear, yellow solution |

*Phosphate Buffer: $KH_2PO_4$ and $Na_2HPO_4$

TABLE 10

Stability of MNTX in pH 7, 0.02M Glycine* Solution

| Condition | Elapsed Time | Strength (mg/ml) | % Initial | Total Impurities (% Total Area) | pH of Formulation | Appearance and Description |
|---|---|---|---|---|---|---|
| Room Temperature | 0 time | 0.993 | 100 | 0.11 | 7.06 | Slightly yellowish, clear solution |
| | 1 day | 0.993 | 100 | 0.076 | 6.91 | Clear, colorless solution |
| | 2 days | 0.994 | 100.1 | 0.14 | 7.11 | Clear, colorless solution |
| | 6 days | 0.987 | 99.4 | 0.302 | 7.37 | Slight precipitate on the bottom |
| | 9 days | 1.005 | 101.2 | 0.425 | 7.99 | Slightly hazy on the bottom |
| | 14 days | 0.998 | 100.5 | 0.32 | 7.21 | Slightly hazy on the bottom |
| | 21 days | 0.989 | 99.6 | 0.62 | 7.16 | Clear, colorless solution |
| 40° C. | 0 time | 1.051 | 100 | 0.097 | 7.15 | Clear, colorless solution |
| | 1 day | 1.04 | 99.0 | 0.403 | 7.53 | Clear, colorless solution |
| | 2 days | 1.039 | 98.9 | 0.379 | 7.69 | Clear, colorless solution |
| | 6 days | 1.043 | 99.2 | 0.468 | 7.50 | Clear, colorless solution |
| | 9 days | 1.039 | 98.9 | 0.669 | 7.16 | Clear, colorless solution |
| | 14 days | 1.036 | 98.6 | 0.74 | 7.55 | Clear, colorless solution |
| | 21 days | 1.01 | 96.1 | 0.975 | 7.26 | Clear, colorless solution |
| 60° C. | 0 time | 1.051 | 100 | 0.097 | 7.15 | Clear, colorless solution |

TABLE 10-continued

Stability of MNTX in pH 7, 0.02M Glycine* Solution

| Condition | Elapsed Time | Strength (mg/ml) | % Initial | Total Impurities (% Total Area) | pH of Formulation | Appearance and Description |
|---|---|---|---|---|---|---|
| | 1 day | 1.032 | 98.2 | 1.046 | 7.20 | Clear, colorless solution |
| | 2 days | 1.032 | 98.2 | 1.757 | 7.27 | Clear, colorless solution |
| | 6 days | 1.002 | 95.3 | 4.043 | 6.98 | Clear, colorless solution |
| | 9 days | 0.977 | 93.0 | 5.294 | 6.95 | Clear, light yellow solution |
| | 14 days | 0.959 | 91.2 | 6.51 | 6.94 | Clear, light yellow solution |
| | 21 days | 0.937 | 89.2 | 9.122 | 6.37 | Clear, light yellow solution |

*Glycine Buffer: Glycine and NaOH

Preparation of a methylnaltrexone formulation comprising sodium EDTA and citrate buffer. Methylnaltrexone formulations consisting of methylnaltrexone, sodium EDTA, and sodium chloride in citrate buffer have been described (see US Patent Application Publication US2004/0266806A1, published Dec. 30, 2004). We have prepared solutions comprising the same components for stability comparison studies with our present formulations.

Formulations containing 20 mg/mL methylnaltrexone bromide in either A-0.7 mg/mL NaEDTA/pH 3.5 adjusted with citrate buffer; and B-0.4 mg/mL CaEDTA/0.65% NaCl/pH 3.5 adjusted with glycine buffer were prepared. Each of the formulations were assessed over time for presence of degradant formation, the results are shown in Table 11.

Formulations containing 5 mg/mL methylnaltrexone bromide (12 mg/vial or 24 mg/vial) were prepared as described in Example 12, below. Each of the formulations were assessed over time for presence of degradant formation, the results are shown in Table 12.

Under aggressive stability conditions, solutions containing sodium EDTA, even high levels of sodium EDTA, the 0.67 and the 0.79 degradant begin to increase. It is believed the formulations and methods provided herein for production of methylnaltrexone solutions will provide for compositions which retain stability and will maintain acceptable degradant levels over extended time periods.

TABLE 11

Stability Comparisons of 20 mg/mL methylnaltrexone formulation

TABLE 11A. Stability data for liquid formulation containing 20 mg/ml MNTX, 0.7 mg/ml NaEDTA 0.4% Sodium Chloride and pH 3.5 adjusted with Citric buffer (HPLC Method B)

| | Initial (mg) | RRT 0.38 | RRT 0.49 | RRT 0.67 | RRT 0.79 | RRT 0.89 | RRT 1.17 | RRT 1.55 | RRT 1.66 | RRT 1.77 | RRT 1.89 | RRT 1.96 | RRT 2.01 | RRT 2.26 | Total |
|---|---|---|---|---|---|---|---|---|---|---|---|---|---|---|---|
| Specifications | NA | 0.2 | 0.5 | 0.5 | 0.5 | 0.15 | 0.15 | 0.5 | 0.15 | 0.5 | 0.2 | 0.2 | 0.2 | 0.5 | NA |
| Initial | 20.1 | BRL | BRL | BRL | BRL | BRL | BRL | BRL | BRL | BRL | BRL | BRL | BRL | BRL | 0.11 |
| Time and Days | | | | | | | | | | | | | | | | |
| *Room Temperature* | | | | | | | | | | | | | | | | |
| 7 | 20.2 | BRL | BRL | BRL | BRL | BRL | BRL | BRL | 0.15 | BRL | BRL | BRL | BRL | BRL | 0.12 |
| 14 | 20.0 | BRL | BRL | BRL | BRL | BRL | BRL | BRL | 0.11 | BRL | BRL | BRL | BRL | BRL | 0.11 |
| 30 | 20.1 | BRL | BRL | BRL | BRL | BRL | BRL | BRL | 0.12 | BRL | BRL | BRL | BRL | BRL | 0.12 |
| *40° C./75% Relative Humidity* | | | | | | | | | | | | | | | | |
| 7 | 20.1 | BRL | BRL | BRL | BRL | BRL | BRL | BRL | 0.12 | BRL | BRL | BRL | BRL | BRL | 0.12 |
| 14 | 20.2 | BRL | BRL | BRL | BRL | BRL | BRL | BRL | 0.12 | BRL | BRL | BRL | BRL | BRL | 0.12 |
| 30 | 20.0 | BRL | BRL | BRL | BRL | BRL | BRL | BRL | 0.12 | BRL | BRL | BRL | BRL | BRL | 0.12 |
| *70° C.* | | | | | | | | | | | | | | | | |
| 7 | 20.0 | BRL | 0.1 | 0.06 | BRL | BRL | BRL | 0.10 | 0.13 | BRL | BRL | BRL | BRL | 0.09 | 0.38 |
| 14 | 19.9 | BRL | 0.16 | 0.15 | BRL | 0.06 | BRL | BRL | 0.12 | 0.06 | BRL | BRL | BRL | 0.15 | 0.64 |
| 30 | 20.0 | BRL | 0.10 | 0.38 | 0.05 | BRL | BRL | BRL | 0.14 | BRL | 0.14 | BRL | BRL | 0.30 | 1.21 |

Table 11B: Stability data for liquid formulation 20 mg/ml MNTX, 0.4 mg/ml CaEDTA and 0.65% Sodium Chloride with pH 3.5 adjusted with Glycine Hydrochloride (HPLC Method B)

| | Initial (mg) | RRT 0.38 | RRT 0.49 | RRT 0.67 | RRT 0.79 | RRT 0.89 | RRT 1.17 | RRT 1.55 | RRT 1.66 | RRT 1.77 | RRT 1.89 | RRT 1.96 | RRT 2.01 | RRT 2.26 | Total |
|---|---|---|---|---|---|---|---|---|---|---|---|---|---|---|---|
| Specifications | NA | 0.2 | 0.5 | 0.5 | 0.5 | 0.15 | 0.15 | 0.5 | 0.15 | 0.5 | 0.2 | 0.2 | 0.2 | 0.5 | NA |
| Time and Days | | | | | | | | | | | | | | | | |
| *pH 3.5 at Room Temperature* | | | | | | | | | | | | | | | | |
| Initial | 20.2 | BRL | BRL | BRL | BRL | BRL | BRL | BRL | 0.12 | BRL | BRL | BRL | BRL | BRL | 0.12 |
| 7 | 20.1 | BRL | BRL | BRL | BRL | BRL | BRL | BRL | 0.12 | BRL | BRL | BRL | BRL | BRL | 0.11 |
| 14 | 20.1 | BRL | BRL | BRL | BRL | BRL | BRL | BRL | 0.12 | BRL | BRL | BRL | BRL | BRL | 0.12 |
| 30 | 19.8 | BRL | BRL | BRL | BRL | BRL | BRL | BRL | 0.11 | BRL | BRL | BRL | BRL | BRL | 0.11 |
| *pH 3.5 at 40° C./75% Relative Humidity* | | | | | | | | | | | | | | | | |
| Initial | 19.9 | BRL | BRL | BRL | BRL | BRL | BRL | BRL | 0.12 | BRL | BRL | BRL | BRL | BRL | 0.12 |
| 7 | 20.1 | BRL | BRL | BRL | BRL | BRL | BRL | BRL | 0.12 | BRL | BRL | BRL | BRL | BRL | 0.12 |
| 14 | 20.0 | BRL | BRL | BRL | BRL | BRL | BRL | BRL | 0.12 | BRL | BRL | BRL | BRL | BRL | 0.12 |

TABLE 11-continued

Stability Comparisons of 20 mg/mL methylnaltrexone formulation

| | | | | | | | | | | | |
|---|---|---|---|---|---|---|---|---|---|---|---|
| 21 | 20.3 | BRL | BRL | BRL | BRL | BRL | BRL | BRL | 0.11 | BRL | 0.11 |
| 30 | 20.1 | BRL | BRL | BRL | BRL | BRL | BRL | BRL | 0.12 | BRL | 0.12 | pH 3.5 at 70° C.

| | | | | | | | | | | | |
|---|---|---|---|---|---|---|---|---|---|---|---|
| Initial | 19.9 | BRL | BRL | BRL | BRL | BRL | BRL | BRL | | BRL | |
| 5 | 20.2 | BRL | 0.06 | BRL | BRL | BRL | BRL | BRL | 0.12 | 0.08 | 0.27 |
| 7 | 20.0 | BRL | 0.08 | BRL | 0.07 | BRL | BRL | BRL | 0.13 | 0.11 | 0.38 |
| 12 | 19.9 | BRL | 0.06 | BRL | 0.15 | BRL | 0.06 | BRL | 0.12 0.11 | 0.18 | 0.56 |

Table 11C-1: Stability Data for Methylnaltrexone Bromide, 20 mg/mL Injection, CaEDTA Formulation

| Storage Time | Description Reconstituted Solution | Strength | pH | Edetate Calcium Disodium Content |
|---|---|---|---|---|
| Specification | Clear solution, colorless to pale yellow, essentially free of visible particulates | 90.0-11.0% LC | 3.0-5.0 | 0.36-0.44 mg/mL |
| Method | HPLC Method A | L28228-147 | USP <791> | L34449-051 |
| Initial | Conforms | 98.2, 97.2, 97.6 | 3.7, 3.6 | 0.41 |
| 25° C./60% RH 1 Month | No change | 99.0 | 3.6, 3.6 | 0.41 |
| 3 Months | No change | 99.1 | 3.6, 3.6 | 0.41 |
| 6 Months | No change | 100.3 | 3.4, 3.4 | 0.41 |
| 9 Months | No change | 99.2 | 3.4, 3.4 | NT |
| 30° C./75% RH 1 Month | No change | 99.0 | 3.5, 3.5 | 0.39 |
| 3 Months | No change | 100.1 | 3.5, 3.5 | 0.40 |
| 6 Months | No change | 100.9 | 3.4, 3.4 | 0.40 |
| 9 Months | No change | 97.8 | 3.4, 3.4 | NT |
| 40° C./75% RH 1 Month | No change | 99.1 | 3.6, 3.6 | 0.40 |
| 3 Months | No change | 100.1 | 3.6, 3.5 | 0.39 |
| 6 Months Inverted | No change | 99.9 | 3.5, 3.5 | NT |
| 40° C./75% RH 1 Month | No change | 99.6 | 3.5, 3.5 | 0.40 |
| 3 Months | No change | 100.3 | 3.5, 3.5 | 0.39 |
| 6 Months Upright | No change | 100.7 | 3.5, 3.5 | 0.40 |
| Light Study Exposed | No change | 101.3 | 3.6 | 0.40 |
| Packaged | No change | 98.7 | 3.5 | 0.40 |

TABLE 11-continued

Stability Comparisons of 20 mg/mL methylnaltrexone formulation

Table 11C-2: Stability Data for Methylnaltrexone Bromide, 20 mg/mL Injection, CaEDTA Formulation A)

Degradation/Impurities (HPLC Method A)

| Storage Time | RRT 0.49 | RRT 0.89 | 7-Dihydroxy MNTX | S-MNTX | Ring Contraction | Naltrexone Base | 2,2'-bis-MNTX | O-Methyl MNTX Specification | Aldol-Dimer | Hoffman Degradation | Any Unspecified (Unidentified) Degradant | Total Degradants/Impurities |
|---|---|---|---|---|---|---|---|---|---|---|---|---|
| | NMT 0.2% w/w | NMT 0.2% w/w | NMT 0.5% w/w | NMT 0.5% w/w | NMT 0.5% w/w | FIO | NMT 0.5% w/w | FIO | NMT 0.5% w/w | NMT 0.5% w/w | NMT 0.2% w/w | NMT 0.2% w/w |
| 25° C./60% RH Initial | BRL | BRL | BRL | BRL | BRL | BRL | BRL | 0.06 | BRL | BRL | BRL | BRL |
| 1 Month | BRL | BRL | BRL | BRL | BRL | BRL | BRL | 0.07 | BRL | BRL | BRL | BRL |
| 3 months | BRL | BRL | BRL | BRL | BRL | BRL | BRL | 0.07 | BRL | BRL | BRL | BRL |
| 6 months | BRL | BRL | BRL | BRL | BRL | BRL | BRL | 0.06 | BRL | BRL | BRL | BRL |
| 9 months | BRL | BRL | BRL | BRL | BRL | BRL | BRL | 0.08 | BRL | BRL | BRL | BRL |
| 30° C./75% RH 1 Month | BRL | BRL | BRL | BRL | BRL | BRL | BRL | 0.06 | BRL | BRL | BRL | BRL |
| 3 months | BRL | BRL | BRL | BRL | BRL | BRL | BRL | 0.07 | BRL | BRL | BRL | BRL |
| 6 months | BRL | BRL | BRL | BRL | BRL | BRL | BRL | 0.06 | BRL | BRL | BRL | BRL |
| 9 months | BRL | BRL | BRL | BRL | BRL | BRL | BRL | 0.06 | BRL | BRL | BRL | BRL |
| 40° C./75% RH 1 Month | BRL | BRL | BRL | BRL | BRL | BRL | BRL | 0.07 | BRL | BRL | BRL | BRL |
| 3 months | BRL | BRL | 0.07 | BRL | BRL | BRL | BRL | 0.07 | BRL | BRL | BRL | 0.1 |
| 6 months Inverted | BRL | BRL | BRL | BRL | BRL | BRL | BRL | 0.07 | BRL | BRL | BRL | BRL |
| 40° C./75% RH 1 Month | BRL | BRL | BRL | BRL | BRL | BRL | BRL | 0.07 | BRL | BRL | BRL | BRL |
| 3 months | BRL | BRL | 0.06 | BRL | BRL | BRL | BRL | 0.07 | BRL | BRL | BRL | 0.1 |
| 6 months Upright | BRL | BRL | 0.07 | BRL | BRL | BRL | BRL | 0.06 | BRL | BRL | BRL | 0.1 |

Table 11C-3: Stability Data for Methylnaltrexone Bromide, 20 mg/mL Injection, CaEDTA Formulation, (Cont'd)

Degradation/Impurities

| | RRT 0.49 | RRT 0.89 | 7-Dihydroxy MNTX | S-MNTX | Ring Contraction | Naltrexone Base[b] | 2,2'-bis-MNTX | O-Methyl[b] MNTX Specification | Aldol-Dimer | Hoffman Degradation | Any Unspecified (Unidentified) Degradant | Total Degradants/Impurities |
|---|---|---|---|---|---|---|---|---|---|---|---|---|
| Storage Time | NMT 0.2% w/w | NMT 0.2% w/w | NMT 0.5% w/w | NMT 0.5% w/w | NMT 0.5% w/w | FIO | NMT 0.5% w/w | FIO | NMT 0.5% w/w | NMT 0.5% w/w | NMT 0.2% w/w | NMT 0.2% w/w |
| Method | | | | | HPLC Method A | | | | | | | |
| Light Study Exposed | BRL | 2.13[c] | BRL | BRL | BRL | BRL | 0.56 | 0.06 | BRL | BRL | 0.21[c] (RRT1.69), 0.36 (RRT 0.54), 0.22 (RRT 0.62), 0.06(RRT 1.21), | 4.4 |

TABLE 11-continued

Stability Comparisons of 20 mg/mL methylnaltrexone formulation

| | | | | | | | | | | |
|---|---|---|---|---|---|---|---|---|---|---|
| Packaged | BRL | BRL | BRL | BRL | BRL | BRL | BRL | 0.06 | BRL | BRL |
| | | | | | | | | | | 0.09 (RRT 1.41), 0.05 (RRT 1.56), 0.46 (RRT 1.58), 0.07 (RRT 2.01), 0.14 (RRT 2.03) BRL |

BRL = Below reporting limit (0.05%);
NT = Not tested;
NMT = Not more than;
RRT = Relative retention time;
FIO = For information only.
[a]Only one determination for pH was performed (n = 1).
[b]Process impurities found in the drug substance. Tested for information
[c]The unspecified degradant at RRT 1.69 co-elutes with the process impurity O-Methylnaltrexone Methobromide. The total degradant reported at RRT 1.69 is 0.27% of which 0.06% is the process impurity O-Methylnaltrexone Methobromide and 0.21% is the unspecified degradant/impurity.

TABLE 12

Stability Comparisons of 5 mg/mL (12 mg/vial or 24 mg/vial) methylnaltrexone formulation

Table 12A-1: Stability Data for Methylnaltrexone Bromide, 5 mg/mL (12 mg/vial) IV Solution for Injection, CaEDTA Formulation

| Storage Time | | Strength | pH | Edetate Calcium Disodium Content |
|---|---|---|---|---|
| Specification Method | | 90.0-110.0% LC HPLC Method A | 3.0-5.0 USP <791> | 0.09-0.11 g/mL L34449-051 |
| Initial | | 98.9, 98.3, 98.8 | 3.6, 3.6 | 0.094 |
| 25° C./60% RH Inverted | 1 month | 100.1 | 3.5, 3.5 | 0.095 |
| | 3 months | 100.4 | 3.7, 3.7 | 0.095 |
| | 6 months | 99.7 | 3.6, 3.6 | 0.097 |
| 30° C./75% RH Inverted | 1 month | 99.9 | 3.5, 3.5 | 0.094 |
| | 3 months | 100.8 | 3.9, 3.7 | 0.096 |
| | 6 months | 99.6 | 3.6, 3.6 | 0.099 |
| 40° C./75% RH Inverted | 1 month | 100.2 | 3.5, 3.6 | 0.094 |
| | 3 months | 100.9 | 3.7, 3.8 | 0.095 |
| | 6 months | 100.4 | 3.7, 3.6 | 0.097 |
| Light Study | Exposed | 103.1 | 3.7, 3.7 | 0.091 |
| | Packaged | 99.4 | 3.6, 3.6 | 0.095 |

Table 12A-2: Stability Data for Methylnaltrexone Bromide, 5 mg/mL (12mg/vial) IV Solution for Injection, CaEDTA Formulation, (Cont'd)

Degradation/Impurities

| Storage Time | | RRT 0.49 | RRT 0.89 | 7-Dihydroxy MNTX | S-MNTX | Ring Contraction | Naltrexone Base | 2,2'-bis-MNTX | O-Methyl MNTX | Aldol-Dimer | Hofmann Degradation | Any Unspecific (Unidentified) Degradant | Total/ Degradants/ Impurities |
|---|---|---|---|---|---|---|---|---|---|---|---|---|---|
| Specification | | NMT 0.2% w/w | NMT 0.2% w/w | NMT 0.4% w/w | NMT 0.4% w/w | NMT 0.4% w/w | FIO | NMT 0.4% w/w HPLC Method A | FIO | NMT 0.4% w/w | NMT 0.4% w/w | NMT 0.2% w/w | NMT 0.2% w/w |
| Initial | | BRL | BRL | BRL | BRL | BRL | BRL | BRL | 0.06 | BRL | BRL | BRL | BRL |
| 25° C./ 60% RH Inverted | 1 Month | BRL | BRL | BRL | BRL | BRL | BRL | BRL | 0.07 | BRL | BRL | BRL | BRL |
| | 3 months | BRL | BRL | BRL | BRL | BRL | BRL | BRL | 0.07 | BRL | BRL | BRL | BRL |
| | 6 months | BRL | BRL | BRL | BRL | BRL | BRL | BRL | 0.06 | BRL | BRL | BRL | BRL |
| 30° C./ 75% RH Inverted | 1 month | BRL | BRL | BRL | BRL | BRL | BRL | BRL | 0.06 | BRL | BRL | BRL | BRL |
| | 3 months | BRL | BRL | BRL | BRL | BRL | BRL | BRL | 0.07 | BRL | BRL | BRL | BRL |
| | 6 months | BRL | BRL | BRL | BRL | BRL | BRL | BRL | 0.06 | BRL | BRL | BRL | BRL |
| 40° C./ 75% RH Inverted | 1 Month | BRL | BRL | BRL | BRL | BRL | BRL | BRL | 0.07 | BRL | BRL | BRL | BRL |
| | 3 months | BRL | BRL | 0.06 | BRL | BRL | BRL | BRL | 0.07 | BRL | BRL | BRL | 0.06 |
| | 6 months | BRL | BRL | 0.07 | BRL | BRL | BRL | BRL | 0.06 | BRL | BRL | BRL | 0.07 |
| Light Study | Exposed | BRL | 2.97 | 0.22 | BRL | BRL | BRL | 0.28 | 0.06$^c$ | BRL | BRL | 0.28 (RRT = 0.60), 0.08 (RRT = 0.63), 0.05 (RRT = 0.71), | 5.5 |

TABLE 12-continued

Stability Comparisons of 5 mg/mL (12 mg/vial or 24 mg/vial) methylnaltrexone formulation

| | Packaged | BRL | BRL | BRL | BRL | BRL | BRL | BRL | 0.07 | BRL | BRL | 0.13 (RRT = 1.21), 0.08 (RRT = 1.42), 0.99 (RRT = 1.65), 0.31 (RRT = 1.71), 0.09 (RRT = 2.09), BRL |

Table 12B-1: Stability Data for Methylnaltrexone Bromide, 5 mg/mL (24 mg/vial) IV Solution for Injection, CaEDTA Terminally Sterilized

| Storage Time | | Strength | pH | Edtate Calcium Disodium Content |
|---|---|---|---|---|
| | Specification Method | 9.0-11.0% LC HPLC Method A | 3.0-5.0 USP <791> | 0.09 0.11 g/mL L34449-051 |
| | Initial | 99.4, 99.7, 99.7 | 3.6, 3.7 | 0.093 |
| 25° C./60% RH Inverted | 1 month | 100.2 | 3.6, 3.6 | 0.096 |
| | 3 months | 100.4 | 3.6, 3.6 | 0.094 |
| | 6 months | 99.6 | 3.7, 3.7 | 0.096 |
| 30° C./75% RH Inverted | 1 month | 98.7 | 3.6, 3.6 | 0.098 |
| | 3 months | 100.4 | 3.6, 3.7 | 0.093 |
| | 6 months | 100.6 | 3.7, 3.7 | 0.096 |
| 40° C./75% RH Inverted | 1 month | 99.5 | 3.6, 3.6 | 0.096 |
| | 3 months | 100.6 | 3.7, 3.7 | 0.094 |
| | 6 months | 100.2 | 3.7, 3.7 | 0.094 |
| Light Study | Exposed | 99.6 | 3.7, 3.7 | 0.095 |
| | Packaged | 99.6 | 3.7, 3.7 | 0.090 |

Table 12B-2: Stability Data for Methylnaltrexone Bromide, 5 mg/mL (24 mg/vial) IV Solution for Injection, CaEDTA Terminally Sterilized (Cont'd)

| | | Degradation/Impurities | | | | | | | | | |
|---|---|---|---|---|---|---|---|---|---|---|---|
| Storage Time | | RRT 0.49 | RRT 0.89 | 7-Dihydroxy MNTX | S-MNTX | Ring Contraction | Naltrexone Base | 2,2'-bis-MNTX | O-Methyl MNTX | Aldol-Dimer | Hofmann degradation | Any Unspecified (Unidentified) Degradent | Total Degradants/Impurities |
| | Specification | NMT 0.2% w/w | NMT 0.2% w/w | NMT 0.4% w/w | NMT 0.4% w/w | NMT 0.4% w/w | FIO | NMT 0.4% w/w HPLC Method A | FIO | NMT 0.4% w/w | NMT 0.4% w/w | NMT 0.2% w/w | NMT 0.2% w/w |
| Initial | | BRL | BRL | BRL | BRL | BRL | BRL | BRL | 0.07 | BRL | BRL | BRL | BRL |
| 25° C./60% RH Inverted | 1 Month | BRL | BRL | BRL | BRL | BRL | BRL | BRL | 0.06 | BRL | BRL | BRL | BRL |
| | 3 Months | BRL | BRL | BRL | BRL | BRL | BRL | BRL | 0.07 | BRL | BRL | BRL | BRL |
| | 6 Months | BRL | BRL | BRL | BRL | BRL | BRL | BRL | 0.07 | BRL | BRL | BRL | BRL |
| 30° C./75% RH Inverted | 1 Month | BRL | BRL | BRL | BRL | BRL | BRL | BRL | 0.07 | BRL | BRL | BRL | BRL |
| | 3 Months | BRL | BRL | BRL | BRL | BRL | BRL | BRL | 0.06 | BRL | BRL | BRL | BRL |
| | 6 Months | BRL | BRL | BRL | BRL | BRL | BRL | BRL | 0.06 | BRL | BRL | BRL | BRL |
| 40° C./75% RH Inverted | 1 Month | BRL | BRL | 0.06 | BRL | BRL | BRL | BRL | 0.07 | BRL | BRL | BRL | BRL |
| | 3 Months | BRL | BRL | BRL | BRL | BRL | BRL | BRL | 0.08 | BRL | BRL | BRL | 0.06 |
| Light | 6 Months Exposed | BRL | 3.00[a] | 0.23[a] | BRL | BRL | BRL | 0.29[a] w/w | 0.06[c] | BRL | BRL | 0.30 (RRT = 0.60), | BRL |

TABLE 12-continued

Stability Comparisons of 5 mg/mL (12 mg/vial or 24 mg/vial) methylnaltrexone formulation

| Study | | | | | | | | | | |
|---|---|---|---|---|---|---|---|---|---|---|
| Packaged | BRL | BRL | BRL | BRL | BRL | BRL | 0.07 | BRL | BRL | 0.08 (RRT = 0.63), 0.05 (RRT = 0.71), 0.14 (RRT = 1.21), 0.09 (RRT = 1.42), 0.97 (RRT = 1.65), 0.35 (RRT = 1.71), 0.09 (RRT = 2.09) BRL |

Table 12C-1: Stability Data for Methylnaltrexone Bromide, 5 mg/mL (24 mg/vial) IV Solution for Injection, CaEDTA Formulation

| Storage Time | Strength | pH | Edetate Calcium Disodium Content |
|---|---|---|---|
| Specification Method | 90.0-110.0% LC HPLC Method A | 3.0-5.0 USP <791> | 0.09 0.11 g/mL L34449-051 |
| Initial | 99.8, 99.3, 99.2 | 3.6, 3.6 | 0.09 |
| 25° C./60% RH 1 month | 100.5 | 3.5, 3.5 | 0.094 |
| Inverted 3 months | 100.8 | 3.7, 3.7 | 0.095 |
| 6 months | 99.8 | 3.5, 3.5 | 0.098 |
| 30° C./75% RH 1 month | 100.5 | 3.5, 3.5 | 0.094 |
| Inverted 3 months | 100.7 | 3.7, 3.7 | 0.095 |
| 6 months | 99.9 | 3.6, 3.6 | 0.094 |
| 40° C./75% RH 1 month | 100.3 | 3.5, 3.5 | 0.095 |
| Inverted 3 months | 100.2 | 3.8, 3.8 | 0.095 |
| 6 months | 100.3 | 3.7, 3.6 | 0.098 |
| Light Study Exposed | 102.6 | 3.5, 3.6 | 0.092 |
| Packaged | 99.8 | 3.6, 3.6 | 0.095 |

Table 12C-2: Stability Data for Methylnaltrexone Bromide, 5 mg/mL (24 mg/vial) IV Solution for Injection, CaEDTA Formulation (Cont'd)

Degradation/Impurities

| Storage Time | RRT 0.49 | RRT 0.89 | 7-Dihydroxy MNTX | S-MNTX | Ring Contraction | Naltrexone Base | 2,2'-bis-MNTX | O-Methyl MNTX | Aldol-Dimer | Hofmann degradation | Any Unspecified (Unidentified) Degradent | Total Degradants/Impurities |
|---|---|---|---|---|---|---|---|---|---|---|---|---|
| Specification | NMT 0.2% w/w | NMT 0.2% w/w | NMT 0.4% w/w | NMT 0.4% w/w | NMT 0.4% w/w | FIO HPLC Method A | NMT 0.4% w/w | FIO | NMT 0.4% w/w | NMT 0.4% w/w | NMT 0.2% w/w | NMT 0.2% w/w |
| Initial | BRL | BRL | BRL | BRL | BRL | BRL | BRL | 0.07 | BRL | BRL | BRL | BRL |
| 25° C./60% RH 1 Month | BRL | BRL | BRL | BRL | BRL | BRL | BRL | 0.06 | BRL | BRL | BRL | BRL |
| Inverted 3 months | BRL | BRL | BRL | BRL | BRL | BRL | BRL | 0.06 | BRL | BRL | BRL | BRL |
| 6 months | BRL | BRL | BRL | BRL | BRL | BRL | BRL | 0.07 | BRL | BRL | BRL | BRL |
| 30° C./75% RH 1 Month | BRL | BRL | BRL | BRL | BRL | BRL | BRL | 0.06 | BRL | BRL | BRL | BRL |
| Inverted 3 months | BRL | BRL | BRL | BRL | BRL | BRL | BRL | 0.07 | BRL | BRL | BRL | BRL |
| 6 months | BRL | BRL | BRL | BRL | BRL | BRL | BRL | 0.06 | BRL | BRL | BRL | BRL |
| 40° C./75% RH 1 Month | BRL | BRL | BRL | BRL | BRL | BRL | BRL | 0.07 | BRL | BRL | BRL | BRL |
| Inverted 3 months | BRL | BRL | 0.06 | BRL | BRL | BRL | BRL | 0.06 | BRL | BRL | BRL | 0.06 |

TABLE 12-continued

Stability Comparisons of 5 mg/mL (12 mg/vial or 24 mg/vial) methylnaltrexone formulation

| Light Study | | | | | | | | | |
|---|---|---|---|---|---|---|---|---|---|
| Exposed | BRL | 2.23[a] | 0.19[a] | BRL | BRL | BRL | 0.21 | 0.07 | BRL | 0.18 (RRT = 0.60), 0.10 (RRT = 1.21), 0.06 (RRT = 1.42), 1.00 (RRT = 1.65), 0.25 (RRT = 1.71), 0.07 (RRT = 2.09), BRL |
| Packaged | BRL | BRL | BRL | BRL | BRL | BRL | BRL | 0.06 | BRL | BRL |

Table 12D-1: Stability Data for Methylnaltrexone Bromide, 5 mg/mL (24 mg/vial) IV Solution for Injection, CaEDTA Formulation (Terminally Sterilized) (HPLC Method A)

| Storage Time | Strength | pH | Edetate Calcium Disodium Content |
|---|---|---|---|
| Specification | 90.0-110.0% LC | 3.0-5.0 | 0.09 0.11 g/mL |
| Method | L28228-147 | USP <791> | L34449-051 |
| Initial | 99.7, 99.8, 98.2 | 3.5, 3.5 | 0.095 |
| 25° C./60% RH 1 month | 99.7 | 3.5, 3.5 | 0.093 |
| Inverted 3 months | 101.5 | 3.6, 3.6 | 0.091 |
| 30° C./75% RH 6 months | 100.8 | 3.6, 3.5 | 0.095 |
| Inverted 1 month | 99.9 | 3.5, 3.5 | 0.099 |
| 3 months | 99.8 | 3.6, 3.6 | 0.094 |
| 40° C. 6 months | 101.1 | 3.6, 3.6 | 0.094 |
| 75% RH 1 month | 99.5 | 3.6, 3.6 | 0.095 |
| Inverted 3 months | 100.3 | 3.6, 3.6 | 0.095 |
| 6 months | 100.2 | 3.7, 3.8 | 0.095 |
| Light Study Exposed | 103.1 | 3.7, 3.6 | 0.093 |
| Packaged | 100.1 | 3.6, 3.6 | 0.092 |

Table 12D-2: Stability Data for Methylnaltrexone Bromide, 5 mg/mL (24 mg/vial) IV Solution for Injection, CaEDTA Formulation (Terminally Sterilized), (Cont'd)

Degradation/Impurities

| Storage Time | RRT 0.49 | RRT 0.89 | 7-Dihydroxy MNTX | S-MNTX | Ring Contraction | Naltrexone Base | 2,2'-bis-MNTX | O-Methyl MNTX | Aldol-Dimer | Hofmann degradation | Any Unspecified (Unidentified) Degradent | Total Degradants/Impurities |
|---|---|---|---|---|---|---|---|---|---|---|---|---|
| Specification Method | NMT 0.2% w/w | NMT 0.2% w/w | NMT 0.4% w/w | NMT 0.4% w/w | NMT 0.4% w/w | FIO | NMT 0.4% w/w | FIO | NMT 0.4% w/w | NMT 0.4% w/w | NMT 0.2% w/w | NMT 0.2% w/w |
| Initial | BRL | BRL | BRL | BRL | BRL | BRL | BRL | 0.06 | BRL | BRL | BRL | BRL |

HPLC Method A

| | | | | | | | | | | | | |
|---|---|---|---|---|---|---|---|---|---|---|---|---|
| 25° C./60% RH 1 Month | BRL | BRL | BRL | BRL | BRL | BRL | BRL | 0.06 | BRL | BRL | BRL | BRL |
| Inverted 3 months | BRL | BRL | BRL | BRL | BRL | BRL | BRL | 0.07 | BRL | BRL | BRL | BRL |
| 6 months | BRL | BRL | BRL | BRL | BRL | BRL | BRL | 0.06 | BRL | BRL | BRL | BRL |
| 30° C./75% RH 1 Month | BRL | BRL | BRL | BRL | BRL | BRL | BRL | 0.06 | BRL | BRL | BRL | BRL |
| Inverted 3 months | BRL | BRL | BRL | BRL | BRL | BRL | BRL | 0.07 | BRL | BRL | BRL | BRL |
| 6 months | BRL | BRL | BRL | BRL | BRL | BRL | BRL | 0.07 | BRL | BRL | BRL | BRL |
| 40° C. 1 Month | BRL | BRL | BRL | BRL | BRL | BRL | BRL | 0.06 | BRL | BRL | BRL | BRL |

TABLE 12-continued

Stability Comparisons of 5 mg/mL (12 mg/vial or 24 mg/vial) methylnaltrexone formulation

| | | | | | | | | | |
|---|---|---|---|---|---|---|---|---|---|
| 75% RH Inverted Light | 3 months 6 months Exposed | BRL BRL BRL | BRL BRL 2.33[a] | BRL 0.09 0.20[a] | BRL BRL BRL | BRL BRL BRL | BRL BRL 0.24[a] | 0.07 0.07 0.06 | BRL BRL BRL | BRL BRL 0.20 (RRT = 0.60), 0.05 (RRT = 0.63), 0.11 (RRT = 1.21), 0.07 (RRT = 1.42), 1.08 (RRT = 1.65), 0.29 (RRT = 1.71), 0.07 (RRT = 2.09) | BRL 0.09 4.6 |
| Study | Packaged | BRL | BRL | BRL | BRL | BRL | BRL | 0.07 | BRL | BRL | BRL |

BRL = Below reporting limit (0.05%)
RRT = Relative retention time
NT = Not tested
FIO = For information only.
NMT = Not more than Example 5

The stability of a formulation containing 5.0 mg/mL IV (12 mg/vial or 24 mg/vial) was tested to determine the effect of light exposure. The formulations were assessed over time for presence of degradant formation (HPLC Method A). The results of the light stability test is shown in Tables 13A and 13B.

TABLE 13A

Effect Of Room Light Exposure on The Stability of 5.0 mg/mL IV (12 mg/Vial): vials filled at ambient condition

| Condition | Strength (mg/ml) | RRT 0.63 | RRT 0.67 7-dihydroxy MNTX mz 388 | RRT 0.79 Contracted Ring | RRT 0.89 | RRT 0.91 SMNTX | RRT 1.45 (2,2 BisMNTX) | RRT 1.66 (O-Methyl) | RRT 1.72 Aldol Dimer | Total |
|---|---|---|---|---|---|---|---|---|---|---|
| 5 mg/mL (12 mg/vial) L34325-122 AS (Aseptically Filled Clear Vials) | | | | | | | | | | |
| Initial | 4.99 | BDL | BDL | BDL | BDL | BDL | 0.01 | 0.06 | 0.04 | 0.05 |
| 5 Days | 4.95 | BDL | BDL | BDL | BDL | BDL | BDL | 0.05 | 0.03 | 0.03 |
| 10 Days | 4.98 | BDL | 0.04 | BDL | BDL | BDL | BDL | 0.05 | 0.04 | 0.08 |
| 16 Days | 4.97 | BDL | 0.03 | BDL | BDL | BDL | 0.02 | 0.05 | 0.03 | 0.08 |
| 5 mg/mL (12 mg/vial) L34325-122 TS (Terminally Sterilized for 15 minutes Clear vials) | | | | | | | | | | |
| Initial | 5.00 | BDL | 0.02 | BDL | BDL | BDL | 0.02 | 0.06 | 0.02 | 0.06 |
| 5 Days | 4.98 | BDL | 0.05 | BDL | BDL | BDL | 0.046 | 0.05 | BDL | 0.10 |
| 10 Days | 4.95 | BDL | 0.07 | BDL | BDL | BDL | 0.09 | 0.05 | BDL | 0.16 |
| 16 Days | 4.99 | 0.01 | 0.10 | BDL | BDL | 0.01 | 0.10 | 0.06 | 0.02 | 0.24 |
| 5 mg/mL (12 mg/vial) L34325-122 AS-AMB (Aseptically Filled Amber Vials) | | | | | | | | | | |
| Initial | 5.21 | BDL | 0.03 | BDL | BDL | BDL | BDL | 0.06 | 0.04 | 0.07 |
| 5 Days | 4.95 | BDL | BDL | BDL | BDL | BDL | BDL | 0.05 | 0.03 | 0.03 |
| 10 Days | 4.96 | BDL | BDL | BDL | BDL | BDL | BDL | 0.05 | 0.03 | 0.03 |
| 16 Days | 5.01 | BDL | BDL | BDL | BDL | BDL | BDL | 0.06 | 0.03 | 0.03 |
| 5 mg/mL (12 mg/vial) L34325-122 TS_AMB (Terminally Sterilized for 15 minutes Amber vials) | | | | | | | | | | |
| Initial | 5.02 | BDL | 0.03 | 0.02 | BDL | BDL | 0.01 | 0.06 | 0.02 | 0.08 |
| 5 Days | 4.97 | BDL | 0.03 | BDL | BDL | BDL | BDL | 0.06 | BDL | 0.03 |
| 10 Days | 5.01 | BDL | 0.06 | BDL | BDL | BDL | BDL | 0.05 | 0.02 | 0.08 |
| 16 Days | 4.99 | BDL | 0.04 | 0.01 | BDL | BDL | 0.01 | 0.06 | 0.02 | 0.08 |

Note:
RRT 1.66 (O-Methyl) is not added into the Total
BDL: Below detection limit of 0.01%
BRL: Below Reporting limit of 0.05%

TABLE 13B

Effect of Room Light Exposure on The Stability of 5.0 mg/mL IV (24 mg/Vial): vials filled at Ambient condition

| Condition | Strength (mg/ml) | RRT 0.63 | RRT 0.67 7-dihydroxy MNTX mz 388 | RRT 0.79 Contracted Ring | RRT 0.89 | RRT 0.91 SMNTX | RRT 1.45 (2,2 BisMNTX) | RRT 1.66 (O-Methyl) | RRT 1.72 Aldol Dimer | Total |
|---|---|---|---|---|---|---|---|---|---|---|
| 5 mg/mL (24 mg/vial) L34325-122 AS (Aseptically Filled Clear Vials) | | | | | | | | | | |
| Initial | 5.04 | BDL | 0.01 | BDL | ND | BDL | ND | 0.05 | 0.03 | 0.04 |
| 5 Days | 5.07 | BDL | 0.02 | BDL | BDL | BDL | ND | 0.05 | 0.04 | 0.06 |
| 10 Days | 5.00 | BDL | 0.02 | BDL | 0.01 | BDL | 0.02 | 0.05 | 0.03 | 0.08 |
| 16 Days | 5.03 | BDL | 0.03 | BDL | ND | BDL | 0.03 | 0.06 | 0.04 | 0.1 |
| 5 mg/mL (24 mg/vial) L34325-122 TS (Terminally Sterilized for 15 minutes Clear vials) | | | | | | | | | | |
| Initial | 5.01 | BDL | 0.03 | BDL | BDL | BDL | ND | 0.06 | 0.02 | 0.05 |
| 5 Days | 5.01 | BDL | 0.02 | BDL | BDL | BDL | 0.03 | 0.06 | 0.02 | 0.07 |
| 10 Days | 5.01 | BDL | 0.06 | BDL | BDL | BDL | 0.049 | 0.06 | 0.02 | 0.13 |
| 16 Days | 5.01 | BDL | 0.07 | BDL | BDL | 0.01 | 0.08 | 0.06 | 0.02 | 0.18 |
| 5 mg/mL (24 mg/vial) L34325-122 AS-AMB (Aseptically Filled Amber Vials) | | | | | | | | | | |
| Initial | 4.99 | BDL | 0.02 | BDL | BDL | BDL | BDL | 0.05 | 0.04 | 0.06 |
| 5 Days | 5.01 | BDL | BDL | BDL | BDL | BDL | BDL | 0.05 | 0.03 | 0.03 |
| 10 Days | 5.01 | BDL | 0.02 | BDL | BDL | BDL | BDL | 0.06 | 0.03 | 0.05 |
| 16 Days | 5.02 | BDL | BDL | BDL | BDL | BDL | BDL | 0.06 | 0.03 | 0.03 |
| 5 mg/mL (24 mg/vial) L34325-122 TS_AMB (Terminally Sterilized for 15 minutes Amber vials) | | | | | | | | | | |
| Initial | 4.98 | BDL | 0.04 | BDL | BDL | BDL | BDL | 0.06 | 0.02 | 0.06 |
| 5 Days | 5.02 | BDL | 0.04 | BDL | BDL | BDL | BDL | 0.06 | 0.02 | 0.06 |
| 10 Days | 5.01 | BDL | 0.04 | BDL | BDL | BDL | BDL | 0.05 | 0.02 | 0.06 |
| 16 Days | 5.04 | BDL | 0.03 | BDL | BDL | BDL | BDL | 0.05 | 0.02 | 0.05 |

Note:
RRT 1.66 (O-Methyl) is not added into the Total
BDL: Below detection limit of 0.01%
BRL: Below Reporting limit of 0.05%

Example 6

Evaluation of Stopper Compatibility

We assessed various available stoppers used in vial closures for their compatibility with methylnaltrexone solutions, and determined whether any had effects on formation of degradants in solution.

Identical preparations prepared as described in Example 4 were stored in parallel in vials having either a 13 mm WPS S2-F451 4432/50 Gray B2-40 Westar RS stopper (West Pharmaceutical Services) or a 13 mm S2-F451 RS D 777-1 RB2 40 stopper (Daikyo Seiko, Ltd) under various conditions. Each of the stoppers has a FluoroTec® fluorocarbon film; the Westar 4432/50 stopper is chlorobutyl rubber, while the RB2-40 RS D 777-1 stopper is bromobutyl rubber. The presence of accumulation of degradant was assessed for each of the configurations (HPLC Method A). Table 14 depicts the results of these studies. Under accelerated storage conditions, the stopper containing bromobutyl rubber appears to accumulate aldol dimer formation at a higher rate than the comparable chlorobutyl stopper.

Two batches of the formulation were prepared and subjected to stability determination. The first batch was the above methylnaltrexone IV formulation: 5 mg/ml methylnaltrexone, 0.8 mg of NaCL, 0.1 mg CaEDTA, 0.1 mg Glycine Hydrochloride infused in the 0.9% Normal Saline IV bag. The second batch was just 5 mg/ml methylnaltrexone infused in 0.9% Normal Saline IV bag. The bags were frozen and kept at −20° C. The stability data showed that over a period of 2 months both batches were stable with no degradants formed. An additional benefit to the frozen bag storage is that no protection from light is required.

Two months stability study (HPLC Method A) showed no degradation was formed thereby demonstrating that the formulation is stable under frozen conditions, that the period of use and shelf life can be longer than 6 months, and that there is no need for the hospital staff to infuse the IV bags with the drug. The bags come user ready only need to be thawed. Table 15 summarizes the results of these studies.

TABLE 14

Stopper compatibility evaluation of Methylnaltrexone with 13 mm WPS S2-F451 4432/50 Gray B2-40 Westar RS stopper (West Pharmaceutical Services) and 13 mm S2-F451 RS-D 777-1 B2 40 from Daikyo Seiko Ltd. at Room Temperature and 40° C.

| | Initial (mg) | RRT 0.38 | RRT 0.49 | RRT 0.67 | RRT 0.79 | RRT 0.89 | RRT 1.17 | RRT 1.55 | RRT 1.66 | RRT 1.77 | RRT 1.89 | RRT 1.96 | RRT 2.01 | RRT 2.26 | Total |
|---|---|---|---|---|---|---|---|---|---|---|---|---|---|---|---|
| Specifications | NA | 0.2 | 0.5 | 0.5 | 0.5 | 0.15 | 0.15 | 0.5 | 0.15 | 0.5 | 0.2 | 0.2 | 0.2 | 0.5 | NA |
| Initial | 20.2 | BRL | BRL | BRL | BRL | BRL | BRL | BRL | 0.12 | BRL | BRL | BRL | BRL | BRL | 0.12 |
| *Control at Room Temperature* | | | | | | | | | | | | | | | |
| 1 hours | 20.1 | BRL | BRL | BRL | BRL | BRL | BRL | BRL | 0.12 | BRL | BRL | BRL | BRL | BRL | 0.12 |
| 4 hours | 20.0 | BRL | BRL | BRL | BRL | BRL | BRL | BRL | 0.12 | BRL | BRL | BRL | BRL | BRL | 0.12 |
| *13 mm WPS S2-F451 4432/50 Gray B2-40 Westar RS stopper (West Pharmaceutical Services) at Room Temperature* | | | | | | | | | | | | | | | |
| 1 hours | 20.3 | BRL | BRL | BRL | BRL | BRL | BRL | BRL | 0.06 | BRL | BRL | BRL | BRL | BRL | 0.06 |
| 4 hours | 20.1 | BRL | BRL | BRL | BRL | BRL | BRL | BRL | 0.06 | BRL | BRL | BRL | BRL | BRL | 0.06 |
| *13 mm S2-F451 RS-D 777-1 B2 40 from Daikyo Seiko Ltd. at Room Temperature* | | | | | | | | | | | | | | | |
| 1 hours | 20.3 | BRL | BRL | BRL | BRL | BRL | BRL | BRL | 0.12 | BRL | BRL | BRL | BRL | BRL | 0.12 |
| 4 hours | 20.2 | BRL | BRL | BRL | BRL | BRL | BRL | BRL | 0.12 | BRL | BRL | BRL | BRL | BRL | 0.12 |
| *Control at 40° C.* | | | | | | | | | | | | | | | |
| 1 hours | 20.3 | BRL | BRL | BRL | BRL | BRL | BRL | BRL | 0.12 | BRL | BRL | BRL | BRL | BRL | 0.12 |
| 4 hours | 20.3 | BRL | BRL | BRL | BRL | BRL | BRL | BRL | 0.12 | BRL | BRL | BRL | BRL | BRL | 0.12 |
| *13 mm WPS S2-F451 4432/50 Gray B2-40 Westar RS stopper (West Pharmaceutical Services) at 40° C.* | | | | | | | | | | | | | | | |
| 1 hours | 20.1 | BRL | BRL | BRL | BRL | BRL | BRL | BRL | 0.06 | BRL | BRL | BRL | BRL | BRL | 0.06 |
| 4 hours | 20.2 | BRL | BRL | BRL | BRL | BRL | BRL | BRL | 0.06 | 0.05 | BRL | BRL | BRL | BRL | 0.06 |
| *13 mm S2-F451 RS-D 777-1 B2 40 from Daikyo Seiko Ltd. at 40° C.* | | | | | | | | | | | | | | | |
| 1 hours | 20.1 | BRL | BRL | BRL | BRL | BRL | BRL | BRL | 0.12 | 0.05 | BRL | BRL | BRL | BRL | 0.17 |
| 4 hours | 19.9 | BRL | BRL | BRL | BRL | BRL | BRL | BRL | 0.12 | 0.05 | BRL | BRL | BRL | BRL | 0.17 |

Example 7

Stability of Frozen Intravenous Bags

The following formulation of methylnaltrexone 5 mg/ml, 0.8 mg of NaCL, 0.1 mg CaEDTA, 0.1 mg Glycine Hydrochloride, and water for injection was infused in 100 ml IV bags of 0.9% of Normal Saline and frozen at −200 C. The study was conducted for two concentrations of methylnaltrexone: 12 mg/100 ml and 24 mg/100 ml. B/Braun bags NDC 0264-1800-32 with 0.9% of Normal Saline were used.

TABLE 15

5 mg/ml Methylnaltrexone, 0.8 mg of NaCL, 0.1 mg CaEDTA, 0.1 mg Glycine HCl

| | | Impurities | | | | | | |
|---|---|---|---|---|---|---|---|---|
| Sample name | Strength, mg/ml | RRT 0.67 | RRT 0.79 | RRT 0.89 | RRT 1.55 | RRT 1.76 | RRT 2.24 | Total |
| *12 mg/100 ml of 0.9% Normal Saline bag* | | | | | | | | |
| Initial | 0.11 | ND | ND | ND | ND | ND | ND | NA |
| 2 weeks | 0.11 | ND | ND | ND | ND | ND | ND | NA |

TABLE 15-continued 5 mg/ml Methylnaltrexone, 0.8 mg of NaCL,
0.1 mg CaEDTA, 0.1 mg Glycine HCl

| Sample name | Strength, mg/ml | Impurities | | | | | | |
|---|---|---|---|---|---|---|---|---|
| | | RRT 0.67 | RRT 0.79 | RRT 0.89 | RRT 1.55 | RRT 1.76 | RRT 2.24 | Total |
| 1 month | 0.11 | ND | ND | ND | ND | ND | ND | NA |
| 2 months | 0.12 | ND | ND | ND | ND | ND | ND | NA |
| 24 mg/100 ml bag of 0.9% Normal Saline bag | | | | | | | | |
| Initial | 0.22 | ND | ND | ND | ND | 0.07 | ND | 0.07 |
| 2 weeks | 0.22 | ND | ND | ND | ND | 0.07 | ND | 0.07 |
| 1 month | 0.23 | ND | ND | ND | ND | 0.06 | ND | 0.06 |
| 2 months | 0.23 | ND | ND | ND | ND | 0.06 | ND | 0.06 |

Example 8

The effect of sodium tungstate (HPLC Method A) on the subcutaneous formulation described herein is summarized in Table 16, below.

TABLE 16

Effect of 1 mM Sodium Tungstate on Subcutaneous Formulation

| Sample | 7-Di-hydroxy MNTX | Ring Contraction Degradant | O-Methyl MNTX | Total |
|---|---|---|---|---|
| Room Temperature | | | | |
| Methylnaltrexone Initial | BRL | BRL | 0.12 | 0.12 |
| Methylnaltrexone 1 hour | BRL | BRL | 0.12 | 0.12 |
| Methylnaltrexone 2 hours | 0.02 | BRL | 0.12 | 0.14 |
| Methylnaltrexone 3 hours | 0.02 | BRL | 0.12 | 0.14 |
| Methylnaltrexone 4 hours | 0.02 | BRL | 0.12 | 0.14 |
| Methylnaltrexone 5 hours | 0.02 | BRL | 0.12 | 0.14 |
| Methylnaltrexone + 1 mM Sodium Tungstate Initial | BRL | BRL | 0.12 | 0.12 |
| Methylnaltrexone + 1 mM Sodium Tungstate 1 hour | 0.02 | BRL | 0.12 | 0.14 |
| Methylnaltrexone + 1 mM Sodium Tungstate 2 hours | 0.02 | BRL | 0.12 | 0.14 |
| Methylnaltrexone + 1 mM Sodium Tungstate 3 hours | 0.03 | BRL | 0.12 | 0.15 |
| Methylnaltrexone + 1 mM Sodium Tungstate 4 hours | 0.03 | BRL | 0.12 | 0.15 |
| Methylnaltrexone + 1 mM Sodium Tungstate 5 hours | 0.03 | BRL | 0.12 | 0.15 |
| 40° C. | | | | |
| Methylnaltrexone Initial | BRL | BRL | 0.12 | 0.12 |
| Methylnaltrexone 1 hour | BRL | BRL | 0.12 | 0.12 |
| Methylnaltrexone 2 hours | 0.02 | BRL | 0.12 | 0.14 |
| Methylnaltrexone 3 hours | 0.02 | BRL | 0.12 | 0.14 |
| Methylnaltrexone 4 hours | 0.02 | BRL | 0.12 | 0.14 |
| Methylnaltrexone 5 hours | 0.03 | BRL | 0.12 | 0.15 |
| Methylnaltrexone + 1 mM Sodium Tungstate Initial | BRL | BRL | 0.12 | 0.12 |
| Methylnaltrexone + 1 mM Sodium Tungstate 1 hour | 0.02 | BRL | 0.12 | 0.14 |
| Methylnaltrexone + 1 mM Sodium Tungstate 2 hours | 0.02 | BRL | 0.12 | 0.14 |
| Methylnaltrexone + 1 mM Sodium Tungstate 3 hours | 0.03 | BRL | 0.12 | 0.15 |
| Methylnaltrexone + 1 mM Sodium Tungstate4 hours | 0.03 | BRL | 0.12 | 0.15 |
| Methylnaltrexone + 1 mM Sodium Tungstate 5 hours | 0.03 | BRL | 0.12 | 0.15 |

Part II: Subcutaneous Formulations

Example 9

A room temperature methylnaltrexone formulation 20 mg/mL subcutaneous solution for injection, CaEDTA formulation consists of 20 mg/mL methylnaltrexone bromide, 0.4 mg/mL edetate calcium disodium (CaEDTA), 0.3 mg/mL glycine hydrochloride and 0.65% sodium chloride in water for injection. The product, which is stable at room temperature storage conditions, is filled aseptically in single-use vials at 0.6 mL volume or 12 mg methylnaltrexone per vial to be administered subcutaneously.

The sodium chloride concentration is adjusted to 0.65% to maintain the tonicity of the formulation.

Such a room temperature formulation for subcutaneous administration was prepared as summarized in Tables 17A, 17B, and 17C below:

TABLE 17A

Methylnaltrexone 20 mg/mL Subcutaneous Solution for Injection,

| | | SC Commercial |
|---|---|---|
| Formulation | Strength | 20 mg/mL |
| | Type | Liquid Solution |
| Container/Closure | Vial | 3 mL |
| | Stopper | 13 mm |
| mg/vial | Methylnaltrexone | 12 mg |
| | CaEDTA | 0.32 |
| | Glycine HCl | 0.24 |
| | NaCl | 5.20 |
| | Overage | 33% (0.2 ml) |
| Processing | Sterilization | Aseptic |
| | Nitrogen Flush | Yes |
| | Fill Volume | 0.8 mL |
| Dispensing | Container | Syringe |
| | Dilution | None |

TABLE 17B

Methylnaltrexone 20 mg/mL Subcutaneous Solution for Injection,

| | Room Temperature |
|---|---|
| MNTX | 20 mg/mL |
| CaEDTA[#] | 0.40 mg/mL |
| Glycine HCL | 0.30 mg/mL |
| NaCl | 6.5 mg/mL |
| Osmolarity (mOsm/Kg) | 286 |
| pH | 3-5 |
| Volume of injection (mL) | 0.6 |

TABLE 17C

Methylnaltrexone 20 mg/mL Subcutaneous Solution
for Injection, Quantitative Composition
Methylnaltrexone 20 mg/mL Subcutaneous Solution
for Injection, CaEDTA Formulation, Batch Size: 5000 mL

| | | Input/Dosage Unit | |
|---|---|---|---|
| Ingredient | % WT/WT | Input | Unit |
| Naltrexone Methobromide | 1.985 | 16 | mg |
| Calcium EDTA, USP | 0.040 | 0.32 | mg |
| Sodium Chloride, USP | 0.644 | 5.2 | mg |
| Glycine Hydrochloride | 0.030 | 0.24 | mg |
| Water for Injection, USP | NA | QS to 0.80 | mL |
| Hydrochloric Acid, NF[b] | N/A | N/A | |
| Sodium Hydroxide, NF[b] | N/A | N/A | |

In certain embodiments, the above formulation for subcutaneous administration may be dosed according to the following table. Patients whose weight falls outside the recited ranges may be dosed at 0.15 mg/kg.

| Patient Weight | | Injection | |
|---|---|---|---|
| Pounds | Kilograms | Volume | Dose |
| 84 to less than 136 | 38 to less than 62 | 0.4 mL | 8 mg |
| 136 to 251 | 62 to 114 | 0.6 mL | 12 mg |

In other embodiments, in patients with severe renal impairment (creatinine clearance less than 30 mL/min) the above formulation for subcutaneous administration dose may be reduced by one-half.

Example 10

As described herein, the present invention provides a pre-filled syringe containing a methylnaltrexone formulation in accordance with the present invention. Such a pre-filled syringe is described below in Table 18.

TABLE 18

| Pre-filled Syringe | | |
|---|---|---|
| | | Concentration/Limits |
| Active Ingredients | | |
| Methylnaltrexone Bromide | | 20 mg/mL |
| Excipients | | |
| Calcium Disodium Edetate | | 0.4 mg/mL |
| Glycine Hydrochloride | | 0.3 mg/mL |
| Sodium Chloride | | 6.5 mg/mL |
| Water for Injection (WFI) | | Ad 1.0 mL |
| Primary Packaging Materials | Type | Material |
| SCF Syringe 1 mL-l with Rigid Needle Shield (RNS) | BD | Glass: Type 1 Needle: Stainless steel AISI 304, CN18/10, 27G1/2, 5-bevel Soft needle shield: FM27/0 modified Rigid shell: Polypropylene |
| SCF Stopper | BD | Basic raw material: bromobutyl rubber, 4023/50, grey Coating: contact side with Daikyo foil, remaining part: B2-40 coated |

Example 11

Subcutaneous Formulation—Bioequivalency Study

A bioequivalency study comparing the subcutaneous formulation described at Example 9 and a formulation containing only methylnaltrexone in saline was performed in an open-label, single-dose, randomized, 2-period, 2-sequence crossover, inpatient/outpatient study in healthy subjects conducted at a single investigational site. Doses were administered after an overnight fast of at least 10 hours. Healthy men and nonlactating and nonpregnant women aged 18 to 50 years were eligible for enrollment if all other qualifying criteria were met. At approximately 0800 on day 1 of periods 1 and 2, each subject received an SC injection containing 0.15 mg/kg of methylnaltrexone (the period 1, day −1 weight was used to determine the dose to be administered). Standard medium fat-meals, served according to the clinic's schedule, could start 3 hours after test article administration. Vital signs, ECGs, laboratory evaluations, and pharmacokinetic (PK) sample collection were completed at designated times on days 1, 2, and 3 of period 1 and 2 as per the study flowchart.

Each subject was to receive a single SC dose of 0.15 mg/kg of the assigned formulation of methylnaltrexone on day 1 of each period after an overnight fast of at least 10 hours. The injection was administered SC into the upper arm and the same arm was to be used for each injection. The injection site was to be healthy appearing skin. Every attempt was made to have the same person administer both formulations to each subject. The dose was determined from the subject's weight on day −1 of period 1. The syringes were weighed before and after test article administration to verify the volume injected. Each single dose was separated by a washout interval of at least 7 days. Blood samples were obtained for the determination of the pharmacokinetics of methylnaltrexone. Blood samples (6 mL) were collected from an indwelling catheter or by direct venipuncture. If a catheter was used for blood collection, then approximately 0.5 mL of blood were to be discarded before collecting the sample at each sampling time. Blood samples were collected in each period on day 1 within 2 hours before test article administration and at 0.083, 0.25, 0.5, 0.75, 1, 1.5, 2, 3, 4, 6, 8, 12, 16, 24, 36, and 48 hours after test article administration. Results of pharmaceokinetic studies are set forth in Table 19, below.

TABLE 19

Methylnaltrexone Pharmacokinetic Parameters for SC Methylnaltrexone Formulations in 27 Healthy Subjects at a Dose of 0.15 mg/kg

| Formulation | $C_{max}$ ng/mL | $AUC_t$ ng h/ml | $AUC_\infty$ ng h/ml | $T_{1/2}$ (h) | $t_{max}$ (h) |
|---|---|---|---|---|---|
| Saline | 119 ± 33 | 221 ± 36 | 223 ± 36 | 9.2 ± 2.5 | 0.41 |
| (min, max) | (62.6, 197) | (163, 333) | (168, 335) | (7.0, 19.4) | (0.08, 1.0) |
| Example 9 | 127 ± 34 | 218 ± 37 | 220 ± 37 | 8.4 ± 1.4 | 0.34 |
| (min, max) | (82.9, 188) | (165, 333) | (172, 335) | (6.4, 13.8) | (0.08, 1.0) |

As shown in Table 19 above, the mean methylnaltrexone concentration-versus-time profile after the SC administration of a formulation of Example 9 was essentially identical to that seen with a saline formulation. Plasma methylnaltrexone concentrations increased sharply in response to SC administration of either formulation, with a mean Cmax of 127 ng/mL for a provided formulation and 119 ng/mL for the saline formulation, observed mostly within the first hour (mean tmax of 0.34 h and 0.41 h, respectively).

Example 12

Pharmacokinetic Screening of Methylnaltrexone Subcutaneous Formulation in Dogs

Three different methylnaltrexone formulations administered subcutaneously were evaluated in dogs. Pharmacokinetics of methylnaltrexone following a single subcutaneous 0.15 mg/kg dose in male beagle dogs. Eight male dogs (9.4-15 kg) were divided into two groups, four dogs per group. To both groups of dogs, 0.15 mg/kg methylnaltrexone in normal saline (Batch 1) was administered subcutaneously as a reference formulation during period 1. A week later, during period 2, Group 1 (SAN 1-4) received 0.15 mg/kg methylnaltrexone subcutaneously in saline containing 0.5 mg/vial Na. EDTA and 0.6 mM Citrate (Batch 2) and Group 2 (SAN 5-8) received 0.15 mg/kg methylnaltrexone subcutaneously in saline containing 0.5 mg/vial Ca. EDTA (Batch 3). Blood samples were drawn at 0 (predose), 0.0833, 0.167, 0.25, 0.5, 0.75, 1, 2, 4, 6, 8 and 12 hours after dosing, plasma was separated and assayed for methylnaltrexone content.

Bioanalytical results were obtained, and pharmacokinetic (PK) assessment was performed. Individual dog plasma methylnaltrexone concentration-time profiles were subjected to noncompartmental PK analyses (WinNonlin, Model 200). The following pharmacokinetic parameters were determined for each dog, and descriptive statistics were calculated for comparison among formulations: AUC, $C_{max}$, $t_{max}$ and $t_{1/2}$. See Table 20.

TABLE 20

Individual and Mean (±SD) Dog Plasma Methylnaltrexone Pharmacokinetic Parameters After a Single Subcutaneous Administration (~0.15 mg/kg) of Three Injectable Formulations

| Formulation | SAN | Batch 1 Reference | Batch 2 Test | Test/ Reference | SAN | Batch 1 Reference | Batch 3 Test | Test/ Reference |
|---|---|---|---|---|---|---|---|---|
| Dose | Mean | 0.149 | 0.150 | 1.01 | Mean | 0.152 | 0.154 | 1.02 |
| $AUC_{0-12}$ | Mean | 87.8 | 98.9 | 1.12 | Mean | 85.4# | 90.5 | 0.97 |
| (hr · ng/mL) | SD | 10.7 | 30.8 | 0.24 | SD | 5.1# | 20.5 | 0.15 |
| $AUC_{0-\infty}$ | Mean | 102 | 111 | 1.09 | Mean | 106 | 112 | 0.99 |
| (hr · ng/mL) | SD | 9.4 | 27.9 | 0.19 | SD | 9.3 | 21.2 | 0.12 |
| $AUC_{0-12}/$ | Mean | 590 | 656 | 1.11 | Mean | 570# | 585 | 0.95 |
| Dose | SD | 64.2 | 178 | 0.22 | SD | 45.0# | 122 | 0.15 |
| $C_{max}$ (ng/mL) | Mean | 83.7 | 107 | 1.35 | Mean | 128# | 130 | 1.01 |
|  | SD | 33.8 | 44.4 | 0.50 | SD | 22.5# | 34.6 | 0.42 |
| $T_{max}$ (hr) | Mean | 0.33 | 0.19 | 0.71 | Mean | 0.19# | 0.15 | 0.92 |
|  | SD | 0.19 | 0.04 | 0.34 | SD | 0.05# | 0.08 | 0.44 |
| $t_{1/2}$ (1/hr) | Mean | 10.1* | 9.3* | 1.15 | Mean | 13.0* | 13.8* | 1.20 |
|  | SD | 5.0 | 3.3 | 0.79 | SD | 4.0 | 3.5 | 0.19 |

Part III: Intravenous Formulations

Example 12

In certain embodiments, the present invention provides a methylnaltrexone formulation for intravenous administration. Provided intravenous formulations can be prepared in 12 mg/vial or 24 mg/vial concentrations. Both 12 mg/vial and 24 mg/vial strengths use a 5 mg/mL concentration of methylnaltrexone. In certain embodiments, provided intravenous formulations utilize a 10 mL spikable vial designed to be used with Baxter mini-bags or any other spikable infusion system. In some embodiments, provided formulations were subjected to terminal sterilization by heating at 121° C. for 15 minutes.

Formulations prepared in 12 mg/vial or 24 mg/vial concentrations are set forth in Tables 20A and 20B, respectively, below. Such formulations can be administered at doses of 24 mg, or also, for example, 0.3 mg/kg, every 6 hours as a 20-minute infusion. In certain embodiments, such administration is continued for 3 days (total of 12 doses). Each methylnaltrexone formulation is diluted to 50 mL and administered using a calibrated pump.

TABLE 20A

Methylnaltrexone IV formulation for 12 mg/Vial

| Ingredient | % WT/WT | Input/Dosage Unit Input | Unit |
|---|---|---|---|
| Naltrexone Methobromide | 0.496 | 25.2 | mg |
| Calcium EDTA, USP | 0.0099 | 0.504 | mg |
| Sodium Chloride, USP | 0.833 | 42.336 | mg |
| Glycine Hydrochloride | 0.0099 | 0.504 | mg |
| Water for Injection, USP | NA | QS to 2.54 | mL |

| | | IV | |
|---|---|---|---|
| Formulation | Strength | 5 mg/mL | |
|  | Type | Liquid Solution | |
| Container/Closure | Vial | 10 mL | 10 mL |
|  | Stopper | 20 mm | 20 mm |
| mg/vial | Methylnaltrexone | 12 mg | 24 mg |
|  | CaEDTA | 0.24 mg | 0.48 mg |
|  | Glycine HCl | 0.24 mg | 0.48 mg |
|  | NaCl | 20.16 mg | 40.32 mg |
|  | Overage | 5% | 5% |

TABLE 20A-continued

Methylnaltrexone IV formulation for 12 mg/Vial

| Processing | Sterilization | Terminal | Terminal |
|---|---|---|---|
|  | Nitrogen Flush | No * | No * |
|  | Fill Volume | 2.52 ml | 5.04 ml |
|  |  | (12 mg/vial); | (24 mg/vial) |

TABLE 20A-continued

Methylnaltrexone IV formulation for 12 mg/Vial

| Dispensing | Container Dilution | Syringe/spike Dilution/admix | Syringe/spike Dilution/admix |
|---|---|---|---|

TABLE 20B

Methylnaltrexone IV formulation for 24 mg/Vial

| DESCRIPTION | AMT. NEEDED PER UNIT | |
|---|---|---|
| Methylnaltrexone | 25.2 | mg |
| Calcium EDTA, USP | 0.504 | mg |
| Sodium Chloride, USP | 42.336 | mg |
| Glycine Hydrochloride | 0.504 | mg |
| Water for Injection, USP$^a$ | 5.08$^c$ | g |
| Hydrochloric Acid, NF$^b$ | As needed | NA |
| Sodium Hydroxide, NF$^b$ | As needed | NA |
| Containers & Closures | | |
| 10 mL Schott flint glass vial with 20 mm neck 20 MM, GREY, S10-F451 4432/50 FLUROTEC PLUG XKD484 20 mm, Aluminum seal with Flip-top | | |

| Ingredient | % WT/WT | Input/Dosage Unit Input | Unit |
|---|---|---|---|
| Methylnaltrexone | 0.496 | 25.2 | mg |
| Calcium EDTA, USP | 0.0099 | 0.504 | mg |
| Sodium Chloride, USP | 0.833 | 42.336 | mg |
| Glycine Hydrochloride | 0.0099 | 0.504 | mg |
| Water for Injection, USP | NA | QS to 5.04 | mL |

In certain embodiments, fill volume is at least 2.6 mL for a 2.4 mL extractable volume, and at least 5.1 mL for a 4.8 mL extractable volume. Table 20C below describes vial contents dilution when using a traditional syringe or a spikable vial.

TABLE 20C

Overage and Reconstitution of Sample

| | spikable technique with Baxter Mini-bag | | traditional syringe withdrawal | |
|---|---|---|---|---|
| Concentration | 5 mg/mL | 5 mg/mL | 5 mg/mL | 5 mg/mL |
| mg/vial | 12 mg | 24 mg | 12 mg | 24 mg |
| Overage | 5% | 5% | 5% | 5% |
| Fill volume | 2.52 | 5.04 | 2.52 | 5.04 |
| Reconstitution volume | 8.0 mL of saline solution | 5.0 mL of saline solution | 8.0 mL of saline solution | 5.0 mL of saline solution |
| Withdrawal amount | Spike full contents of vial | Spike full contents of vial | Withdraw 10.0 mL via syringe | Withdraw 10.0 mL via syringe |

Example 14

In certain embodiments, a provided intravenous formulation is administered to a patient 90 minutes post surgery, where the surgery is hernia repair. In some embodiments, the hernia repair patient is administered opioids via PCA pump. Such formulations can be administered at doses of 12 mg or 24 mg, or also, for example, 0.3 mg/kg, every 6 hours as a 20-minute infusion. In certain embodiments, such administration is continued for 10 days, the patient is discharged, or 24 hours post-bowel movement.

One skilled in the art will readily ascertain the essential characteristics of the invention, and understand that the foregoing description and examples are illustrative of practicing the provided invention. Those skilled in the art will be able to ascertain using no more than routine experimentation, many variations of the detail presented herein may be made to the specific embodiments of the invention described herein without departing from the spirit and scope of the present invention.

Patents, patent applications, publications, and the like are cited throughout the application. The disclosures of each of these documents are incorporated herein by reference in their entirety.

We claim:

1. A pharmaceutical composition comprising an effective amount of methylnaltrexone or a pharmaceutically acceptable salt thereof, about 0.4 mg/mL of calcium ethylenediaminetetraacetic acid (EDTA) disodium, and about 0.1 mg/mL to about 0.8 mg/mL of glycine in an aqueous solution, wherein the solution has a pH of about 3 to 4.

2. The pharmaceutical composition of claim 1, wherein the pharmaceutically acceptable salt of methylnaltrexone comprises methylnaltrexone bromide.

3. The pharmaceutical composition of claim 1, wherein the composition comprises about 5 mg to about 40 mg of methylnaltrexone or a pharmaceutically acceptable salt thereof.

4. The pharmaceutical composition of claim 1, wherein the glycine comprises glycine HCl.

5. The pharmaceutical composition of claim 1, wherein the solution has a pH of about 3.4 to about 3.6.

6. The pharmaceutical composition of claim 1, wherein the solution has a pH of about 3.5.

7. The pharmaceutical composition of claim 1, further comprising sodium chloride.

8. The pharmaceutical composition of claim 1, wherein the pharmaceutical composition is a unit dose contained in a vial, ampoule, or syringe for subcutaneous administration to a subject.

9. The pharmaceutical composition of claim 1, wherein the concentration of degradation products in the composition following six months of room temperature storage conditions is characterized by one or more of the following:
   a. the concentration of total degradation products does not exceed about 1.25% of methylnaltrexone or the pharmaceutically acceptable salt thereof;
   b. the concentration of 2,2' bis-methylnaltrexone degradant product (RRT 1.55) does not exceed about 0.2% of methylnaltrexone or the pharmaceutically acceptable salt thereof;
   c. the concentration of 7-dihydroxymethylnaltrexone degradant product (RRT 0.67) does not exceed about 0.2% of methylnaltrexone or the pharmaceutically acceptable salt thereof;
   d. the concentration of the ring contracted methylnaltrexone degradant product (RRT 0.79) does not exceed about 0.2% of methylnaltrexone or the pharmaceutically acceptable salt thereof;
   e. the concentration of aldol dimer methylnaltrexone degradant product (RRT 1.77) does not exceed about 0.2% of methylnaltrexone or the pharmaceutically acceptable salt thereof;
   f. the concentration of Hoffman elimination methylnaltrexone degradant product (RRT 2.26) does not exceed about 0.2% of methylnaltrexone or the pharmaceutically acceptable salt thereof; and g. the concentration of O-methyl methylnaltrexone (RRT 1.66) does not exceed about 0.25% of methylnaltrexone or the pharmaceutically acceptable salt thereof.

10. A method of preparing a methylnaltrexone formulation for parenteral administration, the method comprising the steps of:
mixing calcium EDTA, or a calcium salt EDTA derivative, and glycine with a solution of methylnaltrexone, or a pharmaceutically acceptable salt thereof;
adjusting the pH to about 3.0 to about 4.0; and
sterilizing the resulting solution, thereby preparing the methylnaltrexone formulation, wherein the formulation comprises about 0.2 mg/mL to about 0.8 mg/mL of calcium EDTA, or a calcium EDTA derivative, and about 0.1 mg/mL to about 0.8 mg/mL of glycine.

11. The method of claim 10, wherein the salt of methylnaltrexone comprises methylnaltrexone bromide.

12. The method of claim 10, wherein the calcium salt EDTA derivative comprises calcium EDTA disodium.

13. The method of claim 10, wherein the glycine comprises glycine HCl.

14. The method of claim 10, wherein the pH is adjusted to about 3.4 to about 3.6.

15. The method of claim 10, further comprising adding sodium chloride to the solution of methylnaltrexone, or a pharmaceutically acceptable salt thereof.

16. A method for reducing a side effect of opioid treatment in a subject receiving opioid treatment, comprising administering the pharmaceutical composition of claim 1 to the subject.

17. The pharmaceutical composition of claim 1 in a sealed container.

18. The pharmaceutical composition of claim 17, wherein the container is selected from the group consisting of a vial, an ampoule, a bag, a bottle, a syringe, and a dispenser package.

19. The method of claim 16, wherein the side effect is opioid induced constipation.

* * * * *